(12) United States Patent
Barnea et al.

(10) Patent No.: US 6,867,283 B2
(45) Date of Patent: Mar. 15, 2005

(54) PEPTIDES CAPABLE OF BINDING TO MHC MOLECULES, CELLS PRESENTING SUCH PEPTIDES, AND PHARMACEUTICAL COMPOSITIONS COMPRISING SUCH PEPTIDES AND/OR CELLS

(75) Inventors: Eilon Barnea, Nesher (IL); Ilan Beer, Haifa (IL); Tamar Ziv, Haifa (IL); Arie Admon, Kiryat Tivon (IL)

(73) Assignee: Technion Research & Development Foundation Ltd., Haifa (IL)

( * ) Notice: Subject to any disclaimer, the term of this patent is extended or adjusted under 35 U.S.C. 154(b) by 225 days.

(21) Appl. No.: 09/865,548

(22) Filed: May 29, 2001

(65) Prior Publication Data

US 2003/0096298 A1 May 22, 2003

Related U.S. Application Data

(60) Provisional application No. 60/290,958, filed on May 16, 2001.

(51) Int. Cl.[7] .............................................. A61K 38/08
(52) U.S. Cl. ......................... 530/328; 514/15; 530/300; 424/278.1
(58) Field of Search ......................................... 530/328

(56) References Cited

U.S. PATENT DOCUMENTS

| | | |
|---|---|---|
| 2002/0122820 A1 | 9/2002 | Hildebrand et al. |
| 2002/0156730 A1 | 10/2002 | Hildebrand et al. |
| 2002/0197672 A1 | 12/2002 | Hildebrand et al. |

FOREIGN PATENT DOCUMENTS

| | | |
|---|---|---|
| WO | WO 02/30964 | 4/2002 |
| WO | WO 02/056908 | 7/2002 |
| WO | WO 02/062846 | 8/2002 |
| WO | WO 02/069198 | 9/2002 |
| WO | WO 02/072606 | 9/2002 |

OTHER PUBLICATIONS

Database MEDLINE, DN 99008337. Niederreither et al. Oncogene, 17,1577–15895, 1998.*

Jin, Y. et al., "Stereoselective Synthesis of Dithymidine Phosphorothioates Using Xylose Derivatives as Chiral Auxiliaries," *J. Org. Chem.*, 1998, 63, 3647–3654.

Koziolkiewicz, M. et al., "Stereodifferentiation—the effect of P chirality of oligo(nucleoside phosphorothioates) on the activity of bacterial RNase H," *Nucl. Acids Res.*, 1995, 23(24), 5000–5005.

Kataoka, M. et al., "Imidazolium Triflate as an Efficient Promoter for O–selective Phoshitylation of N–unprotected Nucleosides via the Phosphoramidite Approach," *Nucl. Acids*, 1997, 21–22.

Stec, W. J. et al., "Stereocontrolled Synthesis of Oligo-(nucleoside phosphorothioate)s," *Angew. Chem. Int. Ed. Engl.*, 1994, 33, 709–722.

Stec, W. J. et al., "Diastereomers of Nucleoside 3'–O–(2–THio–1,3,2–ozathia(selena)phospholanes): Building Blocks for Stereocontrolled Synthesis of Oligo(nucleoside Phosphorothioate)s," *J. Am. Chem. Soc.*, 1995, 117(49), 12019–12029.

Froehler, B.C. "Oligodeoxynucleotide Synthesis, H–Phosphate approach" *Methods in Molecular Biology*, edited by Sudhir Agrawal, 1993, Humana Press, vol 20 pp 63–80.

Wang, J. C. et al., "A Stereoselective Synthesis of Dinucleotide Phosphorothioates, Using Chiral Indol–oxazaphosphorine Intermediates," *Tetra. Lett.*, 1997, 38(22), 3797–3800.

Wang, J. C. et al., "A Stereoselective Synthesis of Dinucleotide Phosphorothioate Triesters through a Chiral Indol–oxazaphosphorine Intermediate," *Tetra. Lett.*, 1997, 38(5), 705–708.

* cited by examiner

Primary Examiner—Michael Borin
(74) Attorney, Agent, or Firm—G.E. Ehrlich (1995) Ltd.

(57) ABSTRACT

A method of identifying peptides originating from a particular cell type and being capable of binding to MHC molecules of a particular haplotype is disclosed. The method comprises obtaining a cell type expressing a soluble and secreted form of the MHC molecules of the particular haplotype; collecting the soluble and secreted form of the MHC molecules of the particular haplotype; and analyzing peptides bound to the soluble and secreted form of the MHC molecules of the particular haplotype, thereby identifying the peptides originating from the particular cell type and being capable of binding to MHC molecules of the particular haplotype.

3 Claims, 5 Drawing Sheets

MAGE-B2: 231-240 GVYDGEEHSV (SEQ ID No: 19)
MAGE-A4: 231-240 GVYDGREHTV (SEQ ID No: 38)
MAGE-A10: 254-262 GLYDGMEHL (SEQ ID No: 39)
Fig. 4d
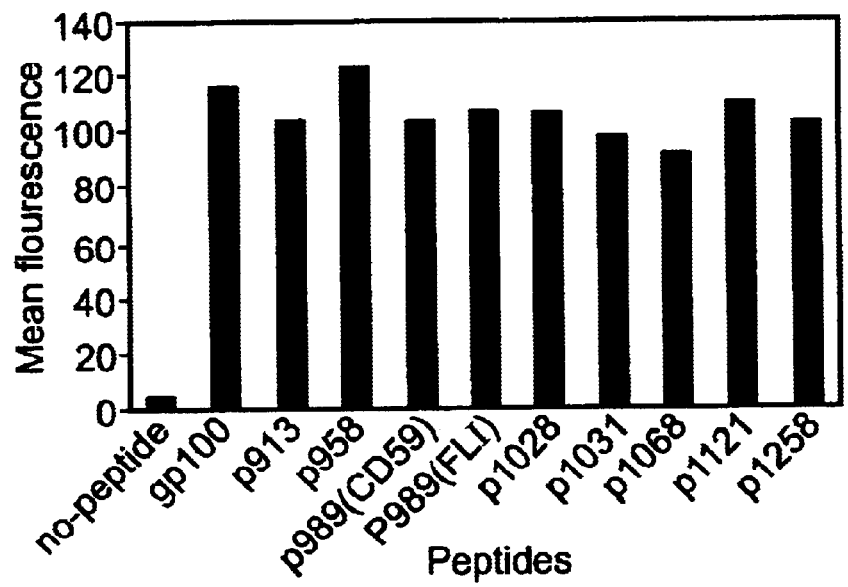
Fig. 5
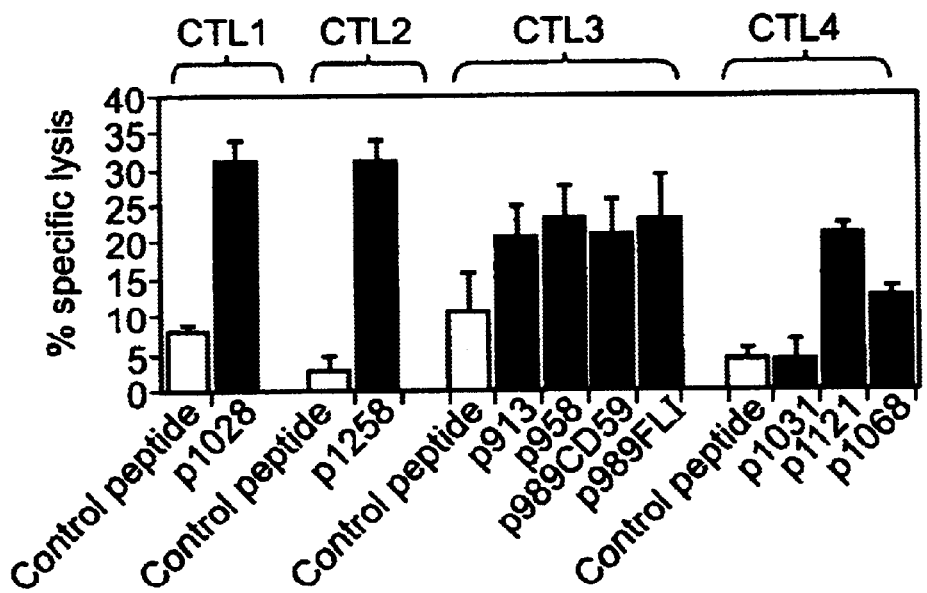
Fig. 6

PEPTIDES CAPABLE OF BINDING TO MHC MOLECULES, CELLS PRESENTING SUCH PEPTIDES, AND PHARMACEUTICAL COMPOSITIONS COMPRISING SUCH PEPTIDES AND/OR CELLS

This Application claims the benefit of priority from U.S. Provisional Patent Application No. 60/290,958, filed May 16, 2001.

FIELD AND BACKGROUND OF THE INVENTION

The present invention relates to a method of identifying peptides of a desired origin and which are capable of binding to MHC molecules of a particular haplotype; peptides identified by the method; pharmaceutical compositions containing the peptides, databases describing the peptides and the use of the peptides in vaccination.

The following abbreviations are used herein: MHC, Major Histocompatibility Complex; β2 m, β2-microglobulin; ESI, electrospray ionization; MS, mass spectrometry; m/z, mass charge ratio; CID, collision induced disintegration; MS/MS, tandem mass spectrometry; MTDM, DNA methyl transferase; FAS, fatty acid synthase; CTL, cytotoxic T lymphocytes; mAbs, monoclonal antibodies.

The MHC serves as a shuttle to transport and display peptide antigens on the surface of cells as an indication to the immune system of the health state of the cells. Each individual has at most six different MHC class-I haplotypes, out of the hundreds known. MHC bound peptides, i.e., peptides bound to, and presented in context of, MHC molecules, originate from proteolysis of most of the proteins expressed in the cells. Therefore, unique sets of MHC bound peptides are displayed by each of the different MHC haplotypes according to the protein expression and degradation schemes of the cells and according to the peptide binding motifs of the MHC molecules (reviewed in [1]). Therefore, thousands of different peptides are presented by the different MHC class-I haplotypes and each of the peptides is presented in vastly differing copies per cell [2]. When cells become infected, some of the presented peptides are derived from the pathogen's proteins, and so indicate to circulating T-cells to kill the diseased cells and prevent the spread of the disease.

Each MHC haplotype recognizes the peptides through a broadly defined consensus motif of peptide's amino acids strategically positioned to serve as anchors to the appropriate binding pockets on the MHC molecule. The binding motifs of many of the MHCs haplotypes were first established by pool Edman sequencing of unfractionated peptide mixtures eluted from immunoaffinity purified MHC molecules [3, 4]. The consensus was further extended by direct biochemical analysis of individual peptides separated by reversed phase chromatography and analyzed by tandem mass spectrometry [2, 5, 6], reviewed in [7].

MHC bound peptides derived from cancer specific or associated proteins or antigens were extensively searched for, with the goal of finding among them peptide candidates for development of anti-cancer vaccines. A number of such tumor specific peptides were already identified and some were successfully tested as anti-cancer vaccines for human treatment, most notably for immunotherapy of melanoma [8, 9]. Three main approaches were extensively used for the identification of such MHC bound peptides [10]. The genetic approach involves transfection of cDNA libraries, made from tumor cells, into cells that present the MHC allele of interest. The clones of transfected cells that stimulated CTL lines against the tumor cells were selected as the source for the tumor antigen and the genes were further fragmented to isolate the regions of the genes that encode the particular immunogenic peptide [11]. The second approach is based on exploiting the known consensus binding motifs of the MHC haplotype of interest to scan sequences of known protein "in silico" and to predict putative MHC bound peptides that fit this consensus [12]. For successful prediction, these consensus motifs should be a prior well established, which is not the case for many of the MHC haplotypes [13]. The drawback of this approach is its reliance on chemical synthesis of a large number of peptides, only few of which end up being useful. The biochemical, third approach, involves the fractionation of the MHC bound peptides by chromatography, assaying the fractions for immunoglogical activity and sequencing the individual peptides in the active fractions [2, 5]. The biochemical approach is the only possible way to identify post-translationally modified peptides, not always predictable from the protein sequences [14–16]. The biochemical approach depends on the availability of advanced mass spectrometry, needed for analyzing the available minute amounts of peptides that are present at very complex mixtures (reviewed in [7]).

All these approaches for identifying MHC bound peptides eventually rely on chemical synthesis of the peptides of interest to test their capacity to bind to the MHC molecule by stabilization of empty MHC molecules on cell surface [17], and their potential to elicit an immune response by tetramer assays [18], ELISPOT [19]and elicitation CTL responses when presented on cells [20].

Currently, sequencing and identification of individual MHC bound peptides the direct biochemical approach is most effectively performed by use of tandem mass spectrometry. The peptides are resolved by reversed phase chromatography and the elating peptides are collected, assayed for biological activity and sequenced, most often by electrospray tandem mass spectrometry [2, 5, 21]. Comparing the patterns of MHC bound peptides recovered from healthy and infected cells helps to identify disease related peptides [22]. Mass spectrometry is advantageous for such analysis due to its accuracy speed of analysis, its ability to analyze complex mixtures of peptides and its high sensitivity [7]. The biochemical analysis involves the purification of the MHC molecules with their bound peptides by immunoaffinity chromatography using mAbs specific for the native MHC [2]. To this end, the cells are solubilized with detergents, the desired MHC molecules are purified with their MHC bound peptides and the MHC bound peptides are recovered by denaturation and ultra-filtration. However, once the cells are disrupted by the detergents, the MHC molecules become contaminated by cellular debris and detergents which complicates the subsequent ESI-MS/MS analysis. Moreover, such immunoaffinity purification of desired MHC haplotypes is possible only when specific mAbs are available, whereas for many MHC haplotypes such mAbs are presently unavailable.

There is thus a widely recognized need for, and it would be highly advantageous to have, a method for identifying MHC bound peptides devoid of the above limitations.

SUMMARY OF THE INVENTION

While conceiving the present invention, it was hypothesized that MHC bound peptides presented within the context of different MHC haplotypes on cells of different tissues or tumor origins can be biochemically identified by transforming the cells to express and secrete soluble MHC molecules of the different MHC haplotypes, with the aim of biochemically identifying the MHC bound peptides that bind to the soluble MHC molecules. Should this approach be successful, it solves three major problems associated with the prior art biochemical approach. First, although not excluded, there is no need for specific mAbs per each tipe of MHC, rather general mAbs such as W6/32 (anti HLA-A, B and C) can be used to isolate the sMHC and hence the MHC bound peptides from the growth medium in which the cells are grown. Second, while the prior art approach relies on native MHC molecules, different MHC haplotypes directing the expression of different soluble MHC molecules can potentially be used for each of the cells, to thereby increase the repertoire of MHC bound peptides which can be used as, for example, anti-cancer vaccines. Third, since the cells are not disrupted and further since there is no use of detergents, the sMHC molecules do not become contaminated by cellular debris and detergents which otherwise complicates the subsequent ESI-MS/MS analysis.

According to one aspect of the present invention there is provided a method of identifying peptides originating from a particular cell type and being capable of binding to MHC molecules of a particular haplotype, the method comprising obtaining a cell type expressing a soluble and secreted form of the MHC molecules of the particular haplotype; collecting the soluble and secreted form of the MHC molecules of the particular haplotype; and analyzing peptides bound to the soluble and secreted form of the MHC molecules of the particular haplotype, thereby identifying the peptides originating from the particular cell type and being capable of binding to MHC molecules of the particular haplotype.

According to further features in preferred embodiments of the invention described below, the cell type is a cancer cell.

According to still further features in the described preferred embodiments the cell type is a cancer cell line.

According to still further features in the described preferred embodiments the cell type is a virus infected cell or cell line.

According to still further features in the described preferred embodiments the cell type is a cell involved in a development and/or progression of an autoimmune diseases.

According to another aspect of the present invention there is provided a method of identifying peptides originating from at least one protein of interest and being capable of binding to MHC molecules of a particular haplotype, the method comprising obtaining cells co-expressing the at least one protein of interest and a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from the at least one protein of interest and being capable of binding to MHC molecules of the particular haplotype.

According to further features in preferred embodiments of the invention described below, the protein of interest in natively expressed by the cells.

According to still further features in the described preferred embodiments the at least one protein of interest in expressed by the cells following transformation of the cells with nucleic acid encoding for the at least one protein of interest.

According to still further features in the described preferred embodiments the at least one protein of interest includes a tumor associated antigen.

According to still further features in the described preferred embodiments the at least one protein of interest includes a cytokine.

According to still further features in the described preferred embodiments the at least one protein of interest includes a protein of a pathogen.

According to still further features in the described preferred embodiments the soluble and secreted form of the MHC molecules include a polypeptide encoded by exons 5 to 8 of a murine mutant $Q10^b$.

According to still further features in the described preferred embodiments analyzing the peptides bound to the soluble and secreted form of the MHC molecules of the particular haplotype is by mass spectrometry, mass charge ratio and collision induced disintegration.

According to still further features in the described preferred embodiments identifying peptides originating from the at least one protein of interest and being capable of binding to MHC molecules of the particular haplotype is by comparison to a protein database.

According to another aspect of the present invention, there is provided an electronic data storage device, storing, in a retrievable form, a plurality of sequences of peptides identified by the methods described herein.

According to still another aspect of the present invention, there is provided a kit comprising a plurality of individual containers, each of the plurality of individual containers containing at least one peptide identified by the methods described herein.

According to yet another aspect of the present invention there is provided a method of identifying peptides originating from cancer associated proteins and being capable of binding to MHC molecules of a particular haplotype, the method comprising obtaining a cancer cell type expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from cancer associated proteins and being capable of binding to MHC molecules of the particular haplotype.

According to still another aspect of the present invention there is provided a method of identifying peptides originating from cells participating in the development and/or progression of an autoimmune disease and being capable of binding to MHC molecules of a particular haplotype, the method comprising obtaining cells participating in the development and/or progression of the autoimmune disease and expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from proteins participating in the development and/or progression of the autoimmune disease and being capable of binding to MHC molecules of the particular haplotype.

According to an additional aspect of the present invention there is provided a method of identifying peptides originating from virus infected cells and being capable of binding to MHC molecules of a particular haplotype, the method comprising obtaining virus infected cells expressing a soluble and secreted form of the MHC molecules of the particular haplotype collecting the soluble and secreted form of the MHC molecules of the particular haplotype; analyzing peptides bound to the soluble and secreted form of the MHC molecules of the particular haplotype; and identifying peptides originating from the virus and being capable of binding to MHC molecules of the particular haplotype.

According to yet an additional aspect of the present invention there is provided a method of identifying peptides originating from a particular cell type characterized by at least one of the following (i) cell over-expressing at least one protein; (ii) cells characterized by induced mutations; (iii) cells of metastases; (iv) normal or transformed cells expressing cell surface proteins, the peptides being capable of binding to MHC molecules of a particular haplotype, the method comprising obtaining cells of the particular cell type expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from the particular cell type and being capable of binding to MHC molecules of the particular haplotype.

According to still an additional aspect of the present invention there is provided an electronic data storage device, storing, in a retrievable form, a plurality of peptides being arranged at least according to their association with a pathology and further according to their ability of binding to MHC molecules of a particular haplotype.

According to a further aspect of the present invention there is provided an electronic data storage device, storing, in a retrievable form, a plurality of peptides being arranged at least according to their association with a protein of interest and further according to their ability of binding to MHC molecules of a particular haplotype.

According to yet a further aspect of the present invention there is provided a method of eliciting an immune response against a protein of interest in a subject having a particular MHC haplotype, the method comprising determining the subject's particular MHC haplotype; and administering to the subject an effective amount of at least one peptide derived from the protein of interest and which is capable of binding to MHC molecules of the particular haplotype.

According to still a further aspect of the present invention there is provided a method of treating a pathology by eliciting an immune response against a protein of interest in a subject having a particular MHC haplotype, the method comprising determining the subject's particular MHC haplotype; and administering to the subject a therapeutic effective amount of at least one peptide derived from the protein of interest and which is capable of binding to MHC molecules of the particular haplotype.

According to an additional aspect of the present invention, there is provided a method of eliciting an immune response against a protein of interest in a subject, the method comprising using an individualized in vitro assay for determining an immune reactivity of an immune system of the subject to a plurality of peptides derived from the protein of interest; and administering to the subject an effective amount of at least one peptide derived from the protein of interest and which is capable of inducing predetermined sufficient immune reactivity.

According to further features in preferred embodiments of the invention described below, administering to the subject the therapeutically effective amount of the at least one peptide is accompanied by presenting the at least one peptide in context of an antigen presenting cell.

According to still an additional aspect of the present invention, there is provided a peptide selected from the group consisting of SEQ ID NOs:4–6, 10–14, 19–21, 23–37, 44–88, 90–141, 143–144, 146–173, 175–189 and 191–195, all of which were never reported to bind MHC molecules.

According to still an additional aspect of the present invention, there is provided a peptide selected from the group consisting of SEQ ID NOs: 5, 9, 10 and 25.

According to yet an additional aspect of the present invention, there is provided a peptide selected from the group consisting of SEQ ID NOs:13, 20, 23 and 24.

According to another aspect of the present invention, there is provided a pharmaceutical composition comprising, as an active ingredient, at least one of the peptides described herein, and a pharmaceutically acceptable carrier. Preferably, the at least one of the peptides is presented in context of an antigen presenting cell.

According to further features in preferred embodiments of the invention described below, the peptide comprises at least one modification rendering peptides more stable in a body and/or more immunogenic.

According to still further features in the described preferred embodiments the at least one modification is selected from the group consisting of peptoid modification, semipeptoid modification, cyclic peptide modification, N terminus modification, C terminus modification, peptide bond modification, backbone modification and residue modification.

The present invention successfully addresses the shortcomings of the presently known configurations by providing a novel method for the identification of MHC bound peptides.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4A–D demonstrate the evaluation of the correctness of the MAGE-B2 peptide p1091 (GVYDGEEHSV, SEQ ID NO:20) by comparing the retention time and CID spectra of the synthetic peptide (4A) to that of the natural peptide m/z=1091.4 (SEQ ID NO:20) from the ovarian cancer line UCI-107 (4B). (4C) Evaluation of the binding affinity of peptide p1091 (SEQ ID NO:20) to HLA-A2 by reconstituting it into cells surface empty MHC of the RMA-S-HHD cells as assayed by FACS analysis. (4D) The homology between this MAGE-B2 peptide, p1091 (SEQ ID NO:20) to two other already known HLA-A2 peptides derived from homologous region in MAGE-A4 GVYDGREHTV (SEQ ID NO:38) [27] and MAGE-A10 proteins GLYDGMEHL (SEQ ID NO:39) [28].

FIG. 5 shows an example of reconstitution of peptides into cells surface MHC to test their binding and affinity as assayed by FACS analysis. Synthetic peptides were added to $10^6$ RMA-S-HHD cells to a concentration of 100 µM followed by incubation for two hours at 26° C. and two hours at 37° C. The stability of the peptides binding to the HHD cells was measured by indirect FACS assay after decoration for another hour with the W6/32 mAb at 4° C. and 30 minutes incubation with FITC goat anti-mouse Ab at 4° C. The HLA-A2.1 peptide derived from gp100 served as a positive control and unloaded RMA-S-HHD cells as a negative control.

FIG. 6 demonstrates a CTL assay with murine cells presenting human MHC (EL4-HHD). Cells were loaded separately with individual peptides, washed and injected in four groups: 1-p1028 (SEQ ID NO:13) alone, 2- p1258 (SEQ ID NO:24) alone, 3-pool of peptides: p913 (SEQ ID NO:5), p958 (SEQ ID NO:9), p989 of CD59 (SEQ ID NO:11) and p989 of FLI (SEQ ID NO:12), 4- peptides p1031 (SEQ ID NO:14), p1121 (SEQ ID NO:22) and p1068 (SEQ ID NO:16). Unloaded EL4-HHD or targets cells not loaded with the peptides were used as negative controls. An effector-to-target ratio of 50:1 is shown,

DESCRIPTION OF THE PREFERRED EMBODIMENTS

Figures 1A, 1B, 1C:
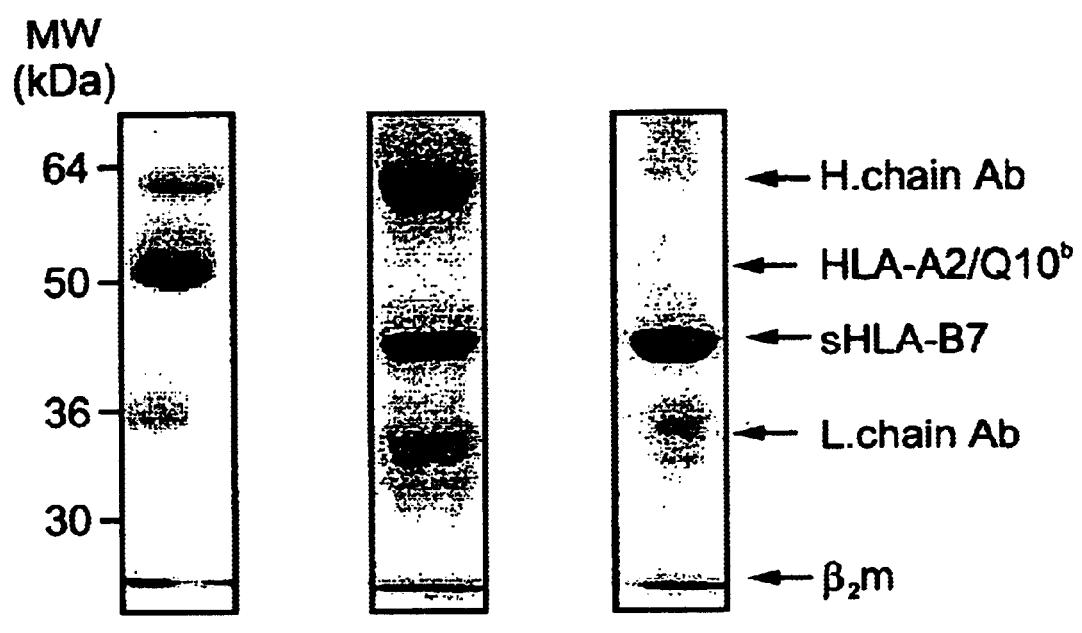
FIGS. 1A–C demonstrate the purification of soluble MHC from cancer cells. Soluble MHCs was purified by immunoaffinity from the growth medium of $5 \times 10^7$ transfected cells. Purified proteins were analyzed on 10% SDS-PAGE and stained with Coomassie blue. (1A) Purification of HLA-A2/Q10$^b$ from MCF-7 cells, (1B) Purification of sHLA-A2 from UCI-101 cells, (1C) Purification of sHLA-B7 from UCI-107 cells.

The present invention is of a method of identifying peptides of a desired origin, such as tumor associated antigens, pathogen (e.g., virus, bacteria) derived antigens, endogenous cytokines, etc., which are capable of binding to MHC molecules of a particular haplotype. The present invention is further of peptides identified by the method and pharmaceutical compositions containing the peptides. Still, the present invention is further of databases describing the peptides and the use of the peptides in vaccination to treat and/or prevent various pathologies, cancer and autoimmune diseases, in particular.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of identifying peptides originating from a particular cell type and being capable of binding to MHC molecules of a particular haplotype. The method according to this aspect of the present invention is effected by obtaining a cell type expressing a soluble and secreted form of the MHC molecules of the particular haplotype; collecting the soluble and secreted form of the MHC molecules of the particular haplotype; and analyzing peptides bound to the soluble and secreted form of the MHC molecules of the particular haplotype, thereby identifying the peptides originating from the particular cell type and being capable of binding to MHC molecules of the particular haplotype.

According to another aspect of the present invention there is provided a method of identifying peptides originating from cancer associated proteins and being capable of binding to MHC molecules of a particular haplotype. The method according to this aspect of the present invention is effected by obtaining a cancer cell type expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from cancer associated proteins and being capable of binding to MHC molecules of the particular haplotype.

According to still another aspect of the present invention there is provided a method of identifying peptides originating from cells participating in the development and/or progression of an autoimmune disease and being capable of binding to MHC molecules of a particular haplotype. The method according to this aspect of the present invention is effected by obtaining cells participating in the development and/or progression of the autoimmune disease and expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype, and identifying peptides originating from proteins participating in the development and/or progression of the autoimmune disease and being capable of binding to MHC molecules of the particular haplotype.

According to another aspect of the present invention there is provided a method of identifying peptides originating from virus infected cells and being capable of binding to MHC molecules of a particular haplotype. The method according to this aspect of the present invention is effected by obtaining virus infected cells expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from the virus and being capable of binding to MHC molecules of the particular haplotype.

According to still another aspect of the present invention there is provided a method of identifying peptides originating from a particular cell type characterized by at least one of the following (i) cell over-expressing at least one protein; (ii) cells characterized by induced mutations; (iii) cells of metastases; (iv) normal or transformed cells expressing cell surface proteins, the peptides being capable of binding to MHC molecules of a particular haplotype. The method according to this aspect of the present invention is effected by obtaining cells of the particular cell type expressing a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from the particular cell type and being capable of binding to MHC molecules of the particular haplotype.

In general, the present invention provides a method of identifying peptides originating from at least one protein of interest or an unknown protein and being capable of binding to MHC molecules of a particular haplotype. The method is effected by obtaining cells co-expressing the at least one protein of interest or unknown protein and a soluble and secreted form of the MHC molecules of the particular haplotype; collecting the soluble and secreted form of the MHC molecules of the particular haplotype; analyzing peptides bound to the soluble and secreted form of the MHC molecules of the particular haplotype; and identifying peptides originating from the at least one protein of interest or unknown protein and being capable of binding to MHC molecules of the particular haplotype. Depending to a great extent on the cell type employed, it will. Once a peptide of an unknown protein is identified, this protein becomes a protein of interest.

The protein of interest or unknown protein can be a native protein expressed by the cells, or the protein of interest can be expressed by the cells following transformation of the cells with nucleic acid encoding for the protein of interest using techniques well known in the art.

The method of the present invention can thus be used to associate proteins of yet unknown pattern of expression with particular tissues or cell types, such as cancer cells. In addition, the method of the present invention can be used to determine whether a specific open reading frame (ORF) is expressed or not in certain cells.

In one preferred embodiment of the present invention the cell type is a cancer cell or a cancer cell line. Primary cell lines, metastatic cell lines, tumor cell lines and normal cell lines which are suitable for implementing the method of the present invention are available, for example, from ATCC. Tables 1 and 2 below provide examples:

TABLE 1

Primary and metastatic cell lines

| Primary Cell Line | | | | Metastatic Cell Line | | |
|---|---|---|---|---|---|---|
| ATCC No. | Name | Disease | Tissue | ATCC No. | Name | Tissue |
| CCL-228 | SW480 | colorectal adenocarcinoma | colon | CCL-227 | SW620 | lymph node |
| CRL-1864 | RF-1 | gastric adenocarcinoma | stomach | CRL-1863 | RF-48 | ascites |
| CRL-1675 | WM-115 | melanoma | skin | CRL-1676 | WM-266-4 | n/a |
| CRL-7425 | Hs 688(A).T | melanoma | skin | CRL-7426 | Hs 688(B).T | lymph node |

TABLE 2

Tumor and normal cell lines

| Tumor Cell Line | | | | Normal Cell Line | | |
|---|---|---|---|---|---|---|
| ATCC No. | Name | Cancer Type | Tissue Source | ATCC No. | Name | Tissue Source |
| CCL-256 | NCI-H2126 | carcinoma; non-small cell lung cancer | lung | CCL-256.1 | NCI-BL2126 | peripheral blood |
| CRL-5868 | NCI-H1395 | adenocarcinoma | lung | CRL-5957 | NCI-BL1395 | peripheral blood |
| CRL-5872 | NCI-H1437 | adenocarcinoma | lung | CRL-5958 | NCI-BL1437 | peripheral blood |
| CRL-5882 | NCI-H1648 | adenocarcinoma | lung | CRL-5954 | NCI-BL1648 | peripheral blood |
| CRL-5911 | NCI-H2009 | adenocarcinoma | lung | CRL-5961 | NCI-BL2009 | peripheral blood |
| CRL-5985 | NCI-H2122 | adenocarcinoma | pleural effusion | CRL-5967 | NCI-BL2122 | peripheral blood |
| CRL-5922 | NCI-H2087 | adenocarcinoma | lymph node (metastasis) | CRL-5965 | NCI-BL2087 | peripheral blood |
| CRL-5886 | NCI-H1672 | carcinoma; classic small cell lung cancer | lung | CRL-5959 | NCI-BL1672 | peripheral blood |
| CRL-5929 | NCI-H2171 | carcinoma; small cell lung cancer | lung | CRL-5869 | NCI-BL2171 | peripheral blood |
| CRL-5931 | NCI-H2195 | carcinoma; small cell lung cancer | lung | CRL-5956 | NCI-BL2195 | peripheral blood |
| CRL-5858 | NCI-H1184 | carcinoma; small cell lung cancer | lymph node (metastasis) | CRL-5949 | NCI-BL1184 | peripheral blood |
| HTB-172 | NCI-H209 | carcinoma; small cell lung cancer | bone marrow (metastasis) | CRL-5948 | NCI-BL209 | peripheral blood |

TABLE 2-continued

Tumor and normal cell lines

| Tumor Cell Line | | | | Normal Cell Line | | |
|---|---|---|---|---|---|---|
| ATCC No. | Name | Cancer Type | Tissue Source | ATCC No. | Name | Tissue Source |
| CRL-5983 | NCI-H2107 | carcinoma, small cell lung cancer | bone marrow (metastasis) | CRL-5966 | NCI-BL2107 | peripheral blood |
| HTB-120 | NCI-H128 | carcinoma; small cell lung cancer | pleural effusion | CRL-5947 | NCI-BL128 | peripheral blood |
| CRL-5915 | NCI-H2052 | mesothelloma | pleural effusion | CRL-5983 | NCI-BL2062 | peripheral blood |
| CRL-5893 | NCI-H1770 | neuroendocrine carcinoma | lymph node (metastasis) | CRL-5960 | NCI-BL1770 | peripheral blood |
| HTB-126 | Hs 578T | ductal carcinoma | mammary gland; breast | HTB-125 | Hs 578Bst | mammary gland; breast |
| CRL-2320 | HCC1008 | ductal carcinoma | mammary gland: breast | CRL-2319 | HCC1007 BL | peripheral blood |
| CRL-2336 | HCC1954 | ductal carcinoma | mammary gland; breast | CRL-2339 | HCC1954 BL | periperal blood |
| CRL-2314 | HCC38 | primary ductal carcinoma | mammary gland; breast | CRL-2346 | HCC38 BL | peripheral blood |
| CRL-2321 | HCC1143 | primary ductal carcinoma | mammary gland: breast | CRL-2362 | HCC1143 BL | peripheral blood |
| CRL-2322 | HCC1187 | primary ductal carcinoma | mammary gland; breast | CRL-2323 | HCC1187 BL | peripheral blood |
| CRL-2324 | HCC1395 | primary ductal carcinoma | mammary gland; breast | CRL-2325 | HCC1395 BL | peripheral blood |
| CRL-2331 | HCC1599 | primary ductal carcinoma | mammary gland, breast | CRL-2332 | HCC1599 BL | peripheral blood |
| CRL-2336 | HCC1937 | primary ductal carcinoma | mammary gland; breast | CRL-2337 | HCC1937 BL | peripheral blood |
| CRL-2340 | HCC2157 | primary ductal carcinoma | mammary gland; breast | CRL-2341 | HCC2157 BL | peripheral blood |
| CRL-2343 | HCC2218 | primary ductal carcinoma | mammary gland; breast | CRL-2363 | HCC2218 BL | peripheral blood |
| CRL-7345 | Hs 574.T | ductal carcinoma | mammary gland; breast | CRL-7346 | Hs 574.Sk | skin |
| CRL-7482 | Hs 742.T | scirrhous adenocarinoma | mammary gland; breast | CRL-7481 | Hs 742.Sk | skin |
| CRL-7303 | Hs 496.T | cancer | mammary gland; breast | CRL-7302 | Hs 496.Sk | skin |
| CRL-7486 | Hs 748.T | cancer | mammary gland, breast | CRL-7486 | Hs 748.Sk | skin |
| CRL-7365 | Hs 605.T | carcinoma | mammary gland; breast | CRL-7364 | Hs 605.Sk | skin |
| CRL-7368 | Hs 606 | carcinoma | mammary gland; breast | CRL-7367 | Hs 606.Sk | skin |
| CRL-1974 | COLO 829 | malignant melanoma | skin | CRL-1980 | COLO 829BL | peripheral blood |
| CRL-7762 | TE 354.T | basal cell carcinoma | skin | CRL-7761 | TE 353.Sk | skin |
| CRL-7690 | Hs 939.T | malignant melanoma | skin | CRL-7689 | Hs 939 Sk | skin |
| CRL-7360 | Hs 600.T | melanoma | skin | CRL-7359 | Hs 600.Sk | skin |
| CRL-7677 | Hs 925.T | pagetoid sarcoma | skin | CRL-7676 | Hs 925 Sk | skin |
| CRL-7672 | Hs 919.T | benign osteold osteoma | bone | CRL-7671 | Hs 919.Sk | skin |
| CRL-7554 | Hs 821 T | giant cell sarcoma | bone | CRL-7553 | Hs 821.Sk | skin |
| CRL-7552 | Hs 820.T | heterophillo osteofication | bone | CRL-7551 | Hs 820.Sk | skin |
| CRL-7444 | Hs 704.T | osteosarcoma | bone | CRL-7443 | Hs 704.Sk | skin |
| CRL-7448 | Hs 707(A).T | osteosarcoma | bone | CRL-7449 | Hs 707(B).Ep | skin |
| CRL-7471 | Hs 735.T | osteosarcoma | bone | CRL-7865 | Hs 735.Sk | skin |
| CRL-7571 | Hs 836.T | osteosarcoma | bone | CRL-7570 | Hs 836.Sk | skin |
| CRL-7595 | Hs 860.T | osteosarcoma | bone | CRL-7519 | Hs 791.Sk | skin |
| CRL-7622 | Hs 888.T | osteosarcoma | bone | CCL-211 | Hs888Lu | lung |
| CRL-7626 | Hs 889.T | osteosarcoma | bone | CRL-7625 | Hs 889.Sk | skin |
| CRL-7628 | Hs 890.T | osteosarcoma | bone | CRL-7627 | Hs 890.Sk | skin |
| CRL-7453 | Hs 709.T | periostitis; granuloma | bone | CRL-7452 | Hs 709.Sk | skin |
| CRL-7432 | Hs 696.T | adenocarcinoma | unknown | CRL-7431 | Hs 696.Sk | skin |
| CRL-7886 | Hs 789.T | transitional cell carcinoma | ureter | CRL-7518 | Hs 789.Sk | skin |
| CRL-7547 | Hs 814.T | giant cell sarcoma | vertebral column | CRL-7546 | Hs 814.Sk | skin |

In another preferred embodiment of the invention, the cell type is a virus infected cell or cell line. Table 3 below provides examples of some known viruses and the diseases they cause:

TABLE 3

| Diseases | Viruses and other pathogens |
| --- | --- |
| African sleeping sickness (African trypanosomiasis) | *Trypanosoma brucei* |
| AIDS | HIV |
| Amebiasis | *Entamoeba histolytica* |
| BSE ("mad cow disease") and nvCJD | |
| Campylobacter infections | Campylobacter |
| Chagas' disease (American trypanosomiasis) | *Trypanosoma cruzi* |
| Cholera | *Vibrio cholerae* |
| Coccidioidomycosis | *Coccidioides immitis* |
| Cryptosporidiosis | Cryptosporidium |
| Cyclosporiasis | Cyclospora |
| Dengue fever | Dengue viruses |
| Diphtheria, tetanus, and pertussis | Toxin-producing strains of *Corynebacterium diphtheriae* |
| Bordetella pertussis | |
| Encophalitis | Japanese encephalitis virus Tickborne encephalitis West Nile viris |
| Filariasis | *Wuchereria bancrofti* and *Brugia malayi* |
| Giardiasis (Giardia infection) | *Giardia intestinalis* |
| Hantavirus pulmonary syndrome | Hantavirus |
| Hepatitis | Hepatitis viruses A, B, C, E |
| Histoplasmosis | *Histoplasma capsulatum* |
| Influenza (flu) | |
| Leishmaniasis | Leishmania |
| Leptospirosis | Leptospira |
| Lyme disease | *B. burgdorferi* sensu stricto, *B. afzelii*, or *B. garinii* |
| Malaria | *Plasmodium falciparum P. vivax P. ovale* and *P. malariae* |
| Measles, mumps, and rubella (MMR) | |
| Meningitis | Haemophilus influenzae type b *Streptococcus pneumoniac* and *Neisseria meningitidis* |
| Onchocerciasis (river blindness) | *Onchocerca volvulus* |
| Plague | *Yersinia pestis* |
| Poliomyelitis | |
| Rabies | Rhabdoviridae, genus Lyssavirus |
| Rocky Mountain spotted fever | |
| Rickettsia | rickettsii |
| severe diarrhea | Rotavirus |
| Salmonellosis | Salmonella |
| Schistosomiasis | |
| Shigellosis | Shigella |
| Tuberculosis (TB) | *Mycobacterium tuberculosis* |
| Typhoid fever | Salmonella serogroup Typhi |
| Typhus fevers | rickettsiae |
| chickenpox | Varicella |
| Vibrio parahaemolyticus | |
| Viral hemorrhagic fevers (e.g., Ebola, Lassa, Marburg, Rift Valley). | arenaviruses, filoviruses, bunyaviruses, and flaviviruses |
| Yellow fever | |

In yet another preferred embodiment of the present invention, the cell type is a cell involved in a development and/or progression of an autoimmune diseases such as T or B cells, and/or an allergic disease or condition, such as mast cells.

In one example, the at least one protein of interest is a tumor associated antigen. The tumor associated antigen can be natively expressed by the cells or can be expressed by appropriately transformed cells. Table 4 below lists some known genes encoding proteins which were identified as tumor associated antigens.

TABLE 4

| Gene Symbol | Gene Name | Locus | Disorders |
| --- | --- | --- | --- |
| ABL1 | v-abl Abelson murine leukemia viral oncogene homolog 1 | 9q34.1 | Leukemia, chronic myeloid |
| ABL2 | v-abl Abelson murine leukemia viral oncogene homolog 2 (arg, Abelson-related gene) | 1q24–q25 | Leukemia, acute myeloid. with eosinophilia |
| AKT2 | v-akt murine thymoma viral oncogene homolog 2 | 19q131–q13.2 | Ovarian carcinoma |
| ARH1 | ras homlog gene family, member I | 1p31 | Ovarian cancer |
| ARP | | 3p21.1 | Pancreatic cancer |
| AXIN2 | axin 2 (conductin, axil) | 17q23–q24 | Colorectal cancer |

TABLE 4-continued

| Gene Symbol | Gene Name | Locus | Disorders |
|---|---|---|---|
| BAX | BCL2-associated X protein | 19q13.3–q13.4 | Colorectal cancer<br>T-cell acute lymphoblastic leukemia |
| BCPR | homeo box B9 | 17p13.3 | Breast cancer |
| BRCA1 | breast cancer 1, early onset | 17q21 | Breast cancer-1<br>Ovarian cancer<br>Breast-ovarian cancer |
| BRCA2 | breast cancer 2, early onset | 13q12.3 | Breast cancer 2, early onset<br>Pancreatic cancer |
| BRCA3 | | 11q23 | Breast cancer-3 |
| BRCA4 | | 13q21 | Breast cancer, type 4 |
| BRCAX | | 13q21 | Breast cancer, type 4 |
| BRCD1 | | 13 | Breast cancer, ductal |
| BRCD2 | | 1p36 | Breast cancer, ductal |
| BUB1 | budding uninhibited by benzimidazoles 1 (yeast homolog) | 2q14 | Colorectal cancer with chromosomal instability |
| CDH1 | cadherin 1, type 1. E-cadherin (epithelial) | 16q22.1 | Endometrial carcinoma<br>Ovarian carcinoma<br>Breast Cancer. |
| CLD | congenital chloride diarrhea | 7q22–q31.1 | Colon cancer<br>Chloride diarrhea, congenital, Finnish type. |
| CSF1R | colony stimulating factor 1 receptor, formerly McDonough feline sarcoma viral (v-fms) oncogene: homolog | 5q33.2–q33.3 | Myeloid malignancy, predisposition to |
| CTNNB1 | catcain (cadherin-associated protein), beta t (88 kD) | 3p22–p21.3 | Colorectal cancer<br>Hepatoblastoma<br>Pilomatricoma |
| CYLD | cylindromatosis (turban tumor syndrome) | 16q12–q13 | Cylindromatosis, familial |
| DCC | deleted in colorectal carcinoma | 18q21.3 | Colorectal cancer |
| DEK | DEK oncogene (DNA binding) | 6p23 | Leukemia, acute nonlymphocytic |
| DLEC1 | deleted in lung and esophageal cancer 1 | 3p22–p21.3 | Lung cancer<br>Esophageal cancer |
| DMBT1 | deleted in malignant brain tumors 1 | 10q25.3–q26.1 | Glioblastoma multiforme<br>Medulloblastoma |
| DRA | down-regulated in adenoma | 7q22–q31.1 | Colon cancer<br>Chloride diarrhea, congenital, Finnish type. |
| ELAC2 | elaC (E coli) homolog 2 | 17p | Prostate cancer, susceptibility to |
| EP300 | E1 A binding protein p300 | 22q13 | Colorectal cancer |
| ESR1 | estrogen receptor 1 | 6q25.1 | Breast cancer<br>Estrogen resistance |
| ETV6 | ets variant gene 6 (TEL oncogene) | 12p13 | Leukemia, acute lymphoblastic |
| FSHR | follicle stimulating hormone receptor | 2p21–p16 | Premature ovarian failure<br>Ovarian sex cord tumors |
| HNPCC7 | 3346 | 15q21.1 | Colorectal cancer, hereditary nonpolyposis, type7 |
| HPC1 | hereditary prostate cancer 1 | 1q24–q25 | Prostate cancer, susceptibility to |
| HPCX | hereditary prostate cancer, X-linked | Xq27–q28 | Prostate cancer, susceptibility to |
| HRAS | v-Ha-ras Harvey rat sarcoma viral oncogene homolog | 11p15.5 | Bladder cancer |
| HRPT2 | hyperparathyroidism 2 (with jaw tumor) | 1q25–q31 | Hyperparathyroidism-jaw tumor syndrome<br>Hyperparathyroidism |
| KAJ1 | kangai 1 (suppression of tumorigenicity 6, prostate: CD82 antigen (R2 leukocyte antigen, antigen detected by monoclonal and antibody IA4)) | 11p11.2 | Prostate cancer, susceptibility to |
| KIT | v-kit Hardy-Zuckerman 4 feline sarcoma viral oncogene homolog | 4q12 | Piebaldism<br>Mast cell leukemia<br>Mastocytosis with associated |
| KRAS1P | v-Ki-ras1 Kirsten rat sarcoma 1 viral oncogene homolog, processed pseudogene | 12p12.1 | Colorectal adenoma<br>Colorectal cancer |
| KRAS2 | v-Ki-ras2 Kirsten rat sarcoma 2 viral oncogene homolog | 12p12.1 | Colorectal adenoma<br>Colorectal cancer |
| LCFS2 | mitochondrial ribosomal protein L13 | 18q11–q12 | ?Lynch cancer family syndrome II |
| LCO | liver cancer oncogene | 2q14–q21 | Heptocellular carcinoma |
| MADH4 | M.A.D (mothers against decapentaplegic, Drosophila) homolog 4 | 18q21.1 | Pancreatic cancer<br>Polyposis, juvenile intestinal |
| MCC | mutated in colorectal cancers | 5q21 | Colorectal cancer |
| MERTK | c-mer proto-oncogene tyrosine kinase | 2q14.1 | Retinitis pigmentosa, MERTK-related |
| MET | met proto-oncogene (hepatocyte growth factor receptor) | 7q31 | Renal cell carcinoma, papillary, familial and sporadic |
| MGCT | | 12q22 | Male germ cell tumor |
| MLH1 | mutL (E. coli) homolog 1 (colon cancer, nonpolyposis type 2) | 3p21.3 | Colorectal cancer, hereditary nonpolyposis, type 2 |
| MPL | myeloproliferative leukemia virus oncogene | 1p34 | Thrombocytopenia, congenital amegakaryncytic |
| MSH2 | mutS (E. coli) homolog 2 (colon cancer, nonpolyposis type 1) | 2p22–p21 | Colorectal cancer, hereditary nonpolyposis, type 1 |

TABLE 4-continued

| Gene Symbol | Gene Name | Locus | Disorders |
|---|---|---|---|
| MSH6 | mutS (*E coli*) homolog 6 | 2p16 | Cancer susceptibility<br>Endometrial carcinoma<br>Colorectal |
| MTACR1 | multiple tumor-associated chromosome region 1 | 11p15.5 | Wilms tumor, type 2<br>Adrenocortical carcinoma, hereditary, 202300 |
| MYC | v-myc avian myelocytomatosis viral oncogene homolog | 8q24.12–q24.13 | Burkitt lymphoma |
| NRAS | neuroblastoma RAS viral (v-ras) oncogene homolog | 1p13.2 | Colorectal cancer |
| PCAP | predisposing for prostate cancer | 1q42.2–q43 | Prostate cancer, susceptibility to |
| PCBC | 347S | 1p36 | Prostate cancer, susceptibility to |
| PDGFB | platelet-derived growth factor beta polypeptide (simian sarcoma viral (v-sis) oncogene homolog) | 22q12.3–q13.1 | Meningioma, SIS-related<br>Dermatofibrosarcoma protuberans |
| PDGFRL | platelet-derived growth factor receptor-like | 8p22–p21.3 | Hepatocellular cancer<br>Colorectal cancer |
| PGL2 | paraganglioma or familial glomus tumors 2 | 11q13.1 | Paraganglioma, familial nonchromaffin |
| PGL3 | paraganglioma or familial glomus tumors 3 | 1q21 | ∴Paragangliomas, familial nonchromaffin, 3 |
| PHB | prohibitin | 17q21 | Breast cancer, sporadic |
| PIK3CA | phosphoinositide-3-kinase, catalytic, alpha polypeptide | 3q26.3 | Ovarian cancer |
| PMS1 | postmeiotic segregation increased (*S. cerevisiae*) 1 | 2q31–q33 | Colorectal cancer, hereditary nonpolyposis, type 3 |
| PMS2 | postmeiotic segregation increased (*S. cerevisiac*) 2 | 7p22 | Turcot syndrome with glioblistoma<br>Colorectal cancer, |
| PPP2R1B | protein phosphatase 2 (formerly 2A), regulatory subunit A (PR 65), beta isoform | 11q22–q24 | Lung cancer |
| PRCA1 | prostate cancer 1 | 1q24–q25 | Prostate cancer, susceptibility to |
| PRKCA | protein kinase C, alpha | 17q22–q23.2 | Pituitary tumor, invasive |
| PTEN | phosphatase and tensin homolog (mutated in multiple advanced cancers 1 ) | 10q23.3 | Cowden disease<br>Lhermitte-Duclos syndrome |
| PTPN12 | protein tyrosine phosphatase, non-receptor type 12 | 7q11.23 | Colon cancer |
| RAB27A | RAB27A, member RAS oncogene family | 15q21 | Griacelli syndrome |
| RAD51 | RAD51 (*S cerevisiae*) homolog (*E coli* RecA homolog) | 15q15.1 | Breast cancer, susceptibility to |
| RAD54L | RAD54 (*S. cerevisiae*)-like | 1p32 | Lymphoma, non-Hodgkin<br>Breast cancer, invasive intraductal |
| RB1 | retinoblastoma 1 (including osteosarcoma) | 13q14.1–q14.2 | Retinoblastoma<br>Osteosarcoma<br>Bladder cancer, |
| RET | ret proto-oncogene (multiple endocrine neoplasin and medullary thyroid carcinoma 1, Hirschsprung disease) | 10q11.2 | Multiple endocrine neoplasin IIA<br>Medullary thyroid |
| RUNX1 | runt-relatad transcription factor 1 (acute myeloid leukemia 1; aml1 oncogene) | 21q22.3 | Leukemia, acute myeloid<br>Platelet disorder, familial, with |
| SCLC1 | 354 | 3p23–p21 | Small-cell cancer of lung |
| SLC22AIL | solute carrier family 22 (organic cation transporter), member 1-like | 11p15.5 | Breast cancer<br>Rhabdomyosarcoma<br>Lung |
| SLC26A3 | solute carrier family 26, member 3 | 7q22–q31.1 | Colon cancer<br>Chloride diarrhea, congenital, Finnish type |
| SMARCB1 | SWI/SNF related, matrix associated, actin dependent regulator of chromatin, subfamily b, member 1 | 22q11 | Rhabdoid tumors<br>Rhabdoid predisposition syndrome, familial |
| SRC | v-src avian sarcoma (Schmidt-Ruppin A-2) viral oncogene homolog | 20q12–q13 | Colon cancer, advanced |
| SSTR2 | somatostatin receptor 2 | 17q24 | Lung cancer, small cell |
| ST11 | suppression of tumorigenicity 11 (pancreas) | 3p25 | Pancreatic endocrine tumors |
| ST12 | suppression of tumorigenicity 12 (prostate) | 10pter-q11 | Prostate adenocarcinoma |
| ST3 | suppression of tumorigenicity 3 | 11q13 | Cervical carcinoma |
| ST8 | suppression of tumorigenicity 8 (ovarian) | 6q26–q27 | Ovarian cancer, serous |
| TACSTD2 | tumor-associated calcium signal transducer 2 | 1p32–q12 | Corneal dystrophy, gelatinous drop-like |
| TCF7L2 | transcription factor 7-like 2 (T-cell specific. HMG-box) | 10q25.3 | Colorectal cancer |
| TGFBR2 | transforming growth factor, beta receptor II (70–80 kD) | 3p22 | Colon cancer<br>Colorectal cancer, hereditary nonpolyposis, type 6 |
| THPO | thrombopoietin (myeloproliterative leukemia virus oncogene ligand, megakaryocytegrowth and development factor) | 3q26.3–q27 | Thrombocythemia, essential |
| TNFRSF10B | tumor necrosis factor receptor superfamily. member 10b | 8p22–p21 | Squamous cell carcinoma, head and neck |
| TNFRSF11A | tumor necrosis factor receptor super-family, member 11a, activator of NFKB | 18q22.1 | Osteolysis, familial expansile<br>Pager disease of bone, |
| TNFRSF1A | tumor necrosis factor receptor superfamily, member 1A | 12p13.2 | Periodic fever, familial |

TABLE 4-continued

| Gene Symbol | Gene Name | Locus | Disorders |
|---|---|---|---|
| TNFRSF6 | tumor necrosis factor receptor superfamily, member 6 | 10q24.1 | Autoimmune lymphoprolferative syndrome |
| TNFSF5 | tumor necrosis factor (ligand) superfamily, member S (hyper-IgM syndrome) | Xq26 | Immunodefieiency, X-linked, with hyper-IgM |
| TNFSF6 | tumor necrosis factor (ligand) superfamily, member 6 | 1q23 | Systemic lupus erythrrmatosus, susceptibility to |
| TNF | tumor necrosis factor (TNF superfamily, member 2) | 6p21.3 | Malaria, cerebral, susceptibility to Septic shock |
| TOC | tylosis with oasophageal cancer | 17q24 | Tylosis with esophageal cancer |
| TP53 | tumor protein p53 (Li-Fraumeni syndrome) | 17p13.1 | Colorectal cancer Li-Fraumeni syndrome |
| TP73 | tumor protein p73 | 1p36 | Neuroblastoma |
| TSG101 | tumor susceptibility gene 101 | 11p15.2–p15.1 | Breast cancer |
| VMGLOM | venous malformation with glomus cells | 1p22–p21 | Glomus tumors, multiple |
| WT1 | Wilms tumor 1 | 11p13 | Wilms tumor, type 1 Denys-Drash syndrome Frasier |
| WT2 | Wilms tumor 2 | 11p15.5 | Wilms tumor, type 2 Adrenocortical carcinoma, hereditary |

In another example, the at least one protein of interest includes a cytokine. Many diseases, including neurodegenerative (e.g., Alzheimer's disease) and autoimmune (e.g., rheumatoid arthritis, multiple sclerosis and the like) diseases are caused or accompanied by inflammation, resulting in infiltration of leukocytes into the inflicted tissue(s). In these diseases proinflammatory cytokines and chemokines are believed to play a pivotal role in the attraction of leukocytes to the site of inflammation and in the initiation and progression of the inflammatory process. In rheumatoid arthritis, for example, the role of proinflammatory cytokines, particularly TNF-o and IL-1, in disease manifestation has been intensively studied and explored in experimental models that have been expanded to clinical trials. Other cytokines such as IL-4, TGF-β, IL-8, IL-17, IL-10, IL-11, IL-12 and IL-15 have also been implicated in the regulation of rheumatoid arthritis. Such regulation can be attributed to either their direct effect on disease manifestation, their synergistic effect with other proinflammatory cytokines/chemokines, or their involvement in the regulation of chemokine transcription, and production.

Chemokines are chemoattractant cytokines that mediate leukocyte attraction and recruitment at the site of inflammation. Based on the positions of the first two cysteines, chemokines can be divided into four highly conserved but distinct supergene families, C—C, C—X—C, C and C—X3—C. The C—C family is primarily involved in the activation of endothelium and chemoattraction of T cells and monocytes to the site of inflammation. The protective competence of anti-C—C chemokine based immunotherapy has been demonstrated in experimental autoimmune encephalomyelitis (EAE), and rheumatoid arthritis.

Neutralizing the activity of chemokines as a way to treat various diseases has been explored by many researchers. For example, in a recent study neutralizing antibodies to epithelial neutrophil activating peptide 78 (ENA-78) were found capable of inhibiting the development of AA if administered before but not after the onset of disease [92]. In another recent study, Barnes et al. [93] used anti-human RANTES to ameliorate AA in the Lewis rat. Gong et al. [94] used an antagonist of Monocyte Chemoattractant Protein 1 (MCP-1) to inhibit arthritis in the MRL-1 pr mouse model. Using a streptococcal cell wall induced arthritis model it has been shown that anti-IL-4 and anti MCP-1 antibodies block the disease [95]. The same study demonstrated that neutralizing IL-4 by itself, leads to a marked reduction in MCP-1 mRNA transcription at the autoimmune site and to inhibition of the development of disease which further implicates MCP-1 in playing an active role in arthritis development.

In yet another example, the at least one protein of interest includes a protein, e.g., a surface protein, of a pathogen, such as a viral pathogen, a bacterial pathogen or a parasite (either mono or multicellular parasite).

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

Major histocompatibility complex (MHC) class I molecules are expressed on the surface of nearly all cells. These molecules function in presenting peptides which are mainly derived from endogenously synthesized proteins to CD8+ T cells via an interaction with the oβ T-cell receptor. The class I MHC molecule is a heterodimer composed of a 46-kDa heavy chain which is non-covalently associated with the 12-kDa light chain β-2 microglobulin. Class I MHC-restricted peptides, which are traditionally assumed to be 8-10-amino acid-long, bind to the heavy chain o1-o2 groove via two or three anchor residues that interact with corresponding binding pockets in the MHC molecule. The β-2 microglobulin chain plays an important role in MHC class I intracellular transport, peptide binding, and conformational stability [76]. For most class I molecules, the formation of a heterodimer consisting of the MHC class I heavy chain, peptide (self or antigenic) and β-2 microglobulin is required for biosynthetic maturation and cell-surface expression [76].

Research studies performed on peptide binding to class I MHC molecules enable to define specific MHC motifs functional in displaying peptides derived from viral or tumor antigens that are potentially immunogenic and might elicit specific response from cytotoxic T lymphocytes (CTLs) [77,78].

Soluble MHC multimers posses a high avidity for T-cells since they provide multi-point binding of TCRs with their MHC-peptide ligands. As such, multimeric forms (tetramers) of MHC-peptide complexes have been the center of much interest recently, because they can be used for direct phenotypic characterization of T cell responses in normal as well as pathological conditions, thus, providing insight into the pathopysiology and mechanisms of various diseases. Recombinant soluble and secreted MHC class I and class II complexes including single chain MHC are described in [79–91] which are incorporated herein by references.

There are several thousands of MHC genes, some of which were cloned. Table 5 below associates the MHC genes into classes and types (6). The sequences of the known MHC genes can be found in the Kabat database (http://immuno.bme.nwu.edu/).

TABLE 5

|  | Type | Number of genes |
|---|---|---|
| MHC Class I | A, B, C | 1014 |
| MHC class IIA chain | DR DQ DP | 348 |
| MHC class IIB chain | DR DQ DP | 1680 |

Genes encoding MHC of particular haplotypes can be readily isolated using techniques well known in the art and reconstructed to encode soluble MHC molecules essentially as exemplified in the Examples section that follows. Such well known techniques include, for example, PCR amplification, enzymatic digestion and ligation.

According to a presently preferred embodiment of the present invention analyzing the peptides bound to the soluble and secreted form of the MHC molecules of the particular haplotype is by mass spectrometry, mass charge ratio and collision induced disintegration. Edman degradation can also be employed in certain cases where a sufficient amount of the pure peptide becomes available.

The identification of the amino acid sequence of a peptide in accordance with the teachings of the present invention is preferably effected by comparison of the data collected by mass spectrometry, mass charge ratio and collision induced disintegration to putative data of mass spectrometry, mass charge ratio and collision induced disintegration of known proteins.

As used herein in the specification and in the claims section below the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, or more immunogenic.

Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein. Further detail in this respect are provided hereinunder.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids useful in MHC class I, type A2, recognizable peptide antigens are given hereinunder. Other anchor residues are known for other MHC molecules.

Thus, assume the following positions (P1-P9) in a 9-mer peptide:

P1-P2-P3-P4-P5-P6-P7-P8-P9

The P2 and P9 positions include the anchor residues which are the main residues participating in binding to A2 MHC molecules. Amino acid resides engaging positions P2 and P9 are hydrophilic aliphatic non-charged natural amino (examples being Ala, Val, Leu, Ile, Gln, Thr, Ser, Cys, preferably Val and Leu) or of a non-natural hydrophilic aliphatic non-charged amino acid (examples being norleucine (Nle), norvaline (Nva), o-aminobutyric acid). Positions P1 and P3 are also known to include amino acid residues which participate or assist in binding to MHC molecules, however, these positions can include any amino acids, natural or non-natural. The other positions are engaged by amino acid residues which typically do not participate in binding, rather these amino acids are presented to the immune cells. Further details relating to the binding of peptides to MHC molecules can be found in reference 117, see Table V thereof, in particular.

Hydrophilic aliphatic natural amino acids at P2 and P9 can be substituted by synthetic amino acids, preferably Nleu, Nval and/or o-aminobutyric acid. P9 can be also substituted by aliphatic amino acids of the general formula —HN($CH_2$)$_n$COOH, wherein n=3–5, as well as by branched derivatives thereof, such as, but not limited to,

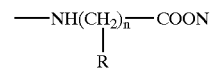

wherein R is, for example, methyl, ethyl or propyl, located at any one or more of the n carbons.

The amino terminal residue (position P1) can be substituted by positively charged aliphatic carboxylic acids, such as, but not limited to, $H_2N(CH_2)_n COOH$, wherein n=2–4 and $H_2N$—C(NH)—NH($CH_2$)$_n$COOH, wherein n=2–3, as well as by hydroxy Lysine, N-methyl Lysine or ornithine (Orn). Additionally, the amino terminal residue can be substituted by enlarged aromatic residues, such as, but not limited to, $H_2N$—($C_6H_6$)—$CH_2$—COOH, p-aminophenyl alanine, $H_2N$—F(NH)—NH—($C_6H_6$)—$CH_2$—COOH, p-guanidinophenyl alanine or pyridinoalanine (Pal). These latter residues may form hydrogen bonding with the OH⁻ moieties of the Tyrosine residues at the MHC-1 N-terminal binding pocket, as well as to create, at the same time aromatic-aromatic interactions.

Derivatization of amino acid residues at positions P4-P8, should these residues have a side-chain, such as, OH, SH or $NH_2$, like Ser, Tyr, Lys, Cys or Orn, can be by alkyl, aryl, alkanoyl or aroyl. In addition, OH groups at these positions may also be derivatized by phosphorylation and/or glycosylation. These derivatizations have been shown in some cases to enhance the binding to the T cell receptor.

Longer derivatives in which the second anchor amino acid is at position P10 may include at P9 most L amino acids. In some cases shorter derivatives are also applicable, in which the C terminal acid serves as the second anchor residue.

Cyclic amino acid derivatives can engage position P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2)_n$—COOH)—C(R)H—COOH or H—N(($CH_2)_n$—COOH)—C(R)H—$NH_2$, wherein n=1–4, and further wherein R is any natural or non-natural side chain of an amino acid. As stated above, the data presented herein relates to the residues of the most abandoned MHC molecule—MHC class I, type A2. This data was collected over the years via the detailed analysis of thousands of peptides that bind to MHC-I, A2. It will be appreciated that the method of the present invention allows the collection of data and analysis of peptides that bind any other to MHC molecule.

Cyclization via formation of S—S bonds through incorporation of two Cys residues is also possible. Additional side-chain to side chain cyclization can be obtained via formation of an interaction bond of the formula —($CH_2$—$)_n$—S—$CH_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted by N-methylated bonds (—N($CH_3$)—CO—), ester bonds (—C(R)H—C—O—O—C(R)—N—), ketomethylen bonds (—CO—$CH_2$—), o-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2–3) at the same time. Preferably, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Tables 6–7 below list all of the naturally occurring amino acids (Table 6) and some of the non-conventional or modified amino acids (Table 7).

TABLE 6

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | 0 |
| Glutamic Acid | Glu | E |
| Glycine | Gly | G |
| Histidine | His | H |
| Isoleucine | Tie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 7

| Non-conventional ammo acid | Code | Non-conventional ammo acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methythistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methyinorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methyltlireonine | Nmthr |
| D-methionine | Dmet | L-N-methyltryptophan | Nmtrp |
| D-ornithine | Dora | L-N-methyltyrosine | Nmtyr |
| D-phenylalanine | Dphe | L-N-methylvaline | Nmval |
| D-proline | Dpro | L-N-methylethylglycine | Nmetg |

TABLE 7-continued

| Non-conventional amino acid | Code | Non-conventional amino acid | Code |
|---|---|---|---|
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-mertiylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Denser | N-cyctobutylglycine | Nebut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-rnethylalnine | Dmnala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nrochexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | K-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methyltbioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pea |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mb is | L-α-methylhomophenylalanine | Mhphe |

TABLE 7-continued

| Non-conventional ammo acid | Code | Non-conventional ammo acid | Code |
|---|---|---|---|
| L-α-methylisoleucine | Mile | N-(2-methylthioethyl)glycine | Nmot |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreoninie | Mthr |
| L-α-methylvaline | Mtrp | L-α-methyltyrosine | Mtyr |
| L-α-methylleucine | Mval Nnblim | L-N-methylhomophenylalaninie | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

A peptide according to the present invention can be used in a self standing form or be a part of a larger moiety such as a protein or a display moieties such as a display bacterium, a display phage or preferably a display cell.

Additionally, a peptide according to the present invention includes at least five, optionally at least six, optionally at least seven, optionally at least eight, optionally at least nine, optionally at least ten, optionally at least eleven, optionally at least twelve, optionally at least thirteen, optionally at least fourteen, optionally at least fifteen, optionally at least sixteen or optionally at least seventeen, optionally between seventeen and twenty five or optionally between twenty five and at least thirty amino acid residues (also referred to herein interchangeably as amino acids).

Accordingly, as used herein the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

As used herein the phrase "derived from a protein" refers to peptides derived from the specified protein or proteins and further to homologous peptides derived from equivalent regions of proteins homologous to the specified proteins of the same or other species, provided that these peptides are effective as vaccines, such as anti-tumor vaccines. The term further relates to permissible amino acid alterations and peptidomimetics designed based on the amino acid sequence of the specified proteins or their homologous proteins.

As used herein the phrase "anti-tumor vaccines" refers to a vaccines effective in preventing the development of, or curing, cancer, including primary tumor and/or metastases.

The peptides of the invention can be administered per se or as an active ingredient in a pharmaceutical composition which may further include a pharmaceutically acceptable carrier. Preferably, one or more peptides of the invention are presented in context of an antigen presenting cell. The most common cells used to load antigens are bone marrow and peripheral blood derived dendritic cells (DC), as these cells express costimulatory molecules that help activation of CTL. Nevertheless, the peptide presenting cell can also be a macrophage, a B cell or a fibroblast. Presenting the peptide can be effected by a variety of methods, such as, but not limited to, (a) transforming the presenting cell with at least one polynucleotide (e.g., DNA) encoding at least one peptide; (b) loading the presenting cell with at least one polynucleotide (e.g., RNA) encoding at least one peptide; (c) loading the presenting cell with at least one peptide (e.g., synthetic peptide); and (d) loading the antigen presenting cell with at least one longer polypeptide (e.g., purified) including at least one peptide. Loading can be external or internal. The polynucleotide, peptide or longer polypeptide can be fused to internalizing sequences, antennapedia sequences or toxoid sequences or to helper sequences, such as, but not limited to, heat shock protein sequences.

As used herein a "pharmaceutical composition" refers to a preparation of one or more of the peptides described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of lactic acid.

In this respect, it should be pointed out that some of the peptides of the present invention, according to preferred embodiments, are readily soluble in aqueous media and are therefore easily formulated.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the peptides of the invention may be formulated in aqueous solutions, preferably in physiologically compatible buffers such as Hank's solution, Ringer's solution, or physiological saline buffer with or without organic solvents such as propylene glycol, polyethylene glycol and the like. For transmucosal administration, penetrants are used in the formulation. Such penetrants are generally known in the art.

For oral administration, the peptides can be formulated readily by combining the active compounds with pharmaceutically acceptable carriers well known in the art. Such carriers enable the peptides of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as aqueous solution, fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the peptides are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The peptides described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the peptides to allow for the preparation of highly concentrated solutions.

Alternatively, the active ingredient may be in powder form for constitution with a suitable vehicle, e.g., sterile, pyrogen-free water, before use.

The peptides of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of peptide effective to prevent, alleviate or ameliorate symptoms of pathology or prolong the survival of the subject being treated.

Determination of a therapeutically effective amount is well within the capability of those skilled in the art, especially in light of the detailed disclosure provided herein.

For any peptide used in the methods of the invention, the therapeutically effective amount or dose can be estimated initially from activity assays in cell cultures and/or animals. For example, a dose can be formulated in animal models to achieve a circulating concentration range that includes the IC50 as determined by activity assays (e.g., the concentration of the test compound, which achieves a half-maximal inhibition of the proliferation activity). Such information can be used to more accurately determine useful doses in humans.

Toxicity and therapeutic efficacy of the peptides described herein can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50–90% inhibition of a proliferation of certain cells may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10–90% of the time, preferable between 30–90% and most preferably 50–90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as a U.S. Food and Drug Administration (FDA) approved kit, which may contain one or more unit dosage forms containing the active ingredient. The pack may, for example, comprise metal or plastic foil, such as a blister pack. The pack or dispenser device may be accompanied by instructions for administration, The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a chemical conjugate of the invention formulated in a compatible pharmaceutical carrier may also be prepared, placed in an appropriate container, and labeled for treatment of an indicated condition, such as a cancer of a certain type, an autoimmune disease or an allergy.

Peptides of the present invention may be packaged in kits, each such kit comprising a plurality of individual containers, each of which containing at least one peptide identified by the method of the present invention. Such a kit can be used for two purposes. First, an in vitro functional assay, such as the CTL assay [20] or the ELISPOT assay [19] of, for example, cytokine (e.g., IL-2, TNF alpha or interferon gamma) production or development of cytotoxiciy using immune cells derived from a patient can be used to determine the immune response of the patient to each one of the peptides, which response to a large extent depends on the particular MHC haplotype of the patient. Second, once, a reactive peptide or peptides are identified, either by an individualized in vitro assay or from in silico data as is further detailed below, suitable peptide or peptides from the kit can be administered so as to treat the patient.

According to another aspect of the present invention there is provided an electronic data storage device, storing, in a retrievable form, a plurality of sequences of peptides identified by the method described herein. Various other parameters, such as the parameters identified in the Tables provided in the Examples section that follows, can also be linked to the peptide sequences, in, for example, a table form or any other form. Preferably, the plurality of peptides are arranged at least according to their association with a pathology and further according to their ability of binding to MHC molecules of a particular haplotype. This in silico data can be used instead or in addition to the in vitro assays described above to match a most active peptide to treat a pathology of a certain patient having a particular pre identified MHC haplotype. Thus, look up tables associating a peptide with a protein with a gene, with a disease with a haplotype, and/or with an efficiency score can be constructed and used to best suit a peptide for treatment of a disease in an individualized way taking into account the MHC haplotype of the patient to be treated. Of course, individualized in vitro assays can be used to ascertain peptide selection.

The electronic data storage device can, for example, be an electromagnetically or electro-optically readable device and it preferably forms a part of a server that is accessible by users through a communications network, such as the Internet, an intranet or an extranet, via a plurality of user clients at the disposal of the users. A management software application manages the data stored in the data storage device and is preferably designed to support search and retrieval of information from the database and deposition of information into the database.

Thus, further according to the present invention there is provided a method of eliciting an immune response against a protein of interest in a subject having a particular MHC haplotype. The method according to this aspect of the invention is effected by determining the subject's particular MHC haplotype; and administering to the subject an effective amount of at least one peptide derived from the protein of interest and which is capable of binding to MHC molecules of the particular haplotype.

Still further according to the present invention there is provided a method of eliciting an immune response against a protein of interest in a subject. The method is effected by using an individualized in vitro assay for determining an immune reactivity of an immune system of the subject to a plurality of peptides derived from the protein of interest; and administering to the subject an effective amount of at least one peptide derived from the protein of interest and which is capable of inducing predetermined sufficient immune reactivity.

According to another aspect the present invention provides a method of treating a pathology by eliciting an immune response against a protein of interest in a subject having a particular MHC haplotype. The method is effected by determining the subject's particular MHC haplotype; and administering to the subject a therapeutic effective amount of at least one peptide derived from the protein of interest and which is capable of binding to MHC molecules of the particular haplotype.

As used herein the term "treating" includes prevention or cure of a pathology, such as a disease, syndrom or manifestation, effected by inhibiting, slowing or reversing the progression of the disease, syndrom or manifestation, substantially ameliorating clinical symptoms of a disease, syndrom or manifestation or substantially preventing the appearance of clinical symptoms of a disease, syndrom or manifestation.

As used herein the term "subject" refers to humans and animals having an MHC system, such as the HLA system in humans, in particular farm animals. It will be appreciated in this respect that the method of the present invention can be used to improve all kinds of peptide immunization via individualization for both human beings and animals.

A variety of pathologies can be treated using the peptides of the present invention, including, but not limited to, cancers, infections, inflammations, autoimmune diseases, allergies, etc. The gist of the present invention with respect to treating pathologies lies in the fact that the present invention offers, for the first time, individualization of the vaccine to the MHC haplotype of the treated subject.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,353,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL PROCEDURES

Cell Lines:

The human cancer cell lines: PC3 (prostate cancer), UCI-107 and UCI-101 (both ovarian cancer), MDA-231 and MCF-7 (both breast cancer) were obtained from the ATCC. The human B-cell line C1R was a generous gift from Nick Zavazava. UCI-107, UCI-101, MDA-231 and MCF7 cells were maintained in DMEM containing 10% FCS, 1 mM glutamine, 0.1 mg/ml streptomycin and 100 units/ml penicillin. PC3 and C1R cells were maintained in RPMI 1640 containing 10% FCS, 1 mM glutamine, 0.1 mg/ml streptomycin and 100 units/ml penicillin. For growing MCF-7 cells without estrogen, the cells were maintained in DMEM without sodium pyruvate and phenol red and containing 4% FCS stripped of estrogen, 1 mM glutamine, 0.1 mg/ml streptomycin and 100 units/ml penicillin. Culture media, and serum were obtained from GibcoBRL.

RMA-S-HHD is a murine TAP-2 deficient lymphoma clone of C57BL/6 origin, transfected with HLA-A2.1/Db-β2 m single chain (HHD) [23]. The RMA-S-HHD-B7.1 cells transfected by the murine B7.1 costimulatory molecule (CD80). EL4-HHD is the murine lymphoma cell line EL4 transfected by HHD. RMA-S-HHD, RMA-S-HHD-B71 and EL4-HHD were maintained in RPMI 1640 containing 10% FCS and 1 mM glutamine, 0.1 mg/ml streptomycin and 100 units/ml penicillin. After transfection, the cells were maintained in medium supplemented with 500 to 1000 µg/ml of the antibiotic G418 (GibcoBRL).

DNA:

Plasmid HLA-A2/Q10$^b$, used for expression of soluble MHC, contains the first five exons of the HLA-A2 fused to exons 5 to 8 of the murine mutant Q10$^b$, which lacks a functional transmembrane domain and is therefore secreted. This plasmid was a generous gift from D. Margulies, of the NIH [24]. Plasmid (phβ2 m) was constructed to express the human β2-microglobulin. It is based on the cDNA of human β2 m (hβ2 m) isolated from PC3 cells and amplified by PCR using the following primers: 5'-sense primer: 5'-AGATTCCCAAGCTTATGTCTCGCTCCGTGG-3' (SEQ ID NO:40) contained a restriction site for Hind III before the signal peptide and a 3' antisense primer 5'-AGCTAGTCTAGATTATCACATGTCTC GATCCCACTTAAC-3' (SEQ ID NO:41) contained the restriction site for XbaI on the 3' end of β2 m. The purified PCR product was cut with HindIII and XbaI and ligated into the eukaryotic expression vector pCDNA-3.1 (Invitrogen). Plasmid sHLA-A2 and sHLA-B7 contains the cDNA of the first 4 exons of this alleles ligated into the plasmid pcDNA3.1 [34].

Antibodies and Hybridomas

The hybridomas W6/32 and BB7.2, an anti-MHC class-I and anti-HLA-A2 respectively, and HB-149 an anti β2 m were obtained from the ATCC. The antibodies were affinity purified using protein A-Sepharose CL-4B (Sigma) from mouse ascites fluid.

Transfection of Cancer Cells and Selection of Clones Secreting sMHC:

Cell lines were co-transfected with plasmid HLA-A2/Q10$^b$ and with phβ2 m, which conferred resistance to the antibiotic G418 or transfected only with the plasmids sHLA-A2 and sHLA-B7 that contained the antibiotic resistance. Cells were electroporated by use of a Gene Pulser (Bio-Rad) set at 280–300 mV 960 µF. Transfected cell clones were selected in G418 antibiotic and screened for those secreting sMHC to the growth medium. Secretion of sMHC was assayed by sandwich-ELISA with plates coated with the mAb BB7.2 (for sMHC-A2) or by HB-149 (for sMHC-B7) and sMHC was detected with the biotinilated mAb W6/32. Color was developed with ABTS (Sigma) catalyzed by streptavidin peroxidase (Sigma).

Affinity Purification of Soluble MHC

Cultured cells, expressing the soluble MHC were grown to confluency in 150 mm plates. The culture medium was collected and residual cells were removed by centrifugation. Soluble MHC molecules were purified from the cleared culture medium by affinity chromatography on W6/32 antibody columns at 4° C. The antibodies were coupled to NHS-activated agarose (Pharmacia) or to protein A Sepharose (Sigma) with n-methylpipelimidate (Sigma). The columns were washed with 0.5 M NaCl, 20 mM, Tris pH 8. The MHC molecules were eluted from the column with 0.1 M acetic acid at pH 3. Peptides were separated from the MHC complexes by boiling for five minutes in 10% acetic acid followed by ultra-filtration through a 3 kDa Microcon (Amincon) [2].

Synthetic Peptides

Peptides were synthesized on AbiMed AMS 422 multiple peptide synthesizer (Abimed, Langenfeld, Germany) by Fmoc chemistry, precipitated with ether and used with or without further purification (HPLC).

Peptides Separation and Analysis

The MHC bound peptides were resolved by reverse-phase HPLC on a 0.1 ID fused silica capillaries with length of about 30 cm (J&W) slurry packed with POROS 10 R2 (PerSepetive Biosystems). The capillaries were fitted with electrospray needle made from 36-gauge stainless tubing (Small Parts Inc. Miami Lakes, Fla.). A Rheodyne 9125 HPLC injector fitted with a 20 µl loop was used for loading the column. The peptides were resolved by a relatively long (90 minutes) linear gradient of 5 to 50% acetonitrile with 0.1% acetic acid, at a flow rate of about 1 µl/minute. The flow was electrosprayed directly from the HPLC column into an ion trap mass spectrometer (LCQ, Finnigan). The mass spectrometry analysis was done in the positive ion mode, using repetitively a full MS scan usually between 450 to 1500 atomic mass units (amu) followed by collision-induced decomposition (CID) of the dominant ion selected from the previous MS scan. In some cases the full MS was performed with a narrower mass range to reduce the number of detected peptides. The peptides were identified by comparing their MS and CID data to the calculated MS and CID of the proteins in the Genpept databank (www.ncbi.nlm.nih.gov/genpept) using the Sequest software [25] (obtained from Finnigan, San Jose, Calif.). The number of times each peptide was fragmented by CID was usually limited to two by dynamic exclusion, a feature of the Xcalibur control software the LCQ mass spectrometer (Finnigan).

Stabilization of Cell Surface HLA-2.1 by Peptide Binding:

RMA-S-HHD cells were washed three times with PBS followed by incubation overnight in FCS-free IMDM medium at 26° C. Synthetic peptides were added to $10^6$ cells at a concentration of 100 µM. The cells were incubated for two hours at 26° C. followed by two hours at 37° C. The stabilization of the HHD MHC by the peptides binding was measured by FACS analysis on Becton Dickinson FACStar flow cytometer after decorating the cells with W6/32 mAb at 4° C. for one hour and then 30 min incubation with anti-mouse FITC at 4° C. (Sigma).

Cytotoxic T Lymphocytes Assays:

Transgenic mice expressing a single chain HLA-A2.1/ Db-β2 m which are double knockout for H-2 Db and for β2 m (HHD mice) [23] were immunized four times intraperitoneally at 7-day interval with $2\times10^6$ irradiated (5,000 rad) RMA-S-HHD-B7.1 cells loaded for two hours at 26° C. followed by two hours at 37° C. with 100 µM of the synthetic peptides. Ten days after the last immunization the spleens were removed from the vaccinated mice. Splenocytes were re-stimulated with 100 µM of synthetic peptides for five days. Viable lymphocytes were separated by lympholyte-M (Cadarlane, Hornby, Canada) and resuspended in RPMI-HEPES. Cytotoxic activity was measured as in [26] by admixing the lymphocytes at different ratios with $5\times10^3$ EL4-HHD cells grown in medium containing $^{35}$S methionine and then loaded wit the synthetic peptides.

EXPERIMENTAL RESULTS

In order to identity large number of MHC bound peptide antigens presented in the context of a particular MEC haplotype, different human cell lines were transfected with expression vectors for soluble, secreted MHC molecules. Indeed, different soluble MHC could be transfected into various cell lines resulting in enabling the recovery of large amounts of the soluble MHC molecules from the cell's growth medium. The sMHC molecules were recovered with their authentic patterns of peptides still bound and free of contamination by cellular debris and detergents. Prostate (PC3), ovarian (UCI-107) and breast (MDA-231 and MCF-7) cell lines were transfected with the DNA coding HLA-A2.1/Q10$^b$, or sMHC-A2 and sMHC-B7. Soluble MHC molecules were recovered from the culture medium without disrupting the cells and the sMHC molecules were purified by a single step of immunoaffinity chromatography. About 200 µg of the sMHC molecules were recovered from about $10^9$ cells (FIGS. 1A–C). The MHC large subunit, the β2 m and small amounts of antibodies that were released from the immunoaffinity column by the acid treatment were the only proteins detected in the column eluant. The peptides were separated from the proteins subunits of the MHC by ultra-filtration. The recovered heavy subunit of the soluble MHC molecules was confirmed to be that of HLA-A2.1 by peptide mapping and by micro sequencing.

Figure 2A:
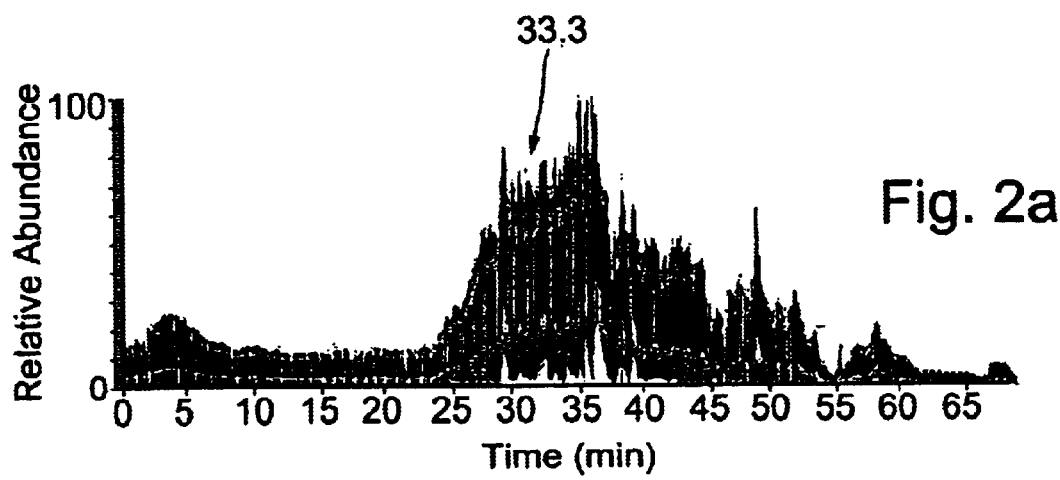
FIGS. 2A–C show a typical nano-capillary reversed-phase chromatography of MHC bound peptides purified from soluble MHC from $5 \times 10^7$ MCF-7 breast cancer cells. (2A) The total-ion-current chromatogram (TIC). (2B) Mass spectrum taken at the time point of 33.3 minutes. (2C) Spectrum of the collision-induced-disintegration (CID) of the dominant peptide in 2B having a m/z of 1028.5 that eluted at the 33.3 minutes. The putative MHC peptide GLIEKNIEL (SEQ ID NO:13) was identified to originate from DNA-methyl transferase.
Figure 2B:
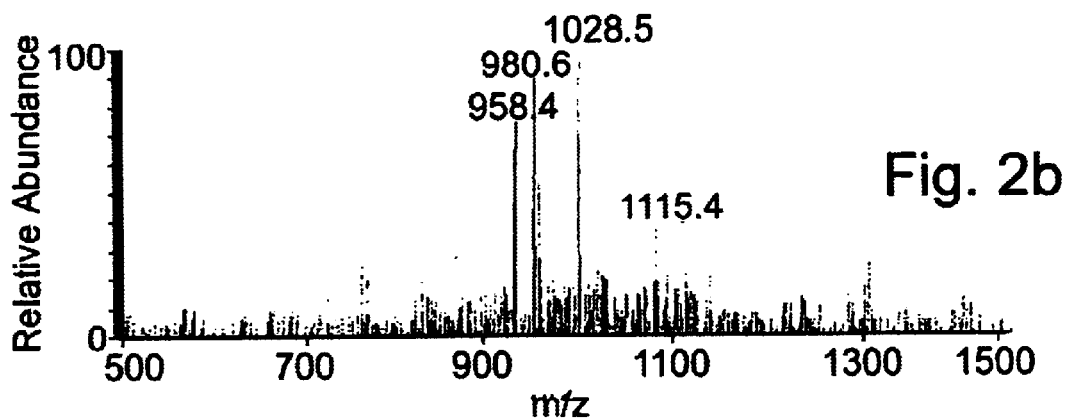
Figure 2C:
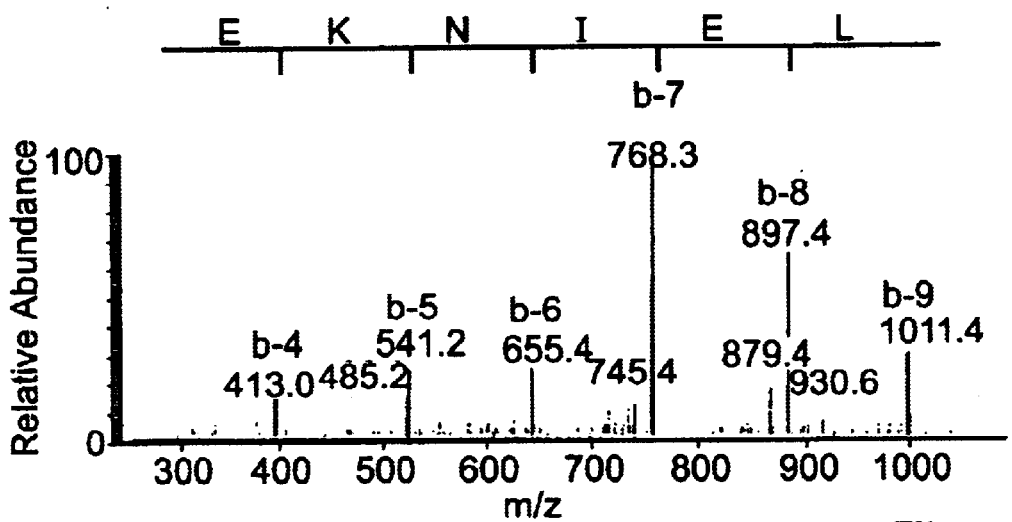

Sequencing of a large number of individual peptides was approached by electrospray tandem mass spectrometry. The peptides were partially resolved on homemade nano-capillary reversed phase columns interfaced directly to an electrospray mass spectrometer. The peptide mixtures were resolved by relatively long reversed-phase HPLC gradients on long capillary columns, enabling performing mass measurements and fragmentation of a large number of peptides. The mass spectra were recorded between 450 to 1500 mass units, which is the expected mass (m/z) range of the singly and the doubly charged MHC bound peptides. The mass spectrometry data included the total-ion-current chromatogram (TIC, FIG. 2A) and the mass spectrum of the peptides at each time point (FIG. 2B). The mass spectrometer was programmed to repeatedly select the most abundant peptide observed in each spectrum and to fragment it by CID (FIG. 2C). Peptides were identified by comparing their masses and the masses of their fragments to those calculated for peptides derived from all the human proteins in the databank. The computer programs were instructed to search for putative peptides resulting from non-specific proteolysis since the specificity of proteases responsible for generating the MHC bound peptides in cells is not well defined.

The relatively high sensitivity of the capillary ESI-MS/MS analysis and the large amounts of peptides recovered from the cells by use of the soluble MHC, enabled to perform multiple capillary HPLC separations with each peptide preparation. Peptides recovered from soluble MHC produced by about 5×10⁷ cells were used for each capillary chromatography. Multiple chromatography runs enabled to detect those peptides that were observed reproducibly and to combine their CID data to improve the signal-to-noise ratio of the CID spectra. The combined and improved data sets were used for databank searches and peptide identifications. Using relatively long capillary columns (of above 30 cm) and long reversed phase gradients facilitated achieving high resolving power. Most peptides elute normally during 15 to 30 seconds, which was a sufficient time for the mass spectrometer to analyze up to three different co-eluting peptides. The mass spectrometer was programmed not to fragment any peptide more than twice in order to increase the total number of peptides analyzed during each chromatography.

Figure 3A:
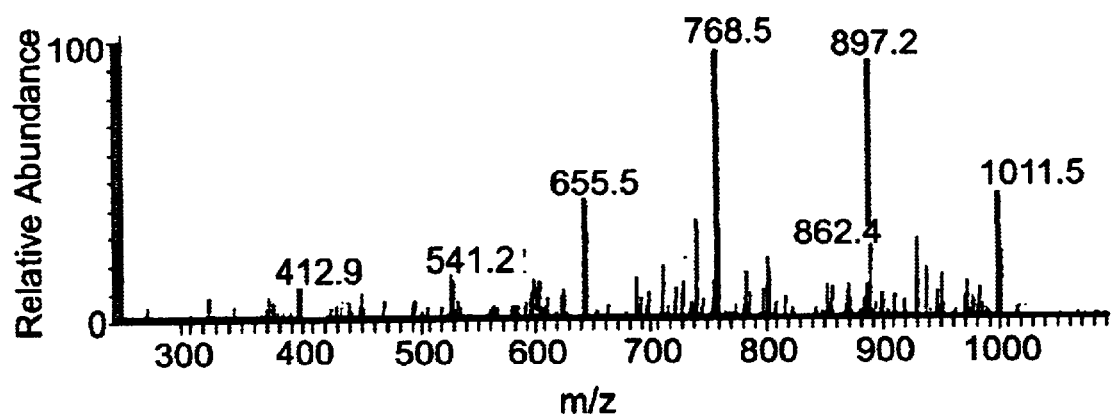
FIGS. 3A–B show a comparison of the chromatographs, the MS and the CID spectra of the synthetic peptide: GLIEKNIEL (SEQ ID NO:13) of the DNA methyl transferase (3A) with those of the peptide m/z=1028.5 (SEQ ID NO:13) from the breast cancer line MCF-7 (3B).
Figure 3B:
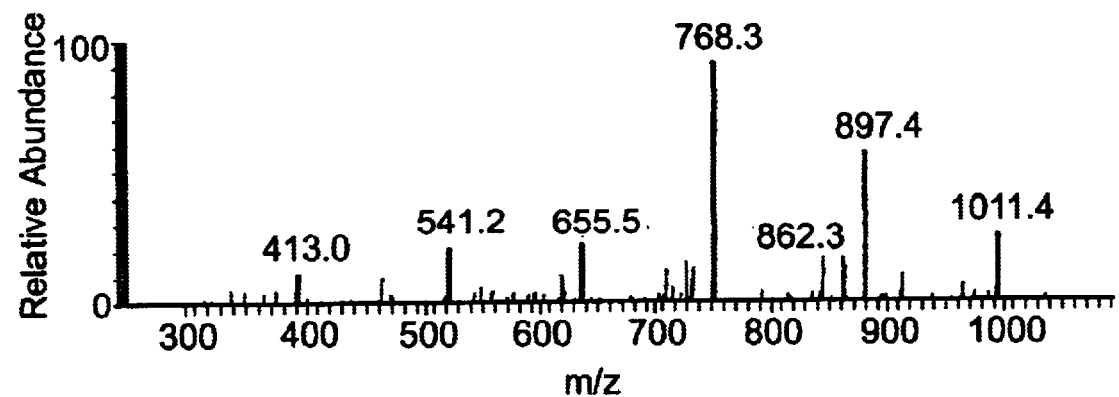

A total of about three thousands different peptides were sufficiently resolved and fragmented during the different chromatography runs of the mixtures eluted from the sHLA-A2 and sHLA-B7 recovered from the different cell lines. The large majority of the observed peptides were common to all the different cancer lines and only a small fraction was detected in only one of the cancer types. From this large number of detected peptides, about 200 were identified at high certainty to be derived from known proteins and the rest were not identified. Table 8 is typical list of such peptides recovered from the soluble MHCs and identified by the computer analysis. Among these peptides, fourteen were already known as MHC bound peptides. Those desired peptides that originate from putative tumor antigens were chemically synthesized to further evaluate the accuracy of their amino acid sequences and to enable to study them as MHC bound peptides and their significance as cancer antigens. Their amino acid sequence accuracy was ascertained by running a chromatography of the synthetic peptides using the exact conditions immediately after the natural peptides mixtures and comparing the chromatography retention times, the exact masses and the CID spectra of the synthetic and natural peptides (FIGS. 3A–B). When synthetic peptides behaved identically to the natural peptides in these three criteria served as a clear indication that the identification was indeed correct. Twenty-seven of the most interesting peptides were chemically synthesized and confined to be correct by this assay, example of which is displayed in FIGS. 3A-B.

TABLE 8

List of peptides recovered from sMHC of different cancer cells and identified at high certainty by mass spectrometry

|  | Mass (m/z) | Sequence (SEQ ID NO:) | Protein | Position[1] | Score[2] | Score[3] | Synthetic[4] | Ref[5] |
|---|---|---|---|---|---|---|---|---|
| | | | Peptides from soluble HLA-A2 | | | | | |
| 1 | 898.4 | LLDVPTAAV(1) | γ IFN inducible protein (IP-30) | 17–25 | 159.9 | 28 | | [41] |
| 2 | 1011.5 | LLLDVPTAAV(2) | γ IFN inducible protein (IP-30) | 16–25 | 1793.7 | 31 | | [41] |
| 3 | 1210.4 | LLLDVPTAAVQA(3) | γ IFN inducible protein (IP-30) | 16–27 | 128.1 | 21 | | [41] |
| 4 | 800.5 | GLLGTLVQ(4) | Beta catenin | 400–407 | 0.2 | 17 | + | |
| 5 | 913.4 | GLLGTLVQL(5) | Beta catenin | 400–408 | 181.7 | 31 | + | |
| 6 | 922.3 | ALFGALFLA(6) | Phospholipid transfer protein | 2–10 | 245.2 | 23 | + | |
| 7 | 945.4 | SLLGGDVVSV(7) | TSC-22-like protein | 22–32 | 591.9 | 34 | + | |
| 8 | 947.4 | NLTISDVSV(8) | MUC1 | 130–138 | 69.6 | 23 | + | [26] |
| 9 | 958.3 | SLWGQPAEA(9) | Human collagen type IV | 18–25 | 41.2 | 23 | + | |
| 10 | 981.7 | SLIGHQIL(10) | protein tyrosine posphatase | 336–244 | 49.1 | 32 | + | |
| 11 | 989.5 | SLSEKTVLL(11) | CD59 | 106–114 | 87.6 | 29 | + | |
| 12 | 989.4 | SLFPGKLEV(12) | flightless I homolog | 1010–18 | 257.3 | 30 | + | |
| 13 | 1028.5 | GLIEKNIEL(13) | DNA methyl transferase (MTDM) | 425–433 | 87.6 | 28 | + | |
| 14 | 1031.4 | GLYPGLIWL(14) | Interferon regulatory factor-6 | 21–29 | 864.8 | 30 | + | |
| 15 | 1038.5 | YLLPAIVHI(15) | RNA helicase | 146–154 | 408.4 | 30 | | [2] |
| 16 | 1068.4 | ALSDHHIYL(16) | Fructose bisphosphate aldolase | 216–224 | 481.7 | 23 | + | [21] |
| 17 | 1071.5 | ILDQKINEV(17) | ornithine decarboxylase | 23–31 | 108.8 | 30 | | [96] |
| 18 | 1071.6 | ILDKKVEKV(18) | Human HSP 90 beta, HSP 84 | 570–578 | 53.3 | 29 | | [74] |
| 19 | 1080.4 | SLLPPTALVGL(19) | H. Transporter SEC23A | 156–164 | 181.8 | 33 | | |
| 20 | 1091.4 | GVYDGEEHSV(20) | MACE-B2 | 231–240 | 79.9 | 20 | + | |
| 21 | 1094.5 | SLLPPDALVGL(21) | H. Transporter SEC23B | 150–160 | 181.8 | 33 | | |
| 22 | 1121.3 | TLWVDPYEV(22) | B-cell translocation gene (BTG1) | 103–111 | 577.3 | 24 | + | [2] |
| 23 | 1145.4 | FLFDGSPTYV(23) | Fatty acid synthase (FAS) | 292–301 | 2669.4 | 23 | + | |
| 24 | 1258.5 | FLFDGSPTYVL(24) | Fatty acid synthase (FAS) | 292–302 | 611.2 | 27 | + | |
| 25 | 1360.4 | ALWDIETGQQTV(25) | guanine nucleotide-binding | 167–178 | 2366.8 | 28 | + | |
| | | | Peptides from soluble HlLA-B7 | | | | | |
| 1 | 854.3 | VPSEPGGVL(26) | 70 kDa SHP-IL | 422–30 | 120 | 27 | + | |
| 2 | 883.4 | SPTQPIQL(27) | cell membrane glycoprotein 110000 Mr | 257–61 | 80 | 20 | | |
| 3 | 895.4 | SPALPGLKL(28) | transmembrane activator and CAML intetactor | 147–55 | 120 | 27 | + | |
| 4 | 899.5 | APRTVALTA(29) | HLA-SB beta | 9–17 | 60 | 24 | | [75] |
| 5 | 927.3 | SPKLPVSSL(30) | DNA binding protein homolog | 372–80 | 120 | 25 | + | |
| 6 | 989.3 | KPSLPFTSL(31) | translation initiation codon | 79–87 | 120 | 28 | + | |
| 7 | 999.5 | LVMAPRTVL(32) | MHC class-I | 2–10 | 335 | 18 | | [75] |
| 8 | 1050.4 | KPAFPAEKL(33) | annexin A1 | 274–82 | 80 | 22 | | |
| 9 | 1075.4 | SPYQNIKIL(34) | spermidine aminopropyltransferase | 128–36 | 80 | 20 | | |
| 10 | 1104.5 | AASKERSGVSL(35) | Histone H1 | 50–60 | 36 | 18 | | [75] |

TABLE 8-continued

List of peptides recovered from sMHC of different cancer cells and identified at high certainty by mass spectrometry

| | Mass (m/z) | Sequence (SEQ ID NO:) | Protein | Position[1] | Score[2] | Score[3] | Synthetic[4] | Ref[5] |
|---|---|---|---|---|---|---|---|---|
| 11 | 1114.3 | APFEPLASGIL(36) | precursor | 2–12 | 240 | 22 | + | |
| 12 | 1194.5 | APSGSLAVPLAVL(37) | hypothetical protein | 9–21 | 360 | 31 | | |

Table 8: An example of MHC bound peptides that were identified by the Sequest software [25] (obtained from Finnigan, San Jose, CA) after mass spectrometer analysis.
[1]Position of the first and the last amino acid of the peptide.
[2]Calculated score, estimating half the time for dissociation of the peptide-MHC complex [42].
[3]Calculate score.
[4]sequence approved by analyzing in comparison a synthetic peptide.
[5]Peptide is known.

Among the many peptides derived from different housekeeping proteins and enzymes, some peptides were determined to be derived from known tumor associated antigens. These include mucin (MUC-1) and MAGE-B2 while others were derived from proteins whose level is known to be significantly elevated in cancer cells such as beta-catenin, DNA methyl transferase and fatty acid synthase (Table 8).

Figure 4A:
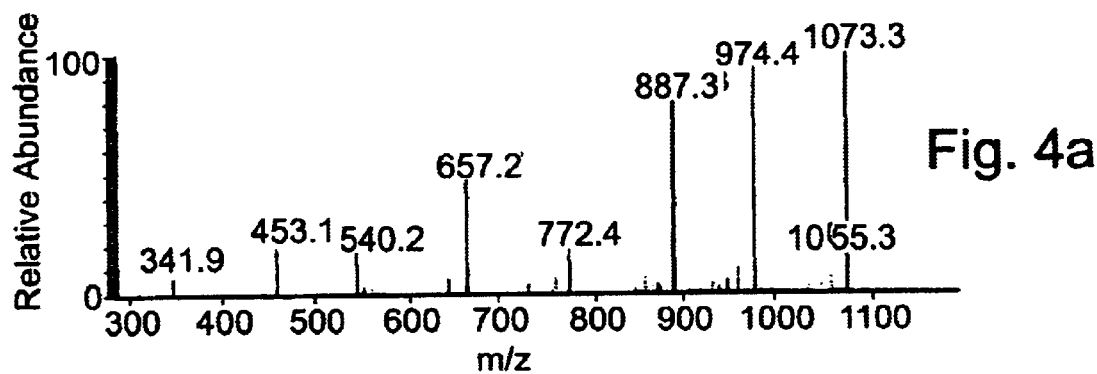
Figure 4B:
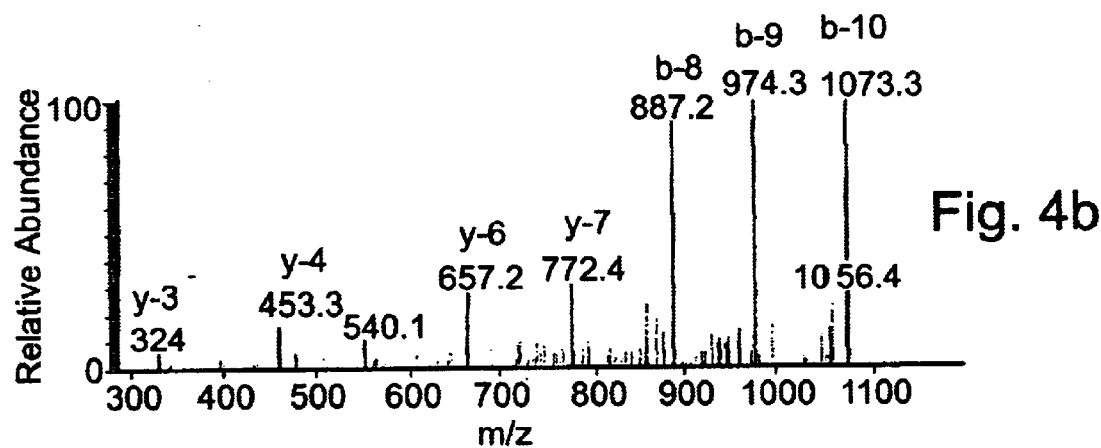
Figure 4C:
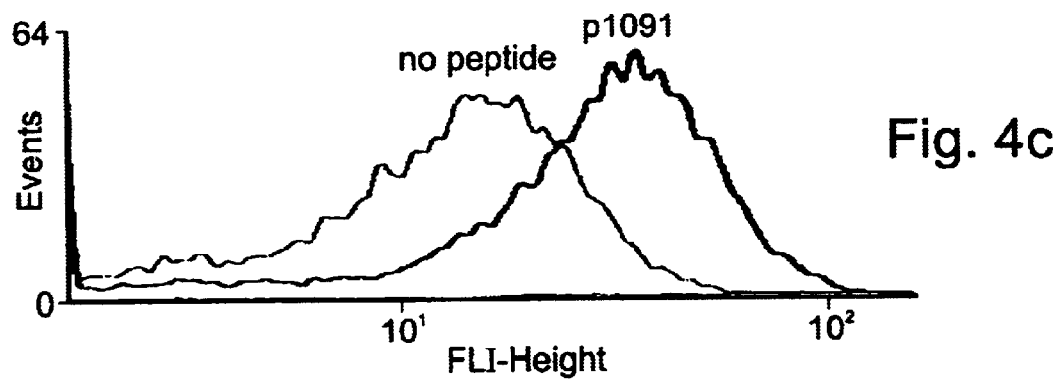

A comparison in the patterns of peptides presented by the same MHC in cell lines of different tissue origin enabled the identification of those peptide uniquely presented in only cells of a particular tissue origin. Only a few of the peptides were determined to be unique to specific cell lines while most of the peptides that were observed in all the different cell lines were derived from normal cellular proteins. Also, significantly different patterns of peptides were recovered from sHLA-A2 and from sHLA-B7. Examples for unique peptides which are displayed in Table 9 include peptide p922 (phospholipid transfer protein) recovered only from PC3 cells and peptide p947 (SEQ ID NO:8) (MUC1) recovered only from MCF-7 grown without estrogen. Peptide p945 (SEQ ID NO:7, derived from TSC-22-like protein) is a novel peptide that was detected at high level in the two-breast cancer cells (MCF-7 and MDA-231), but was not observed in the ovarian (UCI-107) and the prostate (PC3) cancer cells. Peptide p981 (SEQ ID NO:10) originated from protein tyrosine phosphatase, and was detected only in the breast cancer cell MDA-231. One of the most interesting novel peptides identified was p1091 (SEQ ID NO:20) derived from the tumor antigen MAGE-B2. The peptide was detected only in the ovarian cancer cells (UCI-107) and not in the other cell lines. The synthetic and natural peptides elution pattern and CID spectra of both were identical (FIGS. 4A and 4B). The binding affinity of this peptide to the MHC molecules was determined to be normal as assayed by reconstitution and stabilization of empty MHC on the surface of RMA-S-HHD) cells FIG. 4C). This peptide is derived from the same region in the MAGE proteins, as do other previously identified MHC bound peptides derived from MAGE-A4 and from MACE-A10 [27, 28] (FIG. 4D).

TABLE 9

Comparison of MHC peptide patterns between cell lines of diffferent cancer origin

| | Mass (m/z) | Sequence (SEQ ID NO.) | MCF-7 | [1]MCF-7 without estrogen | MDA-231 | PC-3 | UCI-107 | UCI-101 |
|---|---|---|---|---|---|---|---|---|
| (A) | | | | | | | | |
| 1 | 898.4 | LLDVPTAAV(1) | + | + | + | + | + | + |
| 2 | 1011.5 | LLLDVPTAAV(2) | + | + | + | − | + | + |
| 3 | 1210.5 | LLLDVPTAAVQA(3) | + | + | + | + | + | + |
| 4 | 800.5 | GLLGTLVQ(4) | − | − | − | + | + | − |
| 5 | 913.4 | GLLGTLVQL(5) | + | + | + | + | + | + |
| 6 | 922.3 | ALFGALFLA(6) | − | − | − | + | − | − |
| 7 | 945.4 | SLLGGDVVSV(7) | + | + | + | − | − | − |
| 8 | 947.4 | NLTISDVSV(8) | − | + | − | − | − | − |
| 9 | 958.3 | SLWGQPAEA(9) | + | + | − | + | + | + |
| 10 | 981.7 | SLIGHLQTL(10) | − | − | + | − | − | − |
| 11 | 989.5 | SLSEKTVLL(11) | + | + | + | − | + | + |
| 12 | 989.4 | SLFPOKLEV(12) | + | + | + | + | + | + |
| 13 | 1028.5 | GLIEKNIEL(13) | + | + | + | + | + | + |
| 14 | 1031.4 | GLYPGLIWL(14) | + | + | + | + | − | + |
| 15 | 1038.5 | YLLPAIVHI(15) | + | + | + | + | + | + |
| 16 | 1068.4 | ALSDHHIYL(16) | + | + | + | + | + | + |
| 17 | 1071.5 | ILDQKINEV(17) | − | + | + | + | + | − |
| 18 | 1071.6 | ILDKKVEKV(18) | − | + | + | + | + | + |
| 19 | 1080.4 | SLLPPTALVGL(19) | − | − | + | − | + | + |
| 20 | 1091.4 | GVYDGRRHSV(20) | − | − | − | − | + | − |
| 21 | 1094.4 | SLLPPDALVGL(21) | + | + | + | − | + | + |
| 22 | 1121.3 | TLWVDPYBV(22) | + | + | + | + | + | + |
| 23 | 1145.4 | FLFDGSPTYV(23) | + | − | + | − | + | − |

TABLE 9-continued

Comparison of MHC peptide patterns between cell lines of diffferent cancer origin

| 24 | 1258.5 | FLFDGSPTYVL(24) | + | + | + | − | + | + |
| 25 | 1360.4 | ALWDIETGQQTV(25) | − | − | + | − | + | − |

| | Mass (m/z) | Sequence (SEQ ID NO:) | C1R | MDA-231 | UCI-107 |
|---|---|---|---|---|---|
| (B) | | | | | |
| 1 | 854.3 | VPSEPGGVL(26) | + | − | − |
| 2 | 883.4 | SPTQPIQL(27) | − | + | − |
| 3 | 895.4 | SPALPGLKL(28) | + | − | − |
| 4 | 899.4 | APRTVALTA(29) | + | − | − |
| 5 | 999.5 | SPKLPVSSL(30) | + | + | + |
| 6 | 927.3 | KPSLPFTSL(31) | + | − | + |
| 7 | 989.3 | LVMAPRTVL(32) | + | − | − |
| 8 | 1050.4 | KPAFFAEKL(33) | − | − | + |
| 9 | 1075.4 | SPYQNIKIL(34) | − | + | − |
| 10 | 1104.5 | AASKERSGVSL(35) | + | − | + |
| 11 | 1114.3 | APPEPLASQIL(36) | + | + | + |
| 12 | 1194.5 | APSGSLAVPLAVL(37) | − | + | − |

Table 9:
(A) The appearance of peptides from soluble HLA-A2 in breast cancer cells MCF-7 and MDA-231, [1]MCF-7 that grown without estrogen, prostate cancer cell PC-3 and the ovarian cancer cells UCI-107 and UCI-101.
(B) The appearance of peptides from soluble HLA-B7 in B cell leukemia cancer cells C1R, breast cancer cells MDA-231 and ovarian cancer cells UCI-107.

Another approach to ascertain that the identified peptides were indeed MHC bound peptide antigens, their capacity to bind tightly and stabilize cell surface HLA-A2.1 was tested by reconstitution into empty MHC on the surface of RMA-S-HHD cells. Binding was assayed by FACS analysis after decorating the cells with the fluorescent anti-intact MHC mAb W6/32 (FIG. 5). Nine of the synthetic peptides were determined to stabilize cell surface MHC significantly more than without the added peptides and to a similar extent as peptide (G9-209-2M) IMDQVPFSV (SEQ ID NO:42), derived from the melanoma protein gp-100 [29].

To further evaluate the affinity of the peptides to the HLA-A2 and to obtain some insight into their immunogenic potential, selected peptides were tested for their ability to induce an immune response in HLA-A2 transgenic mice. It was assumed that only peptides that could be effectively presented and remain tightly bound to the cells would be capable of inducing an immune response in these mice. The same synthetic peptides that were used for the FACS analysis were used for immunization of the HHD transgenic mice, which express the human HLA-A2.1/Db-β2 m single chain. To immunize the mice, the HHD culture cells were loaded with the different peptides and then injected to the HHD mice. The immune response in the mice was followed by the appearance of CTLs specific for these peptides. The lysis patterns of the target HHD cells by T-cells taken from the immunized mice are shown in FIG. 6. Some of the peptides were indeed capable of inducing an immune response, which both authenticate them as MHC bound peptides and gives an indication about their immunogenic potential. The CTL results demonstrate significant lysis of EL4-HHD cells loaded with the peptides p1028 (SEQ ID NO:13) from DNA methyl transferase, p1258 (SEQ ID NO:24) from fatty acid synthase, p1121 (SEQ ID NO:22) from B cell translocation gene (BTG) and p1068 (SEQ ID NO:16) from aldolase as compared to the negative control peptide ALLCAPSLL (SEQ ID NO:43).

SUMMARY OF PEPTIDE INFORMATION FOR SOLUBLE HLA-A2

The following provides a summary of peptide information so far collected for eptides bound to soluble HLA-A2 using the method of the present invention.

The following notations are used herein:

| | |
|---|---|
| G: | group number until May 7, 2001 |
| Mg: | mass of the natural peptide |
| Mp: | mass of the identified peptide |
| Tg: | observed retention time of the natural peptide |
| Tp: | calculated retention time of the identified peptide |
| S: | calculated internal score |
| A2: | adherence to HLA-A2 consensus motif |
| B7: | adherence to HLA-BT consensus motif |
| P: | identified peptide sequence |
| PR: | protein from which sequence is derived |
| POS: | location of peptide in protein |
| genpept: | link to protein information in GenBank |
| ref: | previously known peptide |
| Cell lines: | |
| #D: | PC3 + A2/Q10 |
| #E: | MCF7 + A2/Q10 |

-continued

```
#F:                MDA-231 + A2/Q10
#EST:              MCF7 (with estrogen) + A2/Q10
#FR:               MCF7 (without estrogen) + A2/Q10
#G:                UCI-107 + A2/Q10
#H:                C1R + SB7
#I:                UCI-107 + SB7
#J:                MDA-2311-SB7
#K:                UCI-101 + SA2
#L:                2780 (ovarian cancer cell line) + sA2
#S:                synthetic peptides
```

G = 1990: Mg = 800.4: #S + (2, 1) #G + (10, 7)S = 83 (87, 74) Mg = 800.5 Tg = 38 +− 0
Tp = 53 Mp = 800.5 A2 = 0.02 / 18 P = GLLGTLVQ
genpept PR = >gi|860988|emb|CAA61107.1|(X87838) beta-catenin
[Homo sapiens] POS = 399 (SEQ ID NO: 4)
G = 1234: Mg = 810.3: Tg = 31 +− 1 #D + (2, 2) #E + (7, 4) #F + (4, 3) #EST + (7, 2)
FR + (4, 2) #G + (33, 11) #K + (3, 2) #L + (2, 1)
S = 84(87, 79) Mp = 810.2(−0, 1) Tp = 34 A2 = 11 / 29 P = ALAPGLPTA
genpept PR = >gi|5771535|gb|AAD51419. 1|AF173937_1 (AF173937) secreted
protein of unknown function [Homo sapiens] POS = 21 (SEQ ID NO: 44)
G = 1251: Mg = 811.4: Tg = 35 +− 0 #G + (5, 3)
S = 96(96, 99) Mp = 811.5(0.1) Tp = 36 A2 = 465 / 26 P = KLLBPVL
genpept PR = >gi|338447|gb|AAA60583.1|(M60854) RPS16 [Homo sapiens]
POS = 50 (SEQ ID N0: 45)
G = 1378: Mg = 841.3: Tg = 41 +− 0 #G + (9, 5)
S = 77(83, 66) Mp = 841.4(0.1) Tp = 40 A2 = 0.0 / 16 P = SLLPAIVE
genpept PR = >gi|189428|gb|AAA36399.1|(J02902) phosphatase 2A
regulatory subunit [Homo sapiens] POS = 403 (SEQ ID NO: 46)
G = 1419: Mg = 848.3: Tg = 34 +− 1 #E + (2, 1) #F + (2, 1) #G + (5, 5) #K + (1, 1)
S = 84(83, 89) Mp = 848.4(0.1) Tp = 34 A2 = 52 / 26 P = SVLGSLSSV
genpept PR = >gi|5833114|gb|AADS3401.1|AF107840 1 (AF107840) nuclear
pore-associated protein [Homo sapiens] POS = 280 (SEQ ID NO: 47)
G = 1420: Mg = 848.4: Tg = 37 +− 1 #D + (2, 2) #E + (11, 6) #F + (8, 5) #EST + (3, 2) #FR + (4, 2) #G + (25, 11)
S = 95(94, 99) Mp = 848.4(0.0) Tp = 39 A2 = 118 / 28 P = LLGPPPVGV
genpept PR = >gi|10436199|dbj|BAB14750.1|(AK023978) unnamed protein
product [Homo sapiens] POS = 159 (SEQ ID N0: 48)
G = 1439: Mg = 852.3: Tg = 22 +− 2 #FR + (2, 1) #I + (32, 6)
S = 83(81, 89) Mp = 852.0(−0.3) Tp = 25 A2 = 0.0 / 1 P = PGPPPPPPP
genpept PR = >gi|5689367|dbj|BAA82967.1|(AB021227) membrane-type-5
matrix metalloproteinase [Homo sapiens] POS = 11 (SEQ ID NO: 49)
G = 1492: Mg = 860.3: Tg = 37 +− 1 #G + (9, 5)
S = 81(87, 69) Mp = 360.3(0.0) Tp = 31 A2 = 116 / 28 P = SMSGPLIGV
genpept PR = >gi|1469189|dbj|BAA09482.1|(D50923) The KIAA0133 gene
product is novel. [Homo sapiens] POS = 629 (SEQ ID NO: 50)
G = 1510: Mg = 862.5: Tg = 29 +− 2 #F + (4, 4) #G + (4, 2)
S = 78(87, 59) Mp = 862.2(−0.3) Tp = 27 A2 = 116 / 32 P = SMAPGLTSV
genpept PR = >gi|124B4559|gb|AAF20366.2|AF150754_1 (AF150754)
3'-phosphoadenosine 5'-phosphosulfate synthase 2b isoform [Homo
sapiens] POS = 542 (SEQ ID NO: 51)
G = 1540: Mg = 868.4: Tg = 43 +− 0 #E + (2, 1) #F + (7, 4) #FR + (1, 1) #G + (4, 4) #K + (3, 3)
S = 83(89, 69) Mp = 868.4 (0.0) Tp = 46 A2 = 19 / 30 P = LLIPGLATA
genpept PR = >gi|2274974|emb|CAA57489.1|(X81900) NADH oxidoreductase
subunit MWFE [Homo sapiens] POS = 16 (SEQ ID NO: 52)
G = 1563: Mg = 871.3: Tg = 36 +− 1 #D + (1, 1) #E + (8, 6) #F + (4, 3) #EST + (3, 2)
FR + (5, 2) #G + (15, 9)
S = 86(89, 79) Mp = 871.4(0.1) Tp = 33 A2 = 592 / 33 P = GLLGNVAEV
genpept PR = >gi|12655181|gb|AAH01447.1|AAH01447 (BC001447) Similar to
ZYG homolog [Homo sapiens] POS = 10 (SEQ ID NO: 53)
G = 1575: Mg = 872.4: Tg = 32 +− 3 #D + (2, 1) #E + (3, 3) #F + (24, 7) #EST + (3, 2)
FR + (4, 2) #G + (12, 7)
S = 79(76, 88) Mp = 872.5(0.1) Tp = 33 A2 = 11 / 26 P = SLIKLVEA
genpept PR = >gi|7020538|dbj|BAA91170.1|(AK000444) unnamed protein
product [Homo sapiens] POS = 277 (SEQ ID NO: 54)
G = 1606: Mg = 876.4: Tg = 28 +− 2 #E + (2, 1) #F + (2, 1) #EST + (1, 1) #FR + (4, 2)
S = 84(82, 89) Mp = 876.3(−0.1) Tp = 32 A2 = 201 / 31 P = GLAESVSTL
genpept PR = >gi|12652733|gb|AAHOOH6.1|AAH00116 (BC000116) Similar to
KIAA0174 gene product [Homo sapiens] POS = 95 (SEQ ID NO: 55)
G = 1621: Mg = 878.3: Tg = 40 +− 1 #E + (6, 4) #F + (4, 2) #EST + (1, 1) #FR + (3, 2)
G + (11, 8) #K + (1, 1)
S = 88(92, 79) Mp = 878.4(0.1) Tp = 40 A2 = 55 / 30 P = AIIGGTFTV
genpept PR = >gi|6330243|dbj|BAA86495.1|(AB033007) KIAA1181 protein
[Homo sapiens] POS = 304 (SEQ ID NO: 56)
G = 1637: Mg = 880.3: Tg = 37 +− 0 #H + (5, 3)
S = 88(89, 88) Mp = 880.4(0.1) Tp = 40 A2 = 2 / 23 P = IITGPAPVL
genpept PR = >gi|7542357|gb|AAF63417.1|AF142422_1 (AF142422) QUAKING
isoform 3 [Homo sapiens] POS = 250 (SEQ ID NO: 57)
G = 1655: Mg = 882.3: Tg = 43 +− 1 #F + (1, 1) #G + (6, 4) #K + (1, 1)
S = 87(87, 88) Mp = 882.3(0.0) Tp = 43 A2 = 0.0 / 18 P = SFDGWATV
genpept PR = >gi|7263944|emb|CAB81773.1|(AJ276359) mucin 4 [Homo
sapiens] POS = 1560 (SEQ ID NO: 58)

-continued

G = 1732: Mg = 894.4: Tg = 42 +− 0 #G + (6, 3)
S = 79(82, 72) Mp = 894.4(0.0) Tp = 41 A2 = 2 / 20 P = LPPDALVGL
genpept PR = >gi|1296666|emb|CAA65775.1|(X97065) Sec23 protein [Homo sapiens] POS = 158 (SEQ ID NO: 59)
G = 1737: Mg = 895.3: Tg = 14 +− 1 #G + (4, 2)
S = 76(79, 72) Mp = 895.4(0.1) Tp = 22 A2 = 47 / 25 P = ILDAGGHNV
genpept PR = >gi|1808578|dbj|BAAO7918.1|(D44466) proteasome subunit p112 [Homo sapiens] POS = 736 (SEQ ID NO: 60)
G = 1744: Mg = 896.3: Tg = 28 +− 3 #D + (6, 3) #E + (14, 5) #F + (20, 6) #EST + (5, 2) #FR + (6, 3) #G + (47, 11) *K + (8, 4)
S = 92(98, 81) Mp = 896.4(0.1) Tp = 30 A2 = 512 / 30 P = GLYSGVTTV
genpept PR = >gi|36065|emb|CAA42118.1|(X59543) M1 subunit of ribonucleotide reductase [Homo sapiens] POS = 46 (SEQ ID N0: 61)
G = 1745: Mg = 896, 3: Tg = 55 +− 0 #G + (8, 4)
S = 79(76, 86) Mp = 896.5(0.2) Tp = 60 A2 = >1k / 24 P = FLYPFPL
genpept PR = >gi|436224|dbj|BAA05062.1|(D26067) KIAA0033 [Homo sapiens] POS = 185 (SEQ ID NO: 62)
G = 1768: Mg = 898.4: Tg = 36 +− 1 #D + (11, 3) #E + (50, 10) #F + (13, 7) #EST + (7, 2) #FR + (13, 3) #G + (63, 11) #K + (15, 6) #L + (9, 3)
S = 81(78, 89) Mp = 898.4(0.0) Tp = 36 A2 = 47 / 28 P = LLDVPTAAV
genpept PR = >gi|6165618|gb|AAF04618.1|AF097362_1 (AF097362) gamma-interferon inducible lysosomal thiol reductase [Homo sapiens] POS = 27 (SEQ ID N0:1) ref
G = 1770: Mg = 898.4: Tg = 38 +− 1 #E + (4, 2) #F + (3, 2) #FR + (1, 1) #G + (18, 11) #K + (2, 1)
S = 88(92, 79) Mp = 898.3(-0.1) Tp = 41 A2 = 79 / 29 P = ALLPSSPTL
genpept PR = >gi|1737205|gb|AAB38876.1|(U75276) TFIIB related factor hBRF [Homo sapiens] POS = 609 (SEQ ID NO: 63)
G = 1786: Mg = 899.5: Tg = 26 +− 2 #F + (2, 2) #EST + (4, 2) #FR + (5, 2) #G + (32, 8) #K + (8, 5) #L + (1, 1)
S = 93(96, 89) Mp = 899.5(0.0) Tp = 27 A2 = 243 / 25 P = KLGSVPVTV
genpept PR = >gi|12653653|gb|AAH00609.1|AAH00609 (BC000609) KIAA0738 gene product [Homo sapiens] POS = 623 (SEQ ID NO: 64)
G = 1795: Mg = 900.4: Tg = 53 +− 0 #D + (2, 2) #E + (7, 5) #F + (11, 6) #EST + (2, 1) #FR + (6, 3) #G + (21, 11) #K + (16, 6)
S = 81(86, 72) Mp = 900.5(0.1) Tp = 55 A2 = 182 / 33 P = ALFPGVALL
genpept PR = >gi|2245365|gb|AAC51518.1|(075885) ER-60 protein [Homo sapiens] POS = 7 (SEQ ID NO: 65)
G = 1802: Mg = 901.3: Tg = 33 +− 2 #E + (3, 2) #G + (2, 1)
S = 85(92, 69) Mp = 901.5(0.2) Tp = 32 A2 = 160 / 29 P = GLVGSLQEV
genpept PR = >gi|11967711|emb|CAC19484.1|(AJ278357) Tsg24 protein [Homo sapiens] POS = 56 (SEQ ID NO: 66)
G = 1804: Mg = 901.4: Tg = 31 +− 2 #E + (1, 1) #FR + (1, 1) #G + (6, 3)
S = 90(95, 79) Mp = 901.3(-0.1) Tp = 22 A2 = 2 / 18 P = APLSDTAQV
genpept PR = >gi|10438789|dbj|BAB15344.1|(AK026063) unnamed protein product [Homo sapiens] POS = 197 (SEQ ID NO: 67)
G = 1804: Mg = 901.4: Tg = 31 +− 2 #E + (1, 1) #FR + (1, 1) #G + (6, 3)
S = 89(94, 79) Mp = 901.5(0.1) Tp = 36 A2 = 160 / 33 P = SLASLLAKV
genpept PR = >gi|3489831|gb|AAF75772.1|AF265555_1 (AF265555) ubiquitin-conjugating BIR-domain enzyme APOLLON [Homo sapiens] POS = 1230 (SEQ ID NO: 68)
G = 1822: Mg = 903.3: Tg = 16 +− 7 #D + (7, 3) #E + (14, 4) #F + (14, 4) #EST + (18, 2) #FR + (13, 3) #G + (116, 10) #K + (20, 6)
S = 92(98, 79) Mp = 903.4(0.1) Tp = 23 A2 = 160 / 29 P = GLATOVQTV
genpept PR = >gi|565647|dbj|BAA05645.1|(D26598) proteasome subunit HsC10-II [Homo sapiens] POS = 55 (SEQ ID NO: 69)
G = 1860: Mg = 907.5: Tg = 39 +− 1 #D + (12, 4) #E + (1, 1) #F + (9, 5) #EST + (3, 1) #FR + (4, 2) #G + (10, 6) #K + (4, 3)
S = 88(91, 81) Mp = 907.5(0.0) Tp = 37 A2 = 79 / 31 P = SLFGGSVKL
genpept PR = >gi|13375569|gb|AAK20398.1|AF349951_1 (AF349951) HP95 [Homo sapiens] POS = 103 (SEQ ID NO: 70)
G = 1861: Mg = 907.6: Tg = 38 +− 1 #EST + (2, 1) #FR + (1, 1)
S = 87(87, 89) Mp = 907.6(0.0) Tp = 32 A2 = 21 / 19 P = KVGPVPVLV
genpept PR = >gi|12804623|gb|AAH01734.1|AAH01734 (BC001734) protein translocation complex beta [Homo sapiens] POS = 67 (SEQ ID NO: 71)
G = 1899: Mg = 910.3: Tg = 46 +− 1 #E + (8, 5) #F + (21, 7) #EST + (4, 2) #FR + (7, 3) #G + (24, 11) #K + (13, 6) #L + (3, 2)
S = 72(65, 89) Mp = 910.4(0.1) Tp = 40 A2 = 182 / 32 P = GLLPDVPSL
genpept PR = >gi|13623421|gb|AAH06309.1|AAH06309 (BC006309) Similar to RIKEN cDNA 5730589L02 gene [Homo sapiens] POS = 141 (SEQ ID NO: 72)
G = 1901: Mg = 910.4: Tg = 39 +− 0 #D + (2, 1) #E + (5, 2) #F + (9, 5) #EST + (1, 1) #FR + (1, 1)
S = 80(90, 59) Mp = 910.4(0, 0) Tp = 41 A2 = 160 / 30 P = ALPPVLTTV
genpept PR = >gi|3882133|dbj|BAA34451.1|(AB018274) KIAA0731 protein [Homo sapiens] POS = 131 (SEQ ID NO: 73)
G = 1904: Mg = 910.4: Tg = 38 +− 1 #E + (2, 1) #F + (3, 2) #EST + (1, 1) #FR + (3, 2) #G + (3, 3) #K + (2, 1)
S = 90(95, 79) Mp = 910.5(0.1) Tp = 32 A2 = 52 / 24 P = GVLPNIQAV
genpept PR = >gi|7264004|emb|CAB81656.1|(AL049822) dJ160A22.4 (histone H2A) [Homo sapiens] POS = 107 (SEQ ID NO: 74)
G = 1922: Mg = 912.5: Tg = 42 +− 1 #E + (5, 4) #F + (2, 1) #FR + (1, 1) #G + (3, 2) #K + (1, 1)

-continued

S = 78(83, 69) Mp = 912.5(0.0) Tp = 43 A2 = 49 / 31 P = ALTPVVVTL
genpept PR = >gi|13177739|gb|AAH03644.1|AAH03644 (BC003644)
cyclin-dependent kinase 4 [*Homo sapiens*] POS = 170 (SEQ ID NO: 75)
G = 1931: Mg = 913.4: Tg = 34 +− 1 #E + (8, 4) #F + (2, 2) #EST + (3, 2) #FR + (1, 1)
S = 84(96, 59) Mp = 913.3(−0.1) Tp = 29 A2 = 70 / 27 P = ALNPADITV
genpept PR = >gi|6634421|emb|CAB64373.1|(AJ238375) putative protein
TH1 [*Homo sapiens*] POS = 103 (SEQ ID NO: 76)
G = 1933: Mg = 913.4: Tg = 49 +− 0 #S + (12, 2) #D + (17, 5) #E + (16, 8)
F + (18, 7) #EST + (2, 1) #FR + (4, 2) #G + (22, 11) #H + (1, 1) #K + (10, 6)
S = 93(95, 89) Mp = 913.6(0.2) Tp = 46 A2 = 182 / 31 P = GLLGTLVQL
genpept PR = >gi|38520|emb|CAA79497.1|(Z19054) beta catenin [*Homo
sapiens*] POS = 400 (SEQ ID N0:5)
G = 1939: Mg = 914.4: Tg = 40 +− 0 #G + (4, 3)
S = 82(79, 89) Mp = 914.4(0.0) Tp = 42 A2 = 0.0 / 16 P = DAEGLALLL
genpept PR = >gi|1060907|dbj|BAA11242.1|(D78177) quinolinate
phosphoribosyl transferase [*Homo sapiens*] POS = 2 (SEQ ID N0:77)
G = 1942: Mg = 914.5: Tg = 16 +− 3 #F + (4, 1) #G + (6, 3)
S = 90(95, 79) Mp = 914.4(−0.1) Tp = 27 A2 = 160 / 29 P = SLTGHISTV
genpept PR = >gi|2832296|gb|AAD09407.1|(AF044333) pleiotropic
regulator 1 [*Homo sapiens*] POS = 241 (SEQ ID NO: 78)
G = 1948: Mg = 915.5: Tg = 38 +− 0 #D + (2, 1) #F + (11, 7)
S = 91(97, 77) Mp = 915.6(0.1) Tp = 42 A2 = 0.5 / 15 P = VHVLTFTV
genpept PR = >gi|3242214|emb|CAA07243.1|(AJ006778) DRIM protein [*Homo
sapiens*] POS = 1896 (SEQ ID N0:79)
G = 1974: Mg = 918.3: Tg = 36 +− 1 #F + (3, 2) #G + (19, 10)
S = 84 (88, 77) Mp = 918.6(0.3) Tp = 34 A2 = 6 / 25 P = SLKYVPLV
genpept PR = >gi|10436278|dbj|BAB14783.1|(AK024024) unnamed protein
product [*Homo sapiens*] POS = 248 (SEQ ID NO: 70)
G = 1979: Mg = 918.6: Tg = 53 +− 0 #E + (5, 3) #F + (6, 3) #EST + (1, 1) #FR + (4, 2)
G + (4, 2) #K + (4, 3)
S = 81(84, 74) Mp = 913.5(−0.1) Tp = 54 A2 = 0.8 / 16 P = LPYWGVAL
genpept PR = >gi|7023639|dbj|BAA52035.1|(AK002014) unnamed protein
product [*Homo sapiens*] POS = 272 (SEQ ID NO: 71)
G = 1988: Mg = 920.3: Tg = 32 +− 1 #E + (2, 2) #F + (5, 2) #FR + (1, 1) #G + (35, 11) #K + (1, 1)
S = 89(90, 89) Mp = 920.3(0.0) Tp = 27 A2 = 31 / 24 P = SIYPSPTGV
genpept PR = >gi|3661610|gb|AAC61776.1|(AF092565) splicing factor
Prp8 [*Homo sapiens*] POS = 1693 (SEQ ID NO: 72)
G = 2008: Mg = 922.3: Tg = 58 +− 1 #S + (9, 1) #D + (17, 5) #L + (8, 2)
S = 79(80, 77) Mp = 922.5(0.3) Tp = 59 A2 = 245 / 22 P = ALFGALFLA
genpept PR = >gi|2653432|dbj|BAA23647.1|(AB005297) BAI 1 [*Homo
sapiens*] POS = 1163 (SEQ ID NO: 6)
G = 2023: Mg = 924.2: Tg = 15 +− 14 #F + (6, 3) #FR + (1, 1)
S = 83(86, 79) Mp = 924.4(0.2) Tp = 33 A2 = 11 / 24 P = ALASHLIEA
genpept PR = >gi|7212807|gb|AAF40470.1|AF181263_1 (AF181263) EH domain
containing 2 [*Homo sapiens*] POS = 507 (SEQ ID NO: 73)
G = 2027: Mg = 924.5: Tg = 13 +− 1 #G + (3, 2)
S = 83(85, 79) Mp = 924.4(−0.1) Tp = 20 A2 = 75 / 24 P = KLGPAPKTL
genpept PR = >gi|408198|gb|AAB27691.1|(S64671) DNA-binding
protein/plasminogen activator inhibitor-1 regulator [human, HeLa S3,
Peptide Partial, 176 aa] [*Homo sapiens*] POS = 133 (SEQ ID NO: 74)
G = 2029: Mg = 924.5: Tg = 43 +− 1 #F + (1, 1) #G + (17, 8)
S−93(91, 99) Mp = 924.6(0.1) Tp = 44 A2 = >1k / 27 P = KLLEPVLL
genpept PR = >gi|338447|gb|AAA60583.1|(M60854) RPS16 [*Homo sapiens*]
POS = 5O (SEQ 10 NO: 75)
G = 2050: Mg = 926.5: Tg = 14 +− 3 #F + (8, 2) #EST + (1, 1) #FR + (3, 2) #G + (6, 3)
S = 90(96, 79) Mp = 926.4(−0.1) Tp = 29 A2 = 78 / 30 P = ALSGHLETV
genpept PR = >gi|12314197|emb|CAB99342.1|(AL139008) bA255A11.8 (novel
protein similar to annexin A2 (ANXA2) (lipocortin II, calpactin I
heavy chain, chromobindin 8, PAP-IV)) [*Homo sapiens*] POS = 90 (SEQ ID
N0: 76)
G = 2068: Mg = 929.5: Tg = 43 +− 1 #E + (2, 2) #F + (20, 7) #FR + (1, 1)
G + (36, 11) #K + (24, 6) #L + (3, 2)
S = 92(90, 99) Mp = 929.5(0.0) Tp = 31 A2 = 173 / 25 P = SLLDKIIGA
genpept PR = >gi|11034809|gb|AAG27093.1|AF312393_1 (AF312393)
leucine-zipper protein FKSG13 [*Homo sapiens*] POS = 56 (SEQ ID N0: 77)
G = 2071: Mg = 930.3: Tg = 35 +− 1 #F + (4, 3) #G + (13, 7) #K + (3, 2)
S = 91(97, 77) Mp = 930.4(0, 1) Tp = 33 A2 = 257 / 33 P = GLLGAGGTVSV
genpept PR = >gi|11493522|gb|AAG35534.1|AF130117_68 (AF130109) PR01512
[*Homo sapiens*] POS = 17 (SEQ ID N0: 78)
G = 2072: Mg = 930.4: Tg = 53 +− 0 #D + (8, 4) #E + (21, 8) #F + (10, 5)
EST + (7, 2) #FR + (8, 3) #G + (11, 7) #K + (7, 4)
S = 78(83, 69) Mp = 930.6(0.2) Tp = 53 A2 = 608 / 32 P = GLVPFLVSV
genpept PR = >gi|13543657|gb|AAH05978.1|AAH05978 (BC005976)
karyopherin alpha 2 (RAG cohort 1, importin alpha 1) [*Homo sapiens*]
POS = 377 (SEQ ID N0: 79)ref
G = 2095: Mg = 932.5: Tg = 46 +− 0 #F + (13, 7) #G + (1, 1) #K + (2, 1)
S = 72(74, 69) Mp = 932.5(0.0) Tp = 46 A2 = 54 / 27 P = ILGLGYPSL
genpept PR = >gi|7339520|emb|CAB82850.1|(AJ250717) procathepsin E
[*Homo sapiens*] POS = 184 (SEQ ID NO: 80)

G = 2126: Mg = 936.3: Tg = 39 +− 1 #E + (1, 1) #F + (7, 5) #G + (1, 1)
S = 81(86, 72) Mp = 936.4(0.1) Tp = 40 A2 = 213 / 26 P = ALLAGSEYL
genpept PR = >gi|12653123|gb|AAH00328.1|AAH00328 (BC000328) eukaryotic
translation initiation factor 3, subunit 7 (zeta, 66 / 67 kD) [*Homo
sapiens*] POS = 439 (SEQ ID NO: 81)
G = 2146: Mg = 938.3: Tg = 38 +− 0 #FR + (2, 1)
S = 77(72, 90) Mp = 938.5(0.2) Tp = 34 A2 = 656 / 33 P = SLAELVHAV
genpept PR = >gi|4092B63|gb|AAD04812.1|(AF033122) non-p53 regulated
PA26-T1 nuclear protein [*Homo sapiens*] POS = 254 (SEQ ID NO: 62)
G = 2160: Mg = 940.4: Tg = 58 +− 1 #E + (6, 4) #F + (8, 3) #G + (1, 1) #K + (3, 2)
S = 82(80, 88) Mp = 940.6(0.2) Tp = 53 A2 = 8 / 15 P = MQPILLLL
genpept PR = >gi|181159|gb|AAB59528.1|(J03072) serine protease B
[*Homo sapiens*] POS = 1 (SEQ ID NO: 83)
G = 2176: Mg = 942.1: Tg = 48 +− 0 #G + (5, 3)
S = 74(74, 77) Mp = 942.5(0.4) Tp = 48 A2 = 2 / 12 P = GLFAPQFY
genpept PR = >gi|2062371|gb|AAB65850.1|(U70730) SnoN2 [*Homo sapiens*]
POS = 274 (SEQ ID NO: 84)
G = 2208: Mg = 944.5: Tg = 59 +− 2 #S + (2, 1) #L + (4, 2)
S = 86(94, 69) Mp = 944.5(0.0) Tp = 48 A2 = 577 / 25 P = ALWGQGTLV
genpept PR = >gi|773628|gb|AAA88873.1|(U21267) immunoglobulin mu
heavy chain [*Homo sapiens*] POS = 103 (SEQ ID NO: 85)
G = 2213: Mg = 945.4: Tg = 37 +− 1 #S + (12, 1) #E + (60, 10) #F + (6, 5)
EST + (5, 2) #FR + (11, 3) #K + (1, 1)
S = 87(97, 66) Mp = 945.5(0.1) Tp = 34 A2 = 592 / 34 P = SLLGGDVVSV
genpept PR = >gi|5231131|gb|AAD41085.1|AF153603_1 (AF153603) TSC-22
related protein [*Homo sapiens*] POS = 27 (SEQ ID N0: 7)
G = 2231: Mg = 947.3: Tg = 41 +− 1 #E + (4, 2) #FR + (1, 1) #G + (11, 6)
S = 85(88, 81) Mp = 947.3(0.0) Tp = 20 A2 = 0.0 / 18 P = DTETAVVNV
genpept PR = >gi|4883681|gb|AAD31596.1|AF057352_1 (AF057352)
hepatocellular carcinoma autoantigen [*Homo sapiens*] POS = 117 (SEQ ID
NO: 86)
G = 2233: Mg = 947.4: Tg = 34 +− 1 #S + (9, 1) #EST + (3, 2) #FR + (4, 2)
S = 90(90, 90) Mp = 947.4(0.0) Tp = 30 A2 = 70 / 23 P = NLTISDVSV
genpept PR = >gi|541680|emb|CAA56734.1|(X80761) MUCl [*Homo sapiens*]
POS = 133 (SEQ ID NO: 8) ref
G = 2241: Mg = 948.3: Tg = 58 +− 1 #E + (6, 3) #F + (4, 3) #EST + (1, 1) #FR + (3, 2) #K(5, 3)
S = 75(74, 79) Mp 948.5(0.2) Tp = 62 A2 = 203 / 21 P = ALLPIFFGA
genpept PR = >gi|13185197|emb|CAC33282.1|(AXO83359) unnamed protein
product [*Homo sapiens*] POS = 43 (SEQ ID NO: 87)
G = 2270: Mg = 951.6: Tg = 40 +− 1 #D + (11, 4) #E + (49, 10) #F + (2, 1)
EST + (3, 1) #FR + (7, 3) #G + (11, 6) #K + (4, 2) #L + (4, 2)
S = 88(93, 79) Mp = 951.5(−0.1) Tp = 33 A2 = 191 / 22 P = AMVIFKSGV
genpept PR = >gi|3929529|gb|AAC82612.1| (AF034611) intrinsic
faetor-B12 receptor precursor; cubilin [*Homo sapiens*] POS = 3371 (SEQ
ID NO: 88)
G = 2299: Mg = 954.4: Tg = 50 +− 0 #D + (1, 1) #E + (31, 9) #F + (15, 7)
EST + (5, 2) #FR + (8, 3) #G + (28, 11) #K + (16, 6) #L + (4, 2)
S = 81(89, 63) Mp = 954, 5(0.1) Tp = 49 A2 = 182 / 34 P = SLLPAIVEL
genpept PR = >gi|3603418|gb|AAC63525.1|(AF083439) protein phosphatase
2A regulatory subunit A, beta isoform [*Homo sapiens*] POS = 415 (SEQ
ID N0: 89)ref
G = 2329: Mg = 956.6: Tg = 33 +− 2 #EST + (3, 2) #FR + (5, 3)
S = 81(83, 79) Mp = 956.5(−0.1) Tp = 32 A2 = 736 / 32 P = YLGPHIASV
genpept PR = >gi|12052942|emb|CAB66646.1|(AL136711) hypothetical
protein [*Homo sapiens*] POS = 137 (SEQ ID NO: 89)
G = 2344: Mg = 958.3: Tg = 33 +− 2 #S + (6, 2) #D + (8, 2) #E + (100, 8)
G + (34, 11) #K + (4, 2)
S = 96(96, 99) Mp = 958.3(0.0) Tp = 38 A2 = 41 / 23 P = SLWGQPAEA
genpept PR = >gi|463430|gtb|AAC27816.1|(U04520) type IV collagen alpha
5 chain [*Homo sapiens*] POS = 18 (SEQ ID NO: 9)
G = 2350: Mg = 959.3: Tg = 46 +− 1 #G + (14, 7) #K + (8, 5)
S = 79(90, 54) Mp = 959.6(0.3) Tp = 45 A2 = 16 / 27 P = SLFPGQVVI
genpept PR = >gi|12654999|gb|AAH01347.1|AAH01347 (BC001347) polymerase
(DMA-directed), alpha (70kD) [*Homo sapiens*] POS = 295 (SEQ ID NO: 90)
G = 2355: Mg = 959.5: Tg = 38 +− 0 #F + (3, 2)
S = 82(80, 89) Mp = 959.5(0.0) Tp = 38 A2 = 324 / 29 P = SLLEKSLGL
genpept PR = >gi|13529002|gb|AAH05291.1|AAH05291 (BC005291) eukaryotic
translation elongation factor 1 epsilon 1 [*Homo sapiens*] POS = 8 (SEQ
ID NO: 91)
G = 2356: Mg = 959.5: Tg = 30 +− 1 #D + (3, 1) #E + (29, 9) #F + (2, 2) #EST + (7, 2)
FR + (9, 3) #G + (49, 10) #K + (6, 2)
S = 85(84, 90) Mp = 959.5(0.0) Tp = 27 A2 = 485 / 24 P = ILTDITKGV
genpept PR = >gi|181969|gb|AAA50388.1|(M19997) elongation factor 2
[*Homo sapiens*] POS = 161 (SEQ ID NO: 92)
G = 2372: Mg = 960.5: Tg = 35 +− 1 #D + (2, 1) #G + (5, 5)
S = 78(73, 90) Mp = 960.5(0.0) Tp = 34 A2 = 79 / 24 P = GLFQGKTPL
genpept PR = >gi|4589929|dbj|BAA76931.1|(AB024704) fls353 [*Homo
sapiens*] POS = 53 (SEQ ID NO: 93)
G = 2382: Mg = 962.3: Tg = 47 +− 0 #G + (5, 4)

S = 80(82, 77) Mp = 962.5(0.2) Tp = 11 A2 = 0.0 / 6 P = ESQLKKMV
genpept PR = >gi|12803337|gb|AAH02487.1|AAH02487 (BC002487) tumor
susceptibility gene 101 [Homo sapiens] POS = 5 (SEQ ID NO: 94)
G = 2434: Mg = 967.3: Tg = 54 +− 0 #G + (10, 7)
S = 83(85, 79) Mp = 967.5(0.2) Tp = 61 A2 = 139 / 19 P = FLYPFPLA
genpept PR = >gi|436224|dbj|BAA05062.1|(D26067) KIAA0033 [Homo
sapiens] POS = 185 [SEQ ID NO: 95)
G = 2446: Mg = 966.4: Tg = 20 +− 2 #F + (4, 2) #G + (19, 6)
S = 86(89, 79) Mp = 968.4(0.0) Tp = 29 A2 = 78 / 29 P = ALTGHLEEV
genpept PR = >gi|34388|emb|CAA29338.1|(X05908) lipocortin (AA 1-346)
[Homo sapiens] POS = 99 (SEQ ID NO: 96)
G = 2447: Mg = 963.4: Tg = 42 +− 1 #D + (1, 1) #E + (1, 1) #F + (11, 7) #FR + (1, 1)
G + (27, 11) #K + (6, 3) #L + (3, 2)
S = 87(87, 90) Mp = 968.4(0.0) Tp = 36 A2 = >1k / 33 P = SLLDPVPEV
genpept PR = >gi|1504020|dbj|BAA13209.1|(D86973) similar to Yeast
translation activator GCN1 (P1:A48126) [Homo sapiens] POS = 1406 (SEQ
ID N0: 97)
G = 2464: Mg = 969.5: Tg = 47 +− 0 #E + (2, 2) #F + (7, 5) #G + (25, 11)
S = 33(85, 81) Mp = 969.5(0.0) Tp = 48 A2 = 1 / 19 P = MAPQALLLL
genpept PR = >gi|1780998|emb|CAA71531.1|(Y10520) HLA-C alpha chain
(Cw*1701) [Homo sapiens] POS = 4 (SEQ ID NO: 98)
G = 2489: Mg = 971.5: Tg = 42 +− 0 #D + (9, 4) #F + (10, 6)
S = 88(91, 81) Mp = 971.4(−0.1) Tp = 42 A2 = 1 / 23 P = FSNGYLASL
genpept PR = >gi|12655065|gb|AAH01382.1|AAH01382 (6C001382) solute
carrier family 29 (nucleoside transporters), member 1 [Homo sapiens]
POS = 405 (SEQ ID NO: 99)
G = 2495: Mg = 972.4: Tg = 52 +− 1 #D + (25, 5) #E + (19, 9) #F + (24, 7)
EST + (5, 2) #FR + (8, 3) #G + (43, 11) #K + (32, 6) #L + (4, 2)
S = 91(96, 81) Mp = 972.5(0.1) Tp = 41 A2 = 656 / 30 P = TLIEDILGV
genpept PR = >gi|11121497|emb|CAC14946.1|(AL132825) dJ756N5.2 (novel
protein (DKFZp727M231) similar to Trp4-associated protein TAP1
(ABCB2)) [Homo sapiens] POS = 209 (SEQ ID N0: 100)
G = 2514: Mg = 973.4: Tg = 33 +− 1 #F + (5, 3) #G + (10, 6) #K + (4, 2) #L + (1, 1)
S = 82(84, 79) Mp = 973.4(0.0) Tp = 31 A2 = 0.0 / 17 P = IAEAVRTTL
genpept PR = >gi|2559010|gb|AAC96011.1|(AF026292) chaperonin
containing L-complex polypeptide 1, eta subunit; CCT-eta [Homo sapiens]
POS = 32 (SEQ ID NO: 101)
G = 2515: Mg = 973.5: Tg = 34 +− 1 #EST + (5, 2)
S = 80(80, 81) Mp = 973.4(−0.1) Tp = 31 A2 = 307 / 27 P = KLSELEAAL
genpept PR = >gi|12314174|emb|CAC08001.1|(AL137067) bA13B9.3 (novel
protein similar to KRT8) [Homo sapiens] POS = 368 (SEQ ID NO: 102)
G = 2522: Mg = 974.3: Tg = 30 +− 2 #S + (7, 1) #E + (3, 3) #EST + (8, 2) #FR + (11, 3)
S = 89(90, 89) Mp = 974.5(0.2) Tp = 25 A2 = 6 / 21 P = SLSVKLEQA
genpept PR = >gi|37258|emb|CAA44819.1|(X63105) Tpr [Homo sapiens]
POS = 453 (SEQ ID N0: 104)
G = 2527: Mg = 974.3: Tg = 50 +− 0 #D + (1, 1) #E + (15, 7) #F + (9, 4) #G + (22, 10) #K + (10, 5)
S = 90(98, 72) Mp = 974.5(0.2) Tp = 50 A2 = 413 / 26 P = MLLAALMIV
genpept PR = >gi|5802822|gb|AAD51798.1|AF164614_2 (AF164614) envelope
protein [Homo sapiens] POS = 76 (SEQ ID NO: 105)
G = 2537: Mg = 974.5: Tg = 53 +− 0 #F + (4, 3) #G + (13, 9) #K + (2, 2)
S−81(83, 79) Mp = 974.5(0, 0) Tp = 56 A2 = 60 / 24 P = AILPTSIFL
genpept PR = >gi|2323410|gb|AAB66581.1|(AF015913) SkblHs [Homo
sapiens] POS = 229 (SEQ ID NO: 106)
G = 2546: Mg = 975.4: Tg = 38 +− 1 #E + (3, 2) #F + (7, 4) #G + (19, 10) #K + (1, 1)
S = 82(91, 63) Mp = 975.4(0, 0) Tp = 32 A2 = 8 / 27 P = AALPNVYEV
genpept PR = >gi|12652781|gb|AAH00142.1|AAH00142 (BC000142)
minichromosome maintenance deficient (S. cerevisiae) 5 (cell
division cycle 46) [Homo sapiens] POS = 326 (SEQ ID NO: 107)
G = 2567: Mg = 977.5: Tg = 22 +− 3 #G + (9, 5)
S = 84(82, 90) Mp = 977.4(−0.1) Tp = 24 A2 = 186 / 24 P = RMLPHAPGV
genpept PR = >gi|1667394|gb|AAC50814.1|(U31B14) transcriptional
regulator homolog RPD3 [Homo sapiens] POS = 372 [SEO ID NO: 108)
G = 2610: Mg = 981.7: Tg = 36 +− 0 #S #F + (3, 2)
S = 79(80, 79) Mp = 981.6(−0.1) Tp = 38 A2 = 49 / 32 P = SLIGHLQTL
genpept PR = >gi|642013|gb|AAB06261.1|(U16996) protein tyrosine
posphatase [Homo sapiens] POS = 337 (SEQ ID NO: 10)
G = 2636: Mg = 984.5: Tg = 61 +− 1 #D + (5, 4) #E + (9, 5) #F + (12, 6) #FR#(5, 2)
G + (2, 1) #K + (12, 5) #L + (1, 1)
S = 85(91, 72) Mp = 984.7(0.2) Tp = 61 A2 = 11 / 21 P = LMVLVALIL
genpept PR = >gi|12654925|gb|AAH01309.1|AAH01309 (BC001309) Unknown
(protein for MGC:5508) [Homo sapiens] POS = 19 (SEQ ID NO: 109)
G = 2641: Mg = 984, 7: Tg = 36 +− 0 #EST + (1, 1) #FR + (2, 1)
S = 78(77, 81) Mp = 983.5(−1.2) Tp = 35 A2 = 140 / 28 P = KILPTLEAV
genpept PR = >gi|12653227|gb|AAH00382.1|AAH00382 (BC000382)
interleukin enhancer binding factor 2, 45kD [Homo sapiens] POS = 127
(SEQ ID NO: 110)
G = 2649: Mg = 965.5: Tg = 40 +− 1 #E + (5, 3) #FR + (3, 2) #G + (4, 3)
S = 84(93, 63) Mp = 985.6(0.1) Tp = 38 A2 = >1k / 33 P = ALLDRIVSV
genpept PR = >gi|1504030|dbj|BAA13214.1|(D86978) similar to a -continued C.elegans protein encoded in cosmid K12D12 (249069) [*Homo sapiens*]
POS = 1499 (SEQ ID NO: 111)
G = 2661: Mg = 986.6: Tg = 35 +− 1 #E + (3, 2) #F + (3, 2) #EST + (3, 2) #FR + (1, 1) #G + (2, 2)
S = 84(82, 89) Mp = 986.7(0.1) Tp = 35 A2 = 160 / 26 P = TLVYHVVGV
genpept PR = >gi|3540219|dbj|BAA32662.1|(D87686) KIAA0017 protein
[*Homo sapiens*] POS = 165 (SEQ ID NO: 112)
G = 2666: Mg = 987.4: Tg = 32 +− 2 #D + (1, 1) #E + (1, 1) #F + (5, 2) #G + (12, 7)
S = 77(87, 54) Mp = 987.5(0.1) Tp = 33 A2 = 131 / 26 P = YLPPATQVV
genpept PR = >gi|13325146|gb|AAH04386.1|AAH04386 (BC004386) KIAA0111
gene product [*Homo sapiens*] POS = 207 (SEQ ID NO: 113)
G = 2668: Mg = 987.4: Tg = 14 +− 13 #F + (4, 3)
S = 77(76, 81) Mp = 987.3(−0.1) Tp = 26 A2 = 0.0 / 15 P = PMEALAEQV
genpept PR = >gi|3882297|dbj|BAA34508.1|(AB016331) KIAA0788 protein
[*Homo sapiens*] POS = 569 (SEQ ID NO: 114)
G = 2671: Mg = 987.6: Tg = 29 +− 1 #F + (4, 3) #EST + (1, 1) #FR + (3, 2)
G + (11, 5)
S = 74(83, 54) Mp = 987.5(−0.1) Tp = 33 A2 = 656 / 30 P = RLSEAIVTV
genpept PR = >gi|7106848|gb|AAF36149.1|AF151063_1 (AF151063) HSPC229
[*Homo sapiens*] POS = 137 (SEQ ID NO: 115)
G = 2677: Mg = 988, 3: Tg = 13 +− 4 #E + (2, 1) #F + (7, 1) #EST + (4, 1) #G + (21, 6)
S = 88(99, 63) Mp = 988.4(0, 1) Tp = 20 A2 = 28 / 27 P = SLDQPTQTV
genpept PR = >gi|1718197|gb|AAD03462.1|(U46025) translation intiation
factor eIF-3 p110 subunit [*Homo sapiens*] POS = 834 (SEQ ID NO: 116)
G = 2692: Mg = 989.4: Tg = 41 +− 1 #S + (8, 2) #D + (13, 5) #E + (12, 6) #F + (11, 6)
EST + (4, 2) #FR + (6, 3) #G + (15, 8) #K + (13, 6)
S = 79(83, 72) Mp = 989.5(0.1) Tp = 39 A2 = 257 / 30 P = SLFPGKLEV
genpept PR = >gi|440177|gb|AAC03568.1|(U01184) flightless-I homolog
[*Homo sapiens*] POS = 1009 (SEQ ID NO: 12)
G = 2693: Mg = 989.5: Tg = 31 +− 2 #S + (15, 2) #E + (7, 3) #F + (13, 5)
EST#(3, 1) #G + (12, 7) #K + (6, 4)
S = 83(84, 81) Mp = 989.5(0.0) Tp = 35 A2 = 88 / 29 P = SLSEKTVLL,
genpept PR = >gi|180151|gb|AAA88793.1|(M84349) CD59 protein [*Homo
sapiens*] POS = 106 (SEQ ID NO: 11)
G = 2729: Mg = 993.5: Tg = 18 +− 4 #F + (2, 1) #EST + (4, 2) #FR + (8, 3) #G + (9, 4) #K + (1, 1)
S = 92(97, 81) Mp = 993.6(0.1) Tp = 22 A2 = 243 / 23 P = KLHGVNINV
genpept PR = >gi|12653083|gb|AAH00307.1|AAH00307 (BC000307) RNA
binding motif protein 4 [*Homo sapiens*] POS = 59 (SEQ ID NO: 117)
G = 2769: Mg = 999.5: Tg = 35 +− 1 #H + (5, 3) #I + (8, 4) #J + (5, 4)
S = 82(83, 81) Mp = 999.5(0.0) Tp = 39 A2 = 5 / 18 P = LVMAPRTVL
genpept PR = >gi|9738918|gb|AAF97847.1|(AF129293) MHC class I antigen
[*Homo sapiens*] POS = 2 (SEQ ID NO: 118)
G = 2773: Mg = 999.6: Tg = 45 +− 1 #D + (2, 1) #E + (15, 6) #F + (12, 7)
EST + (3, 1) #FR + (8, 3) #G + (15, 8) #K + (11, 5) #L + (1, 1)
S = 80(86, 69) Mp = 999.6(0.0) Tp = 42 A2 = 22 / 31 P = SIIGRLLEV
genpept PR = >gi|190516|gb|AAA36508.1|(M63960) protein phosphatase-1
[*Homo sapiens*] P0S = 11 (SEQ ID NO: 119)
G = 2785: Mg = 1000.5: Tg = 33 +− 1 #G + (14, 6) #K + (2, 2)
S = 77(77, 79) Mp = 1000.6(0.1) Tp = 36 A2 = 2 / 16 P = MAVALQLRV
genpept PR = >gi|11544742|emb|CAC17582.1|(AL121997) dJ1043F6.1.1
(Chediak-Higashi syndrome 1 (isoform 1)) [*Homo sapiens*] POS = 2544
(SEQ ID N0: 120)
G = 2789: Mg = 1000.6: Tg = 26 +− 2 #F + (3, 2) #EST + (2, 2) #FR + (2, 1)
G + (13, 6) #K(1, 1)
S−90(90, 90) Mp = 1000.4(−0.2) Tp = 27 A2 = 656 / 30 P = GLNEEIARV
genpept PR = >gi|2501873|gb|AAB80726.1|(AF017790)
retinoblastoma-associated protein HEC [*Homo sapiens*] POS = 330 (SEQ
ID N0: 121)
G = 2191: Mg = 1001.3: Tg = 40 +− 1 #F + (10, 5) #G + (16, 9) #K + (4, 3)
S = 78(81, 72) Mp = 1001.6(0.3) Tp = 19 A2 = 0.9 / 23 P = IMKVAQAKL
genpept PR = >gi|69418888|gb|AAF32263.1|AF170562_1 (AF170562)
ubiquitin-specific processing protease [*Homo sapiens*] POS = 875 (SEQ
ID NO: 122)
G = 2822: Mg = 1004.2: Tg = 27 +− 1 #G + (8, 5)
S = 90(91, 90) Mp = 1004.4(0.2) Tp = 30 A2 = 88 / 25 P = TLSEVTNQL
genpept PR = >gi|12053045|emb|CAB66698.1|(AL136764) hypothetical
protein [*Homo sapiens*] POS = 484 (SEQ ID NO: 123)
G = 2829: Mg = 1004.5: Tg = 38 +− 1 #F + (3, 2) #EST + (1, 1) #FR + (2, 1) #G + (9, 6)
S = 91(92, 90) Mp = 1004.6(0.1) Tp = 37 A2 = 324 / 29 P = ALFEGKVQL
genpept PR = >gi|10439712|dbj|BAB15550.1|(AK026780) unnamad protein
product [*Homo sapiens*] POS = 442 (SEQ ID NO: 124)
G = 2833: Mg = 1004, 6: Tg = 29 +− 0 #EST + (3, 1)
S = 87(87, 89) Mp = 1004.6(0.0) Tp = 31 A2 = 32 / 28 P = GLKGRVFEV
genpept PR = >gi|854179|emb|CAA60827.1|(X87373) ribosomal protein S3a
[*Homo sapiens*] POS = 61 (SEQ ID NO: 125)
G = 2835: Mg = 1005.2: Tg = 48 +− 0 #G + (3, 3)
S = 84(83, 89) Mp = 1005.5(0, 3) Tp = 42 A2 = 35 / 25 P = NIFPXPVGV
genpept PR = >gi|2822460|gb|AAC39565.1|(AF030234) splicing factor
Sipl [*Homo sapiens*] POS = 912 (SEQ ID NO: 126)
G = 2872: Mg = 1009.6: Tg = 47 +− 1 #E + (2, 1) #EST + (5, 2) #FR + (6, 3) #K + (15, 6)

-continued

S = 87(96, 66) Mp = 1009.7(0.1) Tp = 52 A2 = 3 / 18 P = LVSIVVAVPL
genpept PR = >gi|7023136|dbj|BAA91851.1|(AK001708) unnamed protein
product [Homo sapiens] POS = 23 (SEQ ID NO: 127)
G = 2881: Mg = 1010.5: Tg = 28 +− 1 #G + (8, 5)
S = 84(85, 82) Mp = 1010.5(0.0) Tp = 20 A2 = 370 / 30 P = NMYGKVVTV
genpept PR = >gi|1845267|gb|AAC51102.1|(U56402) SDPT5H [Homo sapiens]
POS = 562 (SEQ ID NO: 128)
G = 2891: Mg = 1011.5: Tg = 43 +− 1 #E + (9, 5) #F + (1, 1) #EST + (3, 2) #FR + (6, 3)
G + (13, 7) #K + (5, 3) #L + (3, 2)
S = 79(78, 82) Mp = 1011.5(0.0) Tp = 45 A2 = >1k / 31 P = LLLDVPTAAV
genpept PR = >gi|6165618|gb|AAF04618.1|AF097362_1 (AF097362)
gamma-interferon inducible lysosomal thiol reductase [Homo sapiens]
POS = 26 (SEQ ID NO: 2) ref
G = 2918: Mg = 1014.4: Tg = 48 +− 0 #D + (1, 1) #E + (16, 8) #F + (11, 7)
EST + (2, 1) #FR + (3, 2) #G + (19, 10)
S = 88(97, 68) Mp = 1014.6(0.2) Tp = 46 A2 = 160 / 32 P = SLINVGLISV
genpept PR = >gi|12653413|gb|AAH00476.1|AAH00476 (BC000476) acidic
protein rich in leucines [Homo sapiens] POS = 48 (SEQ ID NO: 129)
G = 2928: Mg = 1015.4: Tg = 56 +− 0 #E + (26, 8) #EST + (2, 1) #FR + (5, 3)
S = 92(97, 81) Mp = 1015.5(0.1) Tp = 61 A2 = 666 / 30 P = ALLGTLWEI
genpept PR = >gi|2224595|dbj|BAA20785.1|(AB002325) KJAA0327 protein
[Homo sapiens] POS = 18 (SEQ ID NO: 130)
G = 2929: Mg = 1015.4: Tg = 41 +− 1 #E + (5, 3) #EST + (4, 2) #FR + (2, 2)
G + (12, 7) #K + (5, 3)
S = 81(86, 72) Mp = 1015.5(0.1) Tp = 39 A2 = 13 / 16 P = FQDPVPLTV
genpept PR = >gi|4325107|gb|AAD17258.1|(AF119042) transcriptional intermediary
factor 1 alpha; TIFlalpha [Homo sapiens] POS = 890 (SEQ
ID N0: 131)
G = 2947: Mg = 1016.4: Tg = 45 +− 1 #E + (3, 3) #F + (8, 5) #EST + (2, 2) #FR + (3, 1)
G + (18, 10) #K + (7, 4)
S = 82(95, 54) Mp = 1016.6(0.2) Tp = 39 A2 = 512 / 28 P = GLYPNLIQV
genpept: PR = >gi|4240269|dbj|BAA74913.1|(AB020697) KIAA0890 protein
[Homo sapiens] POS = 1022 (SEQ ID NO: 132)
G = 2965: Mg = 1018.4: Tg = 23 +− 4 #D + (3, 1) #E + (2, 2) #F + (2, 2) #G + (25, 8)
S = 94(96, 90) Mp = 1018.6(0.2) Tp = 19 A2 = 79 / 26 P = VMDSKIVQV
genpept PR = >gi|913393|gb|AAC60648.1|(S75295) nucleoprotein
interactor 1, NPI-1 = SRP1 homolog (human, cervical carcinoma HeLa
cells, Peptide, 538 aa] [Homo sapiens] POS = 434 (SEQ ID NO: 133)
G = 2976: Mg = 1019.6: Tg = 46 +− 0 #D + (5, 2) #E + (6, 1) #F + (2, 2) #EST + (1, 1)
FR + (2, 1) #G + (4, 3)
S = 83(81, 90) Mp = 1019.6(0.0) Tp = 40 A2 = 745 / 32 P = ALLDKLYAL
genpept PR = >gi|7023341|dbj|BAA91929.1|(AK001830) unnamed protein
product [Homo sapiens] POS = 78 (SEQ ID NO: 134)
G = 2985: Mg = 1020.5: Tg = 45 +− 0 #D + (5, 3) #E + (3, 2) #F + (4, 3) #FR + (1, 1) #G + (7, 5)
S = 99(99, 99) Mp = 1020.5(0.0) Tp = 40 A2 = 298 / 27 P = NLASFIEQV
genpept PR = >gi|348907|gb|AAA35672.1|(L15428) 4a-carbinolamine
dehydratase [Homo sapiens] POS = 19 (SEQ ID NO: 135)
G = 2998: Mg = 1022.4: Tg = 44 +− 0 #G + (5, 3)
S = 76(70, 90) Mp = 1022.4(0.0) Tp = 43 A2 = 0.7 / 12 P = TLWVDPYE
genpept PR = >gi|1703501|gb|AAB37580.1|(U72649) BTG2 [Homo sapiens]
POS = 101 (SEQ ID NO: 136)
G = 3002: Mg = 1022.5: Tg = 45 +− 1 #S + (2, 1) #D + (3, 2) #G + (7, 4)
S = 82(83, 81) Mp = 1022.5(0.0) Tp = 42 A2 = >1k / 25 P = KIADFGWSV
genpept PR = >gi|3127068|gb|AAC77369.1|(AF059681) aerine / threonine
kinase 13 [Homo sapiens] POS = 147 (SEQ ID NO: 137)
G = 3036: Mg = 1025.5: Tg = 37 +− 1 #S #D + (1, 1) #F + (4, 2) #EST + (1, 1)
G + (5, 3)
S = 90(91, 90) Mp = 1025.6(0.1) Tp = 36 A2 = 89 / 28 P = SLLSHVEQL
genpept PR = >gi|5305429|gb|AAD41647.1|AF072933_1 (AF072933) Mad2-like
protein [Homo sapiens] POS = 114 (SEQ ID NO: 138)
G = 3041: Mg = 1026.3: Tg = 45 +− 0 #D + (7, 3) #FR + (1, 1) #G + (4, 3)
S = 84(90, 72) Mp = 1025.6(−0, 7) Tp = 38 A2 = >1k / 30 P = GLADKVYFL
genpept PR = >gi|1228049|dbj|BAA11423.1|(D78586) multifunctional
protein CAD [Homo sapiens] POS445 (SEQ ID NO: 139)
G = 3061: Mg = 1028.5: Tg = 35 +− 1 #S + (6, 2) #D + (3, 1) #E + (20, 7) #F + (8, 5)
EST + (5, 2) #FR + (5, 2) #G + (11, 7)
S = 88(92, 81) Mp = 1028.5(0.0) Tp = 32 A2 = 88 / 28 P = GLIEKNIEL
genpept PR = >gi|1632819|emb|CAA45219.1|(X63692) DNA
(cytosine-5-)-methyltransferase [Homo sapiens] POS = 425 (SEQ ID
N0: 13)
G = 3073: Mg = 1029.5: Tg = 51 +− 0 #D + (1, 1) #FR + (2, 1) #G + (5, 4) #K + (2, 1)
S = 81(78, 90) Mp = 1029.6(0.1) Tp = 35 A2 = >1k / 31 P = SLLDIIEKV
genpspt PR = >gi|1063586|gb|AAB41564.1|(L48546) tuberin [Homo
sapiens] POS = 526 (SEQ ID NO: 140)
G = 3092: Mg = 1031.4: Tg = 61 +− 1 #S + (8, 2) #D + (29, 4) #E + (10, 6) #F + (3, 1)
EST + (2, 1) #FR + (5, 2) #H + (1, 1) #K + (1, 1)
S = 84(82, 90) Mp = 1031.6(0.2) Tp = 64 A2 = 865 / 30 P = GLYPGLIWL
genpept PR = >gi|2559385|gb|AAB84111.1|(AF027292) interferon
regulatory factor 6 [Homo sapiens] POS = 21 (SEQ ID NO: 14)

```
G = 3118: Mg = 1034, 4: Tg = 60 +- 1 #D + (16, 5) #E + (45, 9) #F + (14, 7)
#EST + (2, 1) #FR + (10, 3) #G + (11, 7) #K + (7, 4)
S = 81(85, 72) Mp = 1034.6(0.2) Tp = 66 A2 = 32 / 21 P = FVFPGELLL
genpept PR = >gi|12652633|gb|AAH00062.1|AAH00062 (BC000062) solute
carrier family 1 (neutral amino acid transporter), member 5 [Homo
sapiens] POS = 89 (SEQ ID NO: 141)
G = 3127: Mg = 1036.3: Tg = 36 +- 0 #F + (2, 1)
S = 78(77, 81) Mp = 1036.6(0.3) Tp = 35 A2 = 656 / 30 P = ALNELLQHV
genpept PR = >gi|6682361|gb|AAF23322.1|AF177198_1 (AF177198) talin
[Homo sapiens] POS = 777 (SEQ ID N0: 142)ref
G = 3128: Mg = 1036.3: Tg = 36 +- 1 #G + (12, 7)
S = 83(84, 81) Mp = 1036.5(0.2) Tp = 29 A2 = 913 / 27 P = NLYEGQITV
genpept PR = >gi|1699038|gb|AAC50967.1|(U78735) ABC3 [Homo sapiens]
POS = 555 (SEQ ID NO: 143)
G = 3142: Mg = 1037.5: Tg = 43 +- 1 #EST + (2, 2) #FR + (5, 2) #G + (1, 1)
#I + (11, 5) #J + (5, 3)
S = 86(89, 79) Mp = 1037.5(0.0) Tp = 41 A2 = 0.1 / 15 P = FTKDFAPVI
genpept PR = >gi|7022824|dbj|BAA91736.1|(AK001518) unnamed protein
product [Homo sapiens] POS = 77 (SEQ ID NO: 144)
G = 3144: Mg = 1037.6: Tg = 51 +- 1 #D + (7, 3) #E + (29, 6) *F + (11, 7)
#EST + (2, 1) #FR + (4, 2) #G + (12.7) #K(3, 2) #L + (1, 1)
S = 87(86, 90) Mp = 1037.7(0.1) Tp = 53 A2 = >1k / 31 P = KLLEPVLLL
genpept PR = >gi|338447|gb|AAA60583.1|(M60854) RPS16 [Homo sapiens]
POS = 50 (SEQ ID N0: 145)ref
G = 3154: Mg = 1038.5: Tg = 48 +- 1 #D + (32, 4) #E + (48, 9) #F(7, 5)
#EST + (6, 2) #FR + (9, 3) #G + (24, 10) #K + (9, 6)
S = 81(82, 81) Mp = 1038.7(0.2) Tp = 47 A2 = 408 / 30 P = YLLPAIVHI
genpept PR = >gi|2832596|emb|CAB09792.1|(297056) dJ434P1.3 (DEAD/H
(Asp-Glu-Ala-Asp/His) box polypeptide 17 (72 kD)) [Homo sapiens]
POS = 146 (SEQ ID NO: 15) ref
G = 3183: Mg = 1041.4: Tg = 52 +- 0 #FR + (2, 1) #G + (1, 1)
S = 79(82, 72) Mp = 1041.6(0.2) Tp = 52 A2 = >1k / 23 P = GLFAPQFYV
genpept PR = >gi|2062371|gb|AAB65850.1|(U70730) SnoN2 [Homo sapiens]
POS = 274 (SEQ ID NO: 146)
G = 3191: Mg = 1042.4: Tg = 29 +- 1 #S + (2, 1) #G + (12, 6)
S = 87(90, 81) Mp = 1042.5(0.1) Tp = 27 A2 = 805 / 27 P = LMVDHVTEV
genpept PR = >gi|9930612|gb|AAG02115.1|AF293025_1 (AF293025) steroid
receptor RNA activator isoform 2 [Homo sapiens] POS = 183 (SEQ ID
NO: 147)
G = 3201: Mg = 1043.5: Tg = 58 +- 1 #E + (2, 2) #F + (6, 4) #EST + (1, 1) #FR + (2, 1)
#G + (7, 4) #K + (1, 1)
S = 85(88, 81) Mp = 1043.7(0.2) Tp = 62 A2 = 408 / 27 P = FLLPILSQI
genpept PR = >gi|2580552|gb|AAC51830.1|(AF000983) dead box, X isoform
[Homo sapiens] POS = 234 (SEQ ID NO: 148)
G = 3213: Mg = 1045.5: Tg = 58 +- 0 #E + (1, 1) #F + (2, 2) #FR + (1, 1)
S = 84(90, 72) Mp = 1044.5(-1.0) Tp = 54 A2 = 0.3 / 18 P = FLIPLNITN
genpept PR = >gi|2224611|dbj|BAA20793.1|(AB002333) K1AA0335 [Homo
sapiens] POS = 938 (SEQ ID NO: 149)
G = 3219: Mg = 1046.6: Tg = 40 +- 1 #D + (2, 2) #E + (1, 1) #F + (2, 1) #EST + (4, 1)
#FR + (5, 2) #G + (1, 1) #K + (3, 3)
S = 85(83, 90) Mp = 1046.7(0.1) Tp = 39 A2 = 243 / 30 P = NLLPKLHIV
genpept PR = >gi|4568524|gb|AAD26136.1|AF109196_1 (AF109196)
intracellular chloride channel p64Hl [Homo sapiens] POS = 190 (SEQ ID
N0: 150)
G = 3221: Mg = 1047.6: Tg = 44 +- 0 #D + (1, 1) #E + (15, 8) #F + (2, 2) #EST + (5, 2)
#FR + (7, 3) #G + (12, 6)
S = 79(82, 72) Mp = 1047.7(0.0) Tp = 50 A2 = 413 / 31 P = LLDRFLATV
genpept PR = >gi|12653303|gb|AAH00420.1|AAH00420 (BC000420) cyclin I
[Homo sapiens] POS = 72 (SEQ ID NO: 151)
G = 3240: Mg = 1049.4: Tg = 41 +- 1 #E + (3, 2) #F + (2, 2) #EST + (2, 2) #FR + (3, 3)
S = 77(79, 74) Mp = 1049.5(0.1) Tp = 36 A2 = 294 / 29 P = YLDPSVLSGV
genpept PR = >gi|505098|dbj|BAA06683.1|(D31885) KIAA0069 [Homo
sapiens] POS = 84 (SEQ ID NO: 152)
G = 3242: Mg = 1049.5: Tg = 44 +- 0 #F + (8, 6)
S = 78(85, 63) Mp = 1048.5(-1.0) Tp = 44 A2 = 378 / 27 P = LLYPTEITV
genpept PR = >gi|220141|dbj|BAA00845.1|(D01038) VLA-3 alpha subunit
[Homo sapiens] POS = 798 (SEQ ID NO: 153)
G = 3257: Mg = 1051.4: Tg = 65 +- 1 #D + (2, 2) #E + (9, 4) #F + (9, 4) #EST + (2, 1) #FR + (6, 3)
S = 88(88, 90) Mp = 1051.6(0.2) Tp = 63 A2 = >1k / 26 P = NLGDFLIFL
genpept PR = >gi|1469175|dbj|BAA09475.1|(D50916) The KIAA0126 gene is
partially related to a yeast gene. [Homo sapiens] POS = 638 (SEQ ID
NO: 154)
G = 3258: Mg = 1051.4: Tg = 54 +- 0 #D + (18, 4) #E + (10, 6) #F + (8, 5) #G + (1, 1)
#K + (3, 2)
S = 79(85, 66) Mp = 1051.5(0.1) Tp = 56 A2 = >1k / 30 P = GLYEGLTWL
genpept PR = >gi|178989|gb|AAA90928.1|(M57763) ADP-ribosylation
factor [Homo sapiens] POS = 161 (SEQ ID NO: 155)
G = 3270: Mg = 1054.3: Tg = 51 +- 0 #D + (5, 3) #E(19, 8) #F + (12, 7)
#EST + (2, 1) #FR + (5, 2)
```

-continued

S = 96(96, 99) Mp = 1054.5(0.2) Tp = 48 A2 = 437 / 19 P = SLFDLNFQA
genpept PR = >gi|189292|gb|AAB60701.1|(M81600) NAD(P)H:quinone
oxireductase [Homo sapiens] POS = 227 (SEQ ID NO: 156)
G = 3271: Mg = 1054.3: Tg = 55 +− 1 #K + (5, 2)
S = 80(77, 90) Mp = 1054.4(0.1) Tp = 43 A2 = 0.0 / 8 P = MFSLEDSII
genpept PR = >gi|809029|emb|CAA57993.1|(X82676) tyrosine phosphatase
[Homo sapiens] POS = 833 (SEQ ID N0: 157)
G = 3279: Mg = 1055.4: Tg = 37 +− 1 #G + (6, 4)
S = 76(74, 81) Mp = 1055.3(−0.1) Tp = 37 A2 = 122 / 19 P = AMWEHPITA
genpept PR = >gi|10197638|gb|AAG14955.1|AF182419_1 (AF182419) MDS018
[Homo sapiens] POS = 65 (SEQ ID NO: 158)
G = 3297: Mg = 1057.5: Tg = 17 +− 2 #G + (8, 4)
S = 95(94, 99) Mp = 1057.6(0, 1) Tp = 31 A2 = 320 / 26 P = YLGRIAHEV
genpept PR = >gi|12653485|gb|AAH00514.1|AAH00514 (BC000514) ribosomal
protein L13a [Homo sapiens] POS = 137 (SEQ ID NO: 159)
G = 3309: Mg = 1059.5: Tg = 34 +− 0 #F + (3, 3) #EST + (3, 1) #FR + (2, 1)
S = 82(84, 79) Mp = 1059.6(0.1) Tp = 30 A2 = 482 / 24 P = GL1DHQTYL
genpept PR = >gi|1477651|gb|AAB05428.1|(U63610) plectin [Homo
sapiens] POS = 4188 (SEQ ID NO: 160)
G = 3325: Mg = 1061.4: Tg = 40 +− 1 #G + (6, 3)
S = 85(87, 81) Mp = 1061.7(0.3) Tp = 31 A2 = 523 / 26 P = AIQDKLFQV
genpept PR = >gi|13543970|gb|AAH06123.1|AAH06123 (BC006123) Similar to
RIKEN CDNA 0710001P09 gene [Homo sapiens] POS = 96 (SEQ ID NO: 161)
G = 3329: Mg = 1062.4: Tg = 29 +− 1 #H + (6, 3)
S = 89(89, 89) Mp = 1062.5(0.1) Tp = 27 A2 = 0.0 / 9 P = IVKWDRDM
genpept PR = >gi|179318|gb|AAA51911.1|(M17987) beta-2-microglobulin
[Homo sapiens] POS = 112 (SEQ ID NO: 162)
G = 3331: Mg = 1062.5: Tg = 33 +− 1 #F + (9, 6) #EST + (1, 1) #G + (18, 10) #K + (4, 3)
S = 86(97, 63) Mp = 1062.6(0.1) Tp = 30 A2 = 6 / 20 P = RIIDVVYNA
genpept PR = >gi|36150|emb|CAA47670.1|(X67247) ribosomal protein S8
[Homo sapiens] POS = 77 (SEQ ID NO: 163)
G = 3342: Mg = 1064.4: Tg = 20 +− 4 #E + (1, 1) #F + (6, 4) #EST + (3, 1) #G + (16, 6)
S = 86(88, 82) Mp = 1064.6(0.2) Tp = 19 A2 = 439 / 28 P = KIVEGQVEV
genpept PR = >gi|550013|gb|AAA35654.1|(D14966) ribosomal protein L5
[Homo sapiens] POS = 117 (SEQ ID NO: 164)
G = 3364: Mg = 1066.3: Tg = 50 +− 0 #E + (3, 2) #G + (18, 10) #K + (9, 5) #L + (1, 1)
S = 81(85, 72) Mp = 1066.6(0.3) Tp = 50 A2 = 736 / 26 P = FLPSYIIDV
genpept PR = >gi|1045574|gb|AAC50293.1|(U37012) cleavage and
polyadenylation specificity factor [Homo sapiens] POS = 185 (SEQ ID
NO: 165)
G = 3384: Mg = 1068.4: Tg = 29 +− 2 #S + (8, 2) #D + (3, 1) #E + (17, 4) *F + (8, 5)
EST + (5, 2) #FR + (6, 3) #G + (18, 7) #K + (4, 2)
S = 87(90, 81) Mp = 1068.6(0.2) Tp = 29 A2 = 482 / 23 P = ALSDHHIYL
genpept PR = >gi|28597|emb|CAA28861.1|(X05236) aldolase A (AA 1-364)
[Homo sapiens] POS = 216 (SEQ ID NO: 16) ref
G = 3385: Mg = 1069.3: Tg = 37 +− 1 #F + (2, 2) #G + (7, 5)
S = 84(92, 66) Mp = 1069.3(0.0) Tp = 25 A2 = 855 / 25 P = YMMPVNSEV
genpept PR = >gi|12667401|gb|AAK01426.1|AF326731_1 (AF326731) NUF2R
[Homo sapiens] POS = 65 (SEQ ID NO: 166)
G = 3406: Mg = 1071.5: Tg = 20 +− 3 #D + (1, 1) #FR + (2, 1) #G + (20, 7)
S = 94(97, 90) Mp = 1071.6(0.1) Tp = 24 A2 = 109 / 30 P = ILDQKINEV
genpept PR = >gi|338278|gb|AAA60563.1|(M31061) ornithine
decarboxylase [Homo sapiens] POS = 23 (SEQ ID NO: 17) ref
G = 3410: Mg = 1071.6: Tg = 8 +− 8 #D + (7, 1) #F + (6, 1) #FR + (6, 1) #G + (25, 5) #K + (4, 3)
S = 94(96, 90) Mp = 1071.7(0.1) Tp = 12 A2 = 53 / 29 P = ILDKKVEKV
genpept PR = >gi|386786|gb|AAA36026.1|(J04988) 90 kD heat shock
protein [Homo sapiens] POS = 570 (SEQ ID NO: 18) ref
G = 3418: Mg = 1073.6: Tg = 5 +− 7 #F + (1, 1) #G + (3, 3)
S = 79(79, 81) Mp = 1072.5(−1.1) Tp = 5 A2 = 0.1 / 14 P = NKDLKMPKV
genpept PR = >gi|1808578|dbj|BAA07918.1|(D44466) proteasome subunit
p112 [Homo sapiens] POS = 792 (SEQ ID NO: 167)
G = 3424: Mg = 1074.6: Tg = 46 +− 0 #K + (6, 4)
S = 90(90, 90) Mp = 1074.4(−0.2) Tp = 31 A2 = 201 / 28 P = NLAEDIMRL
genpept PR = >gi|37852|emb|CAA79613.1|(Z19554) vimentin [Homo
sapiens] POS = 177 (SEQ ID NO: 168)
G = 3427: Mg = 1075.4: Tg = 46 +− 0 #D + (1, 1) #F + (8, 6)
S = 72(73, 72) Mp = 1075.6(0.2) Tp = 44 A2 = >1k / 31 P = YLPELLQTV
genpept PR = >gi|12653299|gb|AAH00418.1|AAH00418 (BC000418)
ectodermal-neural cortex (with BTB-like domain) [Homo sapiens]
POS = 228 (SEQ ID NO: 169)
G = 3470: Mg = 1080.4: Tg = 62 +− 1 #D + (13, 4) #E + (17, 8) #F + (11, 6)
EST + (2, 1) #FR + (6, 3) #G + (19, 9) #K + (10, 5) #L + (1, 1)
S = 82(82, 82) Mp = 1080.6(0.2) Tp = 69 A2 = >1k / 27 P = FLYPFPLAL
genpept PR = >gi|436224|dbj|BAA05062.1|(D26067) KIAA0033 [Homo
sapiens] POS = 185 (SEQ ID NO: 170)
G = 3472: Mg = 1080.4: Tg = 50 +− 0 #F + (13, 7) #G + (25, 11) #K + (10, 5)
S = 76(87, 52) Mp = 1080.5(0.1) Tp = 53 A2 = 182 / 33 P = SLLPPTALVGL
genpept PR = >gi|1296664|emb|CAA65774.1|(X97064) Sec23 protein [Homo
sapiens] POS = 156 (SEQ ID NO: 19)

-continued

G = 3476: Mg = 1080.7: Tg = 41 +− 1 #FR + (1, 1) #G + (5, 4)
S = 75(77, 72) Mp = 1080.6(−0.1) Tp = 38 A2 = >1k / 29 P = NLYPFVKTV
genpept PR = >gi|1263196|gb|AAA97405.1|(U37436) AICAR
formyltransferase/IMP cyclohydrolase bifunctional enzyme [Homo
sapiens] POS = 101 (SEQ ID NO: 171)
G = 3477: Mg = 1081.4: Tg = 56 +− 0 #F + (6, 3)
S = 90(87, 99) Mp = 1081.7(0.3) Tp = 57 A2 = >1k / 24 P = SVIEQLFFV
genpept PR = >gi|30140|emb|CAA34277.1|(X16155) COUP-TF [Homo sapiens]
POS = 378 (SEQ ID NO: 172)
G = 3478: Mg = 1081.4: Tg = 56 +− 0 #G + (4, 3)
S = 84(86, 81) Mp = 1080.6(−0.8) Tp = 57 A2 = >1k / 29 P = SLLEPFVYL
genpept PR = >gi|7008404|gb|AAF34999.1|(AF229840) kappa B-ras 2 [Homo
sapiens] POS = 156 (SEQ ID NO: 173)
G = 3497: Mg = 1084.7: Tg = 24 +− 3 #F + (1, 1) #EST + (3, 1) #FR + (2, 1)
S = 79(82, 72) Mp = 1084.6(−0.1) Tp = 37 A2 = 437 / 26 P = ILFGHENRV
genpept PR = >gi|5911941|emb|CAB55946.1|(AL117471) hypothetical
protein [Homo sapiens] POS = 250 (SEQ ID NO: 174) ref
G = 3505: Mg = 1086.5: Tg = 19 +− 3 #G + (18, 6)
S = 88(91, 83) Mp = 1086.7(0.2) Tp = 20 A2 = 998 / 29 P = KLQEVGQVSV
genpept PR = >gi|340307|gb|AAA36808.1|(M14648) vitronectin alpha
subunit precursor [Homo sapiens] POS = 338 (SEQ ID NO: 175)
G = 3520: Mg = 1088.6: Tg = 37 +− 1 #F + (3, 2) #EST + (2, 1) #G + (8, 5) #K + (5, 4)
S = 72(82, 49) Mp = 1088.5(−0.1) Tp = 37 A2 = 75 / 16 P = RLFDEPQLA
genpept PR = >gi|3334982|gb|AAC26984.1|AAC26984 (AC005306) R27216_1
[Homo sapiens] POS = 2 (SEQ ID NO: 176)
G = 3521: Mg = 1088.6: Tg = 44 +− 1 #G + (5, 4)
S = 70(71, 68) Mp = 1088.6(0.0) Tp = 43 A2 = 119 / 30 P = SLFPGKLEVV
genpept PR = >gi|440177|gb|AAC03568.1|(U01184) flightless-I homolog
[Homo sapiens] POS = 1009 (SEQ ID N0: 177)
G = 3526: Mg = 1089.6: Tg = 50 +− 1 #S + (10, 1)
S = 84(91, 68) Mp = 1089.6(0, 0) Tp = 57 A2 = 37 / 23 P = VMLGTPFLVR
genpept PR = >gi|4589536|dbj|BAA76790.1|(AB023163) KIAA0946 protein
[Homo sapiens] POS = 340 (SEQ ID NO: 178)
G = 3533: Mg = 1091.4: Tg = 15 +− 2 #G + (12, 4)
S = 86(95, 68) Mp = 1091.4(0.0) Tp = 13 A2 = 80 / 20 P = GVYDGEEHSV
genpept PR = >gi|4102749|gb|AAD01565.1|(AF015766) MAGE XP-2 protein
[Homo sapiens] POS = 231 (SEQ ID NO: 20)
G = 3545: Mg = 1094.4: Tg = 50 +− 1 #E + (22, 9) #F + (16, 7) #EST + (4, 2)
FR + (4, 2) #G + (50, 11) #K + (11, 6) #L + (2, 2)
S = 80(89, 59) Mp = 1094.5(0.1) Tp = 49 A2 = 182 / 33 P = SLLPPDALVGL
genpept PR = >gi|13529299|gb|AAH05404.1|AAH05404 (BC005404) Unknown
(protein for MGC:5020) [Homo sapiens] POS = 156 (SEQ ID N0: 21)
G = 3563: Mg = 1098.3: Tg = 38 +− 1 #D + (7, 3) #E + (10, 6) #F + (5, 4) #EST + (3, 2)
FR + (4, 2) #G + (12, 8)
S = 88(88, 90) Mp = 1098.4(0.1) Tp = 30 A2 = 280 / 26 P = SLYDYNPNL
genpept PR = >gi|3337383|gb|AAC27426.1|(AC002544) Translation
initiation factor eIF-p110 [Homo sapiens] POS = 381 (SEQ ID NO: 179)
G = 3566: Mg = 1098.6: Tg = 50 +− 0 #E + (6, 3) #EST + (3, 1) #FR + (2, 1)
S = 92(89, 56) Mp = 1098.7(0.1) Tp = 62 A2 = 194 / 25 P = FLLGPRLVLA
genpept PR = >gi|887368|gb|AAC42003.1|(L40397) ORF; putative [Homo
sapiens] POS = 31 (SEQ ID NO: 160)
G = 3579: Mg = 1101.4: Tg = 34 +− 1 #F + (5, 4) #G + (2, 2)
S = 88(91, 33) Mp = 1101.4(0.0) Tp = 35 A2 = 502 / 24 P = FLYTGEGDTV
genpept PR = >gi|1184320|gb|AAC50373.1|(045880) X-linked inhibitor of
apoptosis protein [Homo sapiens] POS = 52 (SEQ ID NO: 181)
G = 3588: Mg = 1102.6: Tg = 34 +− 1 #E + (1, 1) #EST + (4, 2) #FR + (2, 2)
S = 82(83, 81) Mp = 1102.6(0.0) Tp = 27 A2 = >1k / 26 P = KLNPQQFEV
genpept PR = >gi|624704|gb|AAB05994.1|(L38961) putative transmembrane
protein precursor [Homo sapiens] POS = 289 (SEQ ID NO: 182)
G = 3596: Mg = 1103.4: Tg = 28 +− 2 #F + (3, 2) #G + (1, 1)
S = 88(94, 74) Mp = 1103.4(0.0) Tp = 23 A2 = 140 / 27 P = SLADLQNDEV
genpept PR = >gi|854179|emb|CAA60827.1|(X87373) ribosomal protein S3a
[Homo sapiens] POS = 70 (SEQ ID NO: 183)
G = 3603: Mg = 1104.7: Tg = 45 +− 0 #D + (1, 1) #F + (4, 3) #EST + (3, 1) #FR + (5, 2)
S = 85(99, 54) Mp = 1104.7(0, 0) Tp = 40 A2 = >364 / 28 P = RLLDYVVNI
genpept PR = >gi|7023768|dbj|BAA92081.1|(AK002094) unnamed protein
product [Homo sapiens] POS = 172 (SEQ ID NO: 184)
G = 3629: Mg = 1113.5: Tg = 35 +− 1 #G + (10, 6) #K + (10, 5)
S = 77(76, 81) Mp = 1113.6(0.1) Tp = 31 A2 = 46 / 21 P = FVDDYTVRV
genpept PR = >gi|1923256|gb|AAC51866.1|(U86782) 26S
proteasome-associated padl homolog [Homo sapiens] POS = 61 (SEQ ID
NO: 185)
G = 3637: Mg = 1115.4: Tg = 55 +− 1 #E + (29, 8) #F + (14, 7) #EST + (2, 1)
FR + (4, 2) #G + (9, 5) #L + (1, 1)
S = 82(90, 66) Mp = 1115.5(0.1) Tp = 61 A2 = >1k / 29 P = SLFEGTWYL
genpept PR = >gi|12653065|gb|AAH00297.1|AAH00297 (BC000297)
3-hydroxy-3-methylglutaryl-Coenzyme A synthase 1 (soluble) [Homo
sapiens] POS = 447 (SEQ ID NO: 186)
G = 3652: Mg = 1119.5: Tg = 56 +− 0 #D + (4, 3)

-continued

S = 80(84, 72) Mp = 1119.7(0.2) Tp = 57 A2 = 512 / 27 P = ALYNWLIQV
genpept PR = >gi|3288447|emb|CAA07553.1|(AJ007558) nucleoporin 155
[Homo sapiens] POS = 1038 (SEQ ID NO: 187)
G = 3653: Mg = 1119.6: Tg = 30 +− 1 #D + (1, 1) #F + (3, 2) #EST + (1, 1) #FR + (2, 1) #G + (10, 5)
S = 80(84, 72) Mp = 1119.7(0.1) Tp = 30 A2 = 97 / 25 P = VLIDYQRNV
genpept PR = >gi|2626840|dbj|BAA23415.1|(D89729) CRM1 protein [Homo sapiens] POS = 784 (SEQ ID NO: 188)
G = 3658: Mg = 1121.3: Tg = 49 +− 0 #S + (9, 2) #D + (7, 3) #E + (8, 5) #F + (14, 7) #G + (26, 11) #K + (2, 2) #L + (1, 1)
S = 84(81, 91) Mp = 1121.5(0.2) Tp = 47 A2 = 577 / 24 P = TLWVDPYEV
genpept PR = >gi|1703501|gb|AAB37580.1|(072649) BTG2 [Homo sapiens]
POS = 101 (SEQ ID NO: 22) ref
G = 3683: Mg = 1128.3: Tg = 51 +− 0 #S #G + (17, 9) #K + (2, 1)
S = 86(88, 82) Mp = 1128.5(0.2) Tp = 55 A2 = 348 / 25 P = FTWEGLYNV
genpept PR = >gi|1276912|gb|AAC50450.1|(044839) UHX1 protein [Homo sapiens] POS = 353 (SEQ ID NO: 189)
G = 3694: Mg = 1133.6: Tg = 25 +− 3 #D + (2, 1) #F + (1, 1) #G + (7, 3)
S = 85(87, 81) Mp = 1133.7(0.1) Tp = 30 A2 = >1k / 32 P = ILMEHIHKL
genpept PR = >gi|298486|gb|AAB25672.1|(S56985) ribosomal protein L19
[human, breast cancer cell line, MCF-7, Peptide, 196 aa] [Homo sapiens] POS = 137 (SEQ ID NO: 190) ref
G = 3697: Mg = 1134.6: Tg = 42 +− 1 #E + (12, 6) #F + (1, 1) #EST + (3, 1) #FR + (3, 1) #G + (9, 5) #K + (13, 6) #L + (1, 1)
S = 81(93, 53) Mp = 1134.6(0.0) Tp = 37 A2 = 193 / 26 P = RLDELGGVYL
genpept PR = >gi|13374901|emb|CAC34517.1|(AL031659) dJ343K2.2.3 (ribophorin II (isoform 3)) [Homo sapiens] POS = 185 (SEQ ID NO: 191)
G = 3711: Mg = 1140.6: Tg = 40 +− 1 #EST + (1, 1) #FR + (1, 1) #G + (1, 1)
S = 89(93, 82) Mp = 1140.7(0.1) Tp = 40 A2 = 526 / 27 P = KLLSKFYEL
genpept PR = >gi|10439903|dbj|BAB15591.1|(AK026930) unnamed protein product [Homo sapiens] POS = 231 (SEQ ID NO: 192)
G = 3721: Mg = 1145.4: Tg = 49 +− 1 #S + (7, 1) #F + (2, 2) #G + (14, 10)
S = 79(83, 70) Mp = 1145.5(0.1) Tp = 50 A2 = >1k / 23 P = FLFDGSPTYV
genpept PR = >gi|1049053|gb|AAC50259.1|(026644) encodes region of fatty acid synthase activity; FAS; multifunctional protein [Homo sapiens] POS = 2329 (SEQ ID N0:23)
G = 3728: Mg = 1147.5: Tg = 48 +− 1 #E + (3, 2) #EST + (2, 1) #FR + (5, 2) #G + (4, 3) #K + (13, 6)
S = 91(92, 90) Mp = 1147.7(0.2) Tp = 45 A2 = 1k: / 20 P = KVLDFEHFL
genpept PR = >gi|189022|gb|AAA36348.1|(M22920) smooth muscle mysoin light chain [Homo sapiens] POS = 28 (SEQ ID NO: 193)
G = 3743: Mg = 1152.6: Tg = 47 +− 0 #D + (5, 3) #F + (1, 1)
S = 79(82, 72) Mp = 1151.6(−1.0) Tp = 43 A2 = >1k / 24 P = YLPEDFIRV
genpept PR = >gi|2653877|gb|AAB87669.1|(AF026273) interleukin-1 receptor-associated kinase-2; IRAK-2 [Homo sapiens] POS = 381 (SEQ ID N0: 194)
G = 3754: Mg = 1156.5: Tg = 35 +− 1 #G + (3, 2) #K + (8, 5)
S = 91(95, 83) Mp = 1156.5(0.0) Tp = 43 A2 = 403 / 28 P = FLSEHPNVTL
genpept PR = >gi|5102831|emb|CAB45270.1|(AL022318) bK150C2.2 (Phorbolin 3) [Homo sapiens] POS = 107 (SEQ ID NO: 195)
G = 3806: Mg = 1210.4: Tg = 42 +− 1 #E + (7, 4) #EST + (1, 1) #FR + (5, 3) #G + (20, 11) #K + (10, 6) #L + (4, 2)
S = 76(80, 68) Mp = 1210.6(0.2) Tp = 44 A2 = 128 / 21 P = LLLDVPTAAVQA
genpept PR = >gi|6165618|gb|AAF04618.1|AF097362_1 (AF097362) gamma-interferon inducible lysosomal thiol reductase [Homo sapiens]
POS = 26 (SEQ ID NO: 3) ref
G = 3831: Mg = 1258.5: Tg = 54 +− 1 #S + (12, 2) #E + (12, 6) #F + (12, 6) #EST + (1, 1) #FR + (7, 3) #G + (20, 10) #H + (1, 1) #K + (10, 5)
S = 87(96, 68) Mp = 1258.6(0.1) Tp = 58 A2 = 611 / 27 P = FLFDGSPTYVL
genpept PR = >gi|1049053|gb|AAC50259.1|(U26644) encodes region of fatty acid synthase activity; FAS; multifunctional protein [Homo sapiens] POS = 2329 (SEQ ID NO: 24)
G = 3859: Mg = 1360.4: Tg = 44 +− 1 #E + (3, 2) #G + (19, 10)
S = 91(99, 75) Mp = 1360.6(0, 2) Tp = 42 A2 = >1k / 28 P = ALWDIETGQQTV
genpept PR = >gi|306785|gb|AAA35922.1|(M16538) G protein beta subunit [Homo sapiens] POS = 167 (SEQ ID NO: 25)

DISCUSSION

Among the thousands of different peptides presented within the context of the MHC class-I on cancer cells, only a few may eventually become candidates for the development of anti-cancer vaccines. The identification of such cancer specific peptides depends on sequencing a relatively large number of peptides.

While reducing the present invention to practice, a novel method was developed to identify candidate peptides for the development of anti-cancer vaccines. The novel method involves expressing the soluble extra-cellular domain of the MHC molecules that are simple to purify and the recovery, from them, large amounts of MHC bound peptides ready for identification by ESI-MS/MS.

Purification of the extra-cellular domain of MHC was previously achieved by truncating its entire transmembrane and cytoplasmic domains [30], by using a non-functional transmembrane domain such as Q10$^b$ [24] or fusing the extra-cellular domains to soluble secreted proteins such as antibodies Fc domains [31, 32]. Such sMHC molecules were produced in cultured cells of murine [33], human [30, 34] or insect [35] and in bacteria [36]. The soluble MHC molecules expressed by the murine or the human cells were capable of binding to their cognate TCRs, indicating the presence of bound authentic peptides that mediate this interaction [33, 37]. Bound peptides recovered from the secreted murine MHC H-2 Ld were analyzed by Edman sequencing [38]. More recently, peptides recovered from the murine Q2/Q10$^b$, which is a natural mutation resulting in the formation of soluble and secreted MHC molecules, were analyzed by ESI-MS/MS [39]. The results, however, were very disappointing as only six peptides were recovered from 50 liters of culture medium [39].

While culture cancer cell lines are invaluable model for cancer research, only a limited number of good model lines are available for the study of tumor immunology since some of the better model cell lines have rare MHC haplotypes or down regulated MHC expression altogether. The introduction of foreign MHC into such cells in accordance with the teachings of the present invention facilitates the use of the desired model cell lines for the search for cancer specific MHC bound peptides. The recovery of secreted MHC from the growth medium helps to sidestep possible interference by the cell's background MHC haplotypes.

The number of peptides identifiable during each ESI-MS/MS run performed in accordance with the present invention was limited by the rate the mass spectrometers can switch between measuring the full spectrum to performing CID, which was about four seconds. Therefore, during a chromatography of ninety minutes, around a thousand different peptides could be mass measured and fragmented. The elution order of most of the peptides recovered for MHC of a particular type and resolved in different chromatography runs was similar. Therefore, their masses and CID data were combined in order to improve their signal-to-noise ratio.

About one thousand different molecules that are certainly peptides have been fragmented at least twice in all the different chromatographs and out of these about two hundreds different peptides have been identified at high certainty. Most of these peptides were derived from housekeeping proteins and only a few were derived from proteins related to cancer. To increase the likelihood of identifying more new cancer specific peptides, the total number of identified peptides should be further enlarged. Identification of large number of peptides is currently limited by both the availability of sufficient amounts of peptides, by the capabilities of the mass spectrometers and by the non-completeness of the databanks. With the expected near availability of the entire human genome sequence, it is expected that more of the peptides will be identifiable, excluding mutant peptides that will still need to be sequenced de novo.

The soluble and secreted MHC molecules described here present similar patterns of peptides as do the original cell surface MHC. This conclusion emanates from the observation that most of these peptides, posses an amino acid sequence that fit the known sequence consensus of HLA-A2.1 and of B7 (see score columns in Table 8 above). Some of the peptides have been identified previously as MHC bound peptides and thus indicate the validity of the methodology of the present invention. The most significant advantage of the use of secreted MHC as a source for peptides for analysis has to do with the order of magnitude larger recovery of sMHC molecules and therefore peptides per cell over the alternative purification from detergent solubilized cells and the purified sMHC molecules were free of interfering cellular debris and detergents.

Direct biochemical analysis of peptides eluted from MHC molecules that are recovered from cancer cells, allows unbiased identification of those peptides that are actually presented by the MHC. Even though, identifying putative MHC bound peptides using computer programs based on the consensus motifs followed by synthesizing them and testing their immunogenicity, bypasses the reliance on expensive and technically demanding mass-spectrometry needed for biochemical analysis of MHC bound peptides. However, the motif prediction approach is dependent on the availability of well-established consensus for the MHC allele of interest and is hampered by the difficulty of taking into account the processing machinery involved in generating the peptides and transporting them to the MHC [13]. Moreover, it was suggested that contaminating protecting groups inadvertently left on the synthetic peptides are very immunogenic and may become the target for the activity of the CTLs. The CTLs generated in vitro are often low affinity binders and incapable of recognizing the rare peptides actually presented by the cancer cells in vivo [10].

The examples of identified peptides listed in Table 8 above include peptides that do not fit the accepted consensus of MHC bound peptides presented by the studied MHC haplotypes. Peptides longer than ten amino acids are not expected to be common among MHC class-I peptides [40, 41]. However, in this study, few peptides of 11 amino acids p1210, SEQ ID NO:3 and p1258, SEQ ID NO:24) and 12 amino acids (p1360, SEQ ID NO:25) long were observed among the identified peptides. The computer programs for motif predictions of class-I peptides are not able to predict such peptides as their length is outside the consensus [42, 43]. The detection of longer peptides among the peptides in the natural mixture suggests that the consensus motif should possibly be extended to include such outliers. Another interesting observation is the relatively abundance of peptides that originated from overlapping parts of the proteins with one or two amino acids difference in length, such as p800 (SEQ ID NO:4) and p913 (SEQ ID NO:5) from β-catenin, p1145 (SEQ ID NO:23) and p1258 (SEQ ID NO:24) from fatty acid synthase, p898 (SEQ ID NO:1), p1011 (SEQ ID NO:2) and p1210 (SEQ ID) NO:3) from IP30 (Table 8). Moreover, peptides p1080 (SEQ ID NO:19) and p1094 (SEQ ID NO:21) are derived from homologous site in two alleles of the same protein. This observation points to the existence of structural hotspots for generation of peptides, possibly as a result of heath-shock proteins binding and protection from complete proteolysis of these regions. Differences in length could also result from incomplete trimming of the peptides in the endoplasmic reticulum [44, 45].

Interesting observations are the large similarities between the patterns of peptides produced by cell lines of different tissue origin and on the other hand, the presence of a few peptides that are unique to one type of cancer cells. The ability to characterize the similarities and differences between peptide patterns of different cell lines and growth conditions and between different HLA haplotypes are among the most important possible uses of the novel methodology presented herein.

The most effective mean to ascertain the identity of the amino acid sequences of peptides that were identified by this method is to compare their retention times, their exact masses and their CID data to those of the corresponding synthetic peptides [16, 39, 46, 47]. The sequences of all the peptides that were identified at high confidence by searching the databank with their mass spectrometry data were shown to be correct when these parameters were compared with the corresponding synthetic peptides.

A number of peptides identified here were derived from known tumor antigens. Those peptides that attracted the attention as possibly cancer specific were chemically synthesized and tested again. The fact that a few of them elicited a CTL response in mice may point to their possible immunogenicity in human.

Tumor proteins from which identified peptides were derived included mucin (MUC1), a well-studied tumor-associated antigen that is up regulated in breast and ovarian carcinomas [48]. A number of HLA-A2.1 restricted MUC1-derived CTL epitopes were identified by the motif prediction approach [26, 49–52]. Peptide p947 (NLTISDVSV, SEQ ID NO:8) identified here from breast carcinoma cells (MCF-7) is the same peptide that was predicted and confirmed to be a HLA-A2 antigen originating from MUC1 by Carmon et al. [26].

Another peptide derived from a known tumor antigen, was p1091 (SEQ ID NO:20) from the testis-cancer antigen MAGE-B2. It belongs to a group of 21 known genes that are essentially silent in most normal cells except for testis and placental trophobalsts and since different member of the MAGE proteins are expressed in a variety of tumors, they attracted significant attention as cancer vaccine candidates [53–57]. A few peptides were identified so far from the MAGE proteins by genetic approach and by predicting their sequence based on the known motifs rather than by the biochemical approach [27, 28, 58–61] (reviewed in [10]). The identification of the novel MAGE-B2 derived peptide p1091 (GVYDGEEHSV) (SEQ ID NO:20) by the direct biochemical approach is a very encouraging observation that confirmed the validity of this method for identification of novel tumor specific antigens. Homologous peptides from MAGE-A4 and MAGE-A10 proteins were previously identified as MHC bound peptides and tested for their immunogenicity (see FIG. 4D). This suggests the existence of a possible hot spot within the MAGE protein for processing as MHC bound peptides [27, 28].

Peptides derived from other proteins that are involved with cancer progression and may also serve as candidates for anti-cancer vaccines of diagnosis include p913 (SEQ ID NO:5) from β-catenin, which is normally involved in cellular adhesion, signal transduction and as a transcription enhancer with a possible oncogenic role in colorectal cancer. Abnormal high amounts of the protein were found in the cytoplasm in cancer cells instead of the intracellular boundary in normal cells and this abnormal behavior was correlated with metastasis [62–64]. Peptide p1145 (SEQ ID NO:23) and p1258 (SEQ ID NO:24) is derived form fatty acid synthase (FAS), a biosynthetic enzyme expressed in liver and lactating breasts and is a marker of poor prognosis when expressed in colon, prostate, ovarian, breast and endometrial cancers. Its significance for cancer is was established by inhibiting it activity, which leads to apoptosis in cancer cells [65–69]. The enzyme DNA methyl transferase (MTDM) is the source protein for p1028 (SEQ ID NO:13) an enzyme that is highly expressed in different cancer cell types, including prostate and breast [70–72]. Increased MTDM activity is usually associated with tumor progression and is considered to be an important event in cell transformation [71, 73].

Once tumor specific MHC bound peptides are identified and their ability to stimulate an immune response is demonstrated, such peptides become candidates for adoptive immunotherapy. Identification of peptides originating from normal proteins that are uniquely expressed in non-vital organs, such as breast, prostate and ovaries can become very useful for immunotherapy of these cancers. The potential usefulness of identified immunogenic peptides should be evaluated by the presence of specific T cells directed against them in patients inflicted with the particular cancer using standard assays such as ELISPOT and CTL. The assay of immunizing mice with the peptides described herein was meant to serve first as validation that these peptides are indeed MHC bound peptides with affinity for the HLA-A2.1 and as the preliminary indication of their immunogenic potential.

Secreted soluble MHC such as described herein can also be used for analysis of peptides presented by cells involved with pathologies other than cancer, such as autoimmune diseases and viral infections with the aims of identifying peptides of significance for treating these diseases. The method can also be used for identifications of MHC bound peptides presented on normal cells of specific tissues, peptides presented by particular MHC alleles and peptides originating from expression of particular proteins of interest. Moreover, the approach can be used for analysis of MHC bound peptides derived from over-expression of specific proteins, from induced, mutations, as a result of metastasis progression and as a way for searching for peptides derived from signal peptides of cell surface proteins. The approach described in this study is also useful for comparisons between patterns of MHC bound peptides induced by minor changes in the cells growth conditions such as the addition of hormones, the expression of a foreign protein or under stress conditions.

Therefore, an appealing outcome of the methodology described herein is that the simple expression of different recombinant MHC molecules in different cell lines in a soluble, secreted form and their easy recovery from the growth medium with their peptides still attached, followed by comprehensive analysis of the peptides may become a good staging point for above listed ambitious research projects. Such 'human MHC-peptide projects' are worthy goals to follow the human genome and proteome projects.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Pamer, E. and P. Cresswell, Mechanisms of MHC class I-restricted antigen processing, Annu. Rev. Immunol., 1998. 16:p. 323–58.
2. Hunt, D. F., et al., Characterization of peptides bound to the class I MHC molecule HLA-A2.1 by mass spectrometry. Science, 1992. 255(5049): p. 1261–3.

3. Falk, K., et al., Allele-specific motifs revealed by sequencing of self-peptides eluted from MHC molecules. Nature, 1991. 351(6324); p. 290–6.
4. Pamer, E. G., J. T. Harty, and M. J. Bevan, Precise prediction of a dominant class I MHC-restricted epitope of Listeria monocytogenes. Nature, 1991. 353(6347): p. 852–5.
5. Cox, A. L., et al., Identification of a peptide recognized by five melanoma-specific human cytotoxic T cell lines. Science, 1994. 264(5159): p. 716–9.
6. Storkus, W. J., et al., Identification of T-cell epitopes: rapid isolation of class I-presented peptides from viable cells by mild acid elution. J. Immunother., 1993. 14(2): p. 94–103.
7. de Jong, A., Contribution of mass spectrometry to contemporary immunology. Mass Spectrom. Rev., 1998. 17(5): p. 311–35.
8. Rosenberg, S. A., New opportunities for the development of cancer immunotherapies. Cancer J. Sci. Am., 1998. 4 Suppl 1. p. S1–4.
9. Boon, T., P. G. Coulie, and B. Van den Eynde, Tumor antigens recognized by T cells. Immunol. Today., 1997. 18(6): p. 267–8.
10. Van den Eynde, B. J. and P. van der Bruggen, T cell defined tumor antigens. Curr. Opin. Immunol., 1997. 9(5): p. 684–93.
11. Boon, T., Tumor antigens recognized by cytolytic T lymphocytes: present perspectives for specific immunotherapy. Int. J. Cancer, 1993. 54(2): p. 177–80.
12. Zhang, C., A. Anderson, and C. DeLisi, Structural principles that govern the peptide-binding motifs of class I MHC molecules. J. Mol. Biol., 1998. 281(5): p. 929–47.
13. Buus, S., Description and prediction of peptide-MHC binding: the 'human MHC project'. Curr. Opin. Immunol., 1999. 11(2): p. 209–13.
14. Zarling, A. L., et al., Phosphorylated peptides are naturally processed and presented by major histocompatibility complex class I molecules In vivo. J. Exp. Med., 2000. 192(12): p. 1755–62.
15. Pierce, R. A., et al., Cutting edge: the HLA-A*0101-restricted HY minor histocompatibility antigen originates from DFFRY and contains a cysteinylated cysteine residue as identified by a novel mass spectrometric technique. J. Immunol., 1999. 163(12): p. 6360–4.
16. Skipper, J. C., et al., An HLA-A2-restricted tyrosinase antigen on melanoma cells results from posttranslational modification and suggests a novel pathway for processing of membrane proteins. J. Exp. Med., 1996. 183(2): p. 527–34.
17. Townsend, A., et al., Association of class I major histocompatibility heavy and light chains induced by viral peptides. Nature, 1989. 340(6233): p. 443–8.
18. Altman, J. D., et al., Phenotypic analysis of antigen-specific T lymphocytes. Science, 1996. 274(5284); p. 94–6.
19. Schmittel, A., U. Keilholz, and C. Scheibenbogen, Evaluation of the interferon-gamma ELISPOT-assay for quantification of peptide specific T lymphocytes from peripheral blood. J. Immunol. Methods, 1997. 210(2): p. 167–74.
20. Kawakami, Y., et al., Identification of a human melanoma antigen recognized by tumor-infiltrating lymphocytes associated with in vivo tumor rejection. Proc. Natl. Acad. Sci. USA, 1994. 91(14): p. 6458–62.
21. Flad, T., et al., Direct identification of major histocompatibility complex class I-bound tumor-associated peptide antigens of a renal carcinoma cell line by a novel mass spectrometric method. Cancer Res., 1998. 58(24): p. 5803–11.
22. van Els, C. A., et al., A single naturally processed measles virus peptide fully dominates the HLA-A*0201-associated peptide display and is mutated at its anchor position in persistent viral strains. Eur. J. Immunol., 2000. 30(4): p. 1172–81.
23. Pascolo, S., et al., HLA-A2.1-restricted education and cytolytic activity of CD8(+) T lymphocytes from beta2 microglobulin HLA-A2.1 monochain transgenic H-2 Db beta2 m double knockout mice. J. Exp. Med., 1997. 185(12): p. 2043–51.
24. Margulies, D. H., et al., Genetic engineering of an H-2 $Dd/Q10^b$ chimeric histocompatibility antigen: purification of soluble protein from transformant cell supernatants. Proc. Natl. Acad. Sci. USA, 1986. 83(14): p. 5252–6.
25. Yates, J. R., 3rd, et al., Method to compare collision-induced dissociation spectra of peptides: potential for library searching and subtractive analysis. Anal. Chem., 1998. 70(17): p. 3557–65.
26. Carmon, L., et al., Novel breast-tumor-associated MUC1-derived peptides: characterization in Db-/-xbeta2 microglobulin null mice transgenic for a chimeric HLA-A2.1/Db-beta2 microglobulin single chain. Int. J. Cancer, 2000. 85(3): p. 391–7.
27. Huang, L. Q., et al., Cytolytic T lymphocytes recognize an antigen encoded by MAGE-A10 on a human melanoma. J. Immunol., 1999. 162(11): p. 6849–54.
28. Duffour, M. T., et al., A MAGE-A4 peptide presented by HLA-A2 is recognized by cytolytic T lymphocytes. Eur. J. Immunol., 1999. 29(10): p. 3329–37.
29. Parkhurst, M. R., et al., Improved induction of melanoma-reactive CTL with peptides from the melanoma antigen gp100 modified at HLA-A*0201-binding residues. J. Immunol., 1996. 157(6): p. 2539–48.
30. Grumet, F. C., et al., Soluble form of an HLA-B7 class I antigen specifically suppresses humoral alloimmunization. Hum. Immunol., 1994. 40(3): p. 228–34.
31. Dal Porto, J., et al., A soluble divalent class I major histocompatibility complex molecule inhibits alloreactive T cells at nanomolar concentrations. Proc Natl Acad Sci USA, 1993. 90(14): p. 6671–5.
32. Cullen, C. M., et al., A Divalent Major Histocompatibility Complex/IgG1 Fusion Protein Induces Antigen-Specific T Cell Activation in Vitro and in Vivo. Cell. Immunol., 1999. 192(1): p. 54–62.
33. Schneck, J., et al., Inhibition of an allospecific T cell hybridoma by soluble class I proteins and peptides: estimation of the affinity of a T cell receptor for MHC. Cell, 1989. 56(1): p. 47–55.
34. Hansen, B., et al., Purified truncated recombinant HLA-B7 molecules abrogate cell function in alloreactive cytotoxic T lymphocytes by apoptosis induction. Transplantation, 1998. 66(12): p. 1818–22.
35. Godeau, F., et al., Purification and ligand binding of a soluble class I major histocompatibility complex molecule consisting of the first three domains of H-2 Kd fused to beta 2-microglobulin expressed in the baculovirus-insect cell system. J. Biol. Chem., 1992. 267(34): p. 24223–9.
36. Garboczi, D. N., D. T. Hung, and D. C. Wiley, HLA-A2-peptide complexes: refolding and crystallization of molecules expressed in *Escherichia coli* and complexed with single antigenic peptides. Proc. Natl. Acad. Sci. USA, 1992. 89(8): p. 3429–33.
37. Mage, M. G., et al., A recombinant soluble, single-chain class I major histocompatibility complex molecule with biological activity. Proc. Natl. Acad. Sci. USA, 1992. 89(22): p. 10658–62.

38. Corr, M., et al., Endogenous peptides of a soluble major histocompatibility complex class I molecule, H-2 Lds: sequence motif, quantitative binding, and molecular modeling of the complex. J. Exp. Med., 1992. 176(6): p. 1681–92.
39. Zappacosta, F., et al., The murine liver-specific nonclassical MHC class I molecule Q10 binds a classical peptide repertoire. J. Immunol., 2000. 164(4): p. 1906–15.
40. Stryhn, A., et al., Longer peptide can be accommodated in the MHC class I binding site by a protrusion mechanism. Eur. J. Immunol., 2000. 30(11): p. 3089–99.
41. Henderson, R. A., et al., HLA-A2.1-associated peptides from a mutant cell line: a second pathway of antigen presentation. Science, 1992. 255(5049): p. 1264–6.
42. Parker, K. C., M. A. Bednarek, and J. E. Coligan, Scheme for ranking potential HLA-A2 binding peptides based on independent binding of individual peptide sidechains. J. Immunol., 1994. 152(1): p. 163–75.
43. Rammensee, H., et al., SYFPEITHI: database for MHC ligands and peptide motifs. Immunogenetics, 1999. 50(3–4): p. 213–9.
44. Falk, K., O. Rotzschke, and H. G. Rammensee, Cellular peptide composition governed by major histocompatibility complex class I molecules. Nature, 1990. 348(6298): p. 248–51.
45. Paz, P., et al., Discrete proteolytic intermediates in the MHC class I antigen processing pathway and MHC I-dependent peptide trimming in the ER. Immunity, 1999. 11(2): p. 241–51.
46. Schirle, M., et al., Identification of tumor-associated MHC class I ligands by a novel T cell-independent approach. Eur. J. Immunol., 2000. 30(8): p. 2216–25.
47. Brockman, A. H., R. Orlando, and R. L. Tarleton, A new liquid chromatography/tandem mass spectrometric approach for the identification of class I major histocompatibility complex associated peptides that eliminates the need for bioassays. Rapid. Commun. Mass. Spectrom., 1999. 13(11): p. 1024–30.
48. Graham, R. A., J. M. Burchell, and J. Taylor-Papadimitriou, The polymorphic epithelial mucin: potential as an immunogen for a cancer vaccine. Cancer Immunol. Immunother., 1996. 42(2): p. 71–80.
49. Apostolopoulos, V., J. S. Haurum, and I. F. McKenzie, MUC1 peptide epitopes associated with five different H-2 class I molecules. Eur. J. Immunol., 1997. 27(10): p. 2579–87.
50. Apostolopoulos, V., et al., Induction of HLA-A2-restricted CTLs to the mucin 1 human breast cancer antigen. J. Immunol., 1997. 159(11): p. 5211–8.
51. Brossart, P., et al., Identification of HLA-A2-restricted T-cell epitopes derived from the MUC1 tumor antigen for broadly applicable vaccine therapies. Blood, 1999. 93(12): p. 4309–17.
52. Pietersz, G. A., et al., Definition of MHC-restricted CTL epitopes from non-variable number of tandem repeat sequence of MUC1. Vaccine, 2000. 18(19): p. 2059–71.
53. De Plaen, E., et al., Structure, chromosomal localization, and expression of 12 genes of the MAGE family. Immunogenetics, 1994. 40(5): p. 360–9.
54. Lucas, S., E. De Plaen, and T. Boon, MAGE-B5, MAGE-B6, MAGE-C2, and MAGE-C3: four new members of the MAGE family with tumor-specific expression. Int. J. Cancer, 2000. 87(1): p. 55–60.
55. Lucas, S., et al., Identification of a new MAGE gene with tumor-specific expression by representational difference analysis. Cancer Res., 1998. 58(4): p. 743–52.
56. Lurquin, C., et al., Two members of the human MAGEB gene family located in Xp21.3 are expressed in tumors of various histological origins. Genomics, 1997. 46(3): p. 397–408.
57. Muscatelli, F., et al., Isolation and characterization of a MAGE gene family in the Xp21.3 region. Proc. Natl. Acad. Sci. USA, 1995. 92(11): p. 4987–91.
58. Traversari, C., et al., A nonapeptide encoded by human gene MAGE-1 is recognized on HLA-A1 by cytolytic T lymphocytes directed against tumor antigen MZ2-E. J. Exp. Med., 1992. 176(5): p. 1453–7.
59. van der Bruggen, P., et al., A peptide encoded by human gene MAGE-3 and presented by HLA-A2 induces cytolytic T lymphocytes that recognize tumor cells expressing MAGE-3. Eur. J. Immunol., 1994. 24(12): p. 3038–43.
60. Visseren, M. J., et al., Identification of HLA-A*0201-restricted CTL epitopes encoded by the tumor-specific MAGE-2 gene product. Int. J. Cancer., 1997. 73(1): p. 125–30.
61. Gaugler, B., et al., Human gene MAGE-3 codes for an antigen recognized on a melanoma by autologous cytolytic T lymphocytes. J. Exp. Med., 1994. 179(3): p. 921–30.
62. Bukholm, I. K., et al., E-cadherin and alpha-, beta-, and gamma-catenin protein expression in relation to metastasis in human breast carcinoma. J. Pathol., 1998. 185(3): p. 262–6.
63. Berx, G., et al., E-cadherin is a tumor/invasion suppressor gene mutated in human lobular breast cancers. Embo, 1995. 14(24); p. 6107–15.
64. Berx, G., F. Nollet, and F. van Roy, Dysregulation of the E-cadherin/catenin complex by irreversible mutations in human carcinomas. Cell Adhes. Commun., 1998. 6(2–3): p. 171–84.
65. Milgraum, L. Z., et al., Enzymes of the fatty acid synthesis pathway are highly expressed in in situ breast carcinoma. Clin. Cancer Res., 1997. 3(11); p. 2115–20.
66. Alo, P. L., et al., Fatty acid synthase (FAS) predictive strength in poorly differentiated early breast carcinomas. Tumori, 1999. 85(1): p. 35–40.
67. Kuhajda, F. P., et al., Synthesis and antitumor activity of an inhibitor of fatty acid synthase. Proc. Natl. Acad. Sci. USA, 2000.
68. Pizer, E. S., et al., Pharmacological inhibitors of mammalian fatty acid synthase suppress DNA replication and induce apoptosis in tumor cell lines. Cancer Res., 1998. 58(20): p. 4611–5.
69. Pizer, E. S., et al., Inhibition of fatty acid synthesis induces programmed cell death in human breast cancer cells. Cancer Res., 1996. 56(12): p. 2745–7.
70. Li, L. C., et al.,, Frequent methylation of estrogen receptor in prostate cancer: correlation with tumor progression. Cancer Res., 2000. 60(3): p. 702–6.
71. Szyf, M., Targeting DNA methyltransferase in cancer. Cancer. Metastasis Rev., 1998. 17(2): p. 219–31.
72. Pilat, M. J., et al., Examination of the DNA methylation properties in nontumorigenic and tumorigenic breast epithelial cell lines. Anticancer Res., 1998. 18(4A): p. 2575–82.
73. Szyf, M., The DNA methylation machinery as a target for anticancer therapy. Pharmacol. Ther., 1996. 70(1): p. 1–37.
74. Parker, K. C., et al., The beta 2-microglobulin dissociation rate is an accurate measure of the stability of MHC class I heterotrimers and depends on which peptide is bound. J. Immunol., 1992. 149(6): p. 1896–904.
75. Huczko, E. L., et al., Characteristics of endogenous peptides eluted from the class I MHC molecule HLA-B7 determined by mass spectrometry and computer modeling. J Immunol, 1993. 151(5): p. 2572–87.

76. Hansen, T. H., and Lee, D. R. 1997. Mechanism of class I assembly with beta 2 microglobulin and loading with peptide. Adv Immunol. 64:105–37.
77. Lanzavecchia, A., G. Lezzi, and A. Viola. 1999. From TCR engagement to T cell activation: a kinetic view of T cell behaviour. Cell 96:1
78. A. van der Merwe. 1999. TCR binding to peptide-MHC stabilizes a flexible recognition interface. Immunity 10:357.
79. Garboczi, D. N., D. T. Hung, and D. C. Wiley. 1992. HLA-A2-peptide complexes: refolding and crystallization of molecules expressed in *Escherichia coli* and complexed with single antigenic peptides. Proc. Natl. Acad. Sci. USA 89:3429.
80. Mottez, E., P. Langlade-Demoyen, H. Gournier, F. Martinon, J. Maryanski, P. Kourilsky, and J. P. Abastado. 1995. Cells expressing a major histocompatibility complex class I molecule with a single covalently bound peptide are highly immunogenic. J. Exp. Med. 181:493.
81. Lone, Y.-C., Motta, I., Mottez, E., Guilloux, Y., Lim, A., Demay, F., Levraud, J., Kourilsky, P., and Abastado, J., 1998. In virto induction of specific cytotoxic T lymphocyes using recombinant single-chain class I/peptide complexes. *J. Immunother.* 21:283.
82. Mage M G, Lee L, Ribaudo R K, Corr M, Kozlowski S, McHugh L, and Margulies D H 1992. A recombinant soluble, single-chain class I major histocompatibility complex molecule with biological activity. *Proc Natl Acad Sci USA* 89:10658.
83. Lee L, McHugh L, Ribaudo R K, Kozlowski S, Margulies D H, and Mage M G. 1994. Functional cell surface expression by a recombinant single-chain class I major histocompatibility complex molecule with a cis-active beta 2-microglobulin domain. *Eur. J. Immunol.* 24:2633.
84. Matsumura, M., Y. Saito, M. R. Jackson, E. S. Song, and P. A. Peterson. 1992. In vitro peptide binding to soluble empty class I major histocompatibility complex molecules isolated from transfected Drosophila melanogaster cells. J. Biol, Chem. 267:23589.
85. Stern, L. J., and D. C. Wiley. 1992. The human class II MHC protein HLA-DR1 assembles as empty heterodimers in the absence of antigenic peptide. Cell 68:465.
86. Altman, J. D., P. A. Reay, and M. M. Davis. 1993. Formation of functional Peptide complexes of class II major histocompatibility complex proteins from subunits produced in *Escherichia coli*. Proc. Natl. Acad. Sci. USA 90:10330.
87. Kozono, H., J. White, J. Clements, P. Marrack, and J. Kappler. 1994. Production of soluble MHC class II proteins with covalently bound single peptides. Nature 369:151.
88. White, J., Crawford, F., Fremont, D., Marrack, P., and Kappler. J. 1999. Soluble class I MHC with b-2 microglobulin covalently linked peptides: specific binding to a T-cell hybridoma. *J. Immunol.* 162:2671
89. Ignatowicz, L., G. Winslow, J. Bill, J. Kappler, and P. Marrack. 1995. Cell Surface expression of class II MHC proteins bound by a single peptide. J. Immunol.154:3852.
90. Ignatowicz, L., J. Kappler, and P. Marrack. 1996. The repertoire of T cells shaped by a single MHC/peptide ligand. Cell 84.521.
91. Uger, R. A., and B. H. Barber. 1998. Creating CTL targets with epitope-linked 2-microglobulin constructs. J. Immunol. 160:1598.
92. Halloran, M. M., Woods, J. M., Strieter, R. M., Szekanecz, Z., Volin, M. V., Hosaka, S., Haines, G. K., 3rd, Kunkel, S. L., Burdick, M. D., Walz, A., and Koch, A. E. (1999). The role of an epithelial neutrophil-activating peptide-78-like protein in rat adjuvant-induced arthritis. Journal of Immunology 162, 7492–500.
93. Barnes, D. A., Tse, J., Kaufhold, M., Owen, M., Hesselgesser, J., Strieter, R., Horuk, R., and Perez, H. D. (1998). Polyclonal antibody directed against human RANTES ameliorates disease in the Lewis rat adjuvant-induced arthritis model, J Clin Invest 101, 2910–9.
94. Gong, J. H., Ratkay, L. G., Waterfield, J. D., and Clark-Lewis, I. (1997). An antagonist of monocyte chemoattractant protein 1 (MCP-1) inhibits arthritis in the MRL-1 pr mouse model. J Exp Med 186, 131–7.
95. Schimmer, R. C., Schrier, D. J., Flory, C. M., Laemont, K. D., Tung, D., Metz, A. L., Friedl, H. P., Conroy, M. C., Warren, J. S., Beck, B., and Ward, P. A. (1998). Streptococcal cell wall-induced arthritis; requirements for IL-4, IL-10, IFN-gamma, and monocyte chemoattractant protein-1. Journal of Immunology 160, 1466–71.
96. Diehl, M., Munz, C., Keilholz, W., Stevanovic, S., Holmes, N., Loke, Y. W., and Rammensee, H. G. (1996). Nonclassical HLA-G molecules are classical peptide presenters. Curr. Biol. 6:305.

What is claimed is:

1. A peptide of amino acid sequence set forth in SEQ ID NO: 13.

2. A composition comprising, as an active ingredient, the peptide of claim 1, and a pharmaceutically acceptable carrier.

3. The composition of claim 2, wherein said composition further comprises, as an active ingredient, an antigen presenting cells, said antigen presenting cell presenting the peptide of claim 1.

* * * * *

SEQUENCE LISTING

<160> NUMBER OF SEQ ID NOS: 204

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Leu Leu Asp Val Pro Thr Ala Ala Val
1               5

<210> SEQ ID NO 2
<211> LENGTH: 10
<212> TYPE: PRT
<213> ORGANISM: Artificial Sequence

```
<220> FEATURE:
<223> OTHER INFORMATION: synthetic peptide

<400> SEQUENCE: 2

Leu Leu Leu Asp Val Pro Thr Ala Ala Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Leu Leu Leu Asp Val Pro Thr Ala Ala Val Gln Ala
1               5                   10

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Gly Leu Leu Gly Thr Leu Val Gln
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Gly Leu Leu Gly Thr Leu Val Gln Leu
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Ala Leu Phe Gly Ala Leu Phe Leu Ala
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic peptide

<400> SEQUENCE: 7

Ser Leu Leu Gly Gly Asp Val Val Ser Val
1               5                   10

<210> SEQ ID NO 8
<211> LENGTH: 9
<212> TYPE: PRT
<213> ORGANISM: Artificial Sequence
<220> FEATURE:
```

<223> OTHER INFORMATION: synthetic peptide

<400> SEQUENCE: 8

Asn Leu Thr Ile Ser Asp Val Ser Val
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Ser Leu Trp Gly Gln Pro Ala Glu Ala
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Ser Leu Ile Gly His Leu Gln Thr Leu
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic peptide

<400> SEQUENCE: 11

Ser Leu Ser Glu Lys Thr Val Leu Leu
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Ser Leu Phe Pro Gly Lys Leu Glu Val
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic peptide

<400> SEQUENCE: 13

Gly Leu Ile Glu Lys Asn Ile Glu Leu
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 14

Gly Leu Tyr Pro Gly Leu Ile Trp Leu
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

Tyr Leu Leu Pro Ala Ile Val His Ile
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Ala Leu Ser Asp His His Ile Tyr Leu
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Ile Leu Asp Gln Lys Ile Asn Glu Val
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic peptide

<400> SEQUENCE: 18

Ile Leu Asp Lys Lys Val Glu Lys Val
1               5

<210> SEQ ID NO 19
<211> LENGTH: 11
<212> TYPE: PRT
<213> ORGANISM: Artificial Sequence
<220> FEATURE:
<223> OTHER INFORMATION: synthetic peptide

<400> SEQUENCE: 19

Ser Leu Leu Pro Pro Thr Ala Leu Val Gly Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic peptide
```

```
<400> SEQUENCE: 20

Gly Val Tyr Asp Gly Glu Glu His Ser Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthetic peptide

<400> SEQUENCE: 21

Ser Leu Leu Pro Pro Asp Ala Leu Val Gly Leu
1               5                   10

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Thr Leu Trp Val Asp Pro Tyr Glu Val
1               5

<210> SEQ ID NO 23
<211> LENGTH: 10
<212> TYPE: PRT
<213> ORGANISM: Artificial Sequence
<220> FEATURE:
<223> OTHER INFORMATION: synthetic peptide

<400> SEQUENCE: 23

Phe Leu Phe Asp Gly Ser Pro Thr Tyr Val
1               5                   10

<210> SEQ ID NO 24
<211> LENGTH: 11
<212> TYPE: PRT
<213> ORGANISM: Artificial Sequence
<220> FEATURE:
<223> OTHER INFORMATION: synthetic peptide

<400> SEQUENCE: 24

Phe Leu Phe Asp Gly Ser Pro Thr Tyr Val Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic peptide

<400> SEQUENCE: 25

Ala Leu Trp Asp Ile Glu Thr Gly Gln Gln Thr Val
1               5                   10

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26
```

Val Pro Ser Glu Pro Gly Gly Val Leu
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Ser Pro Thr Gln Pro Ile Gln Leu
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic peptide

<400> SEQUENCE: 28

Ser Pro Ala Leu Pro Gly Leu Lys Leu
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic peptide

<400> SEQUENCE: 29

Ala Pro Arg Thr Val Ala Leu Thr Ala
1               5

<210> SEQ ID NO 30
<211> LENGTH: 9
<212> TYPE: PRT
<213> ORGANISM: Artificial Sequence
<220> FEATURE:
<223> OTHER INFORMATION: synthetic peptide

<400> SEQUENCE: 30

Ser Pro Lys Leu Pro Val Ser Ser Leu
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic peptide

<400> SEQUENCE: 31

Lys Pro Ser Leu Pro Phe Thr Ser Leu
1               5

<210> SEQ ID NO 32
<211> LENGTH: 9
<212> TYPE: PRT
<213> ORGANISM: Artificial Sequence
<220> FEATURE:
<223> OTHER INFORMATION: synthetic peptide

<400> SEQUENCE: 32

```
Leu Val Met Ala Pro Arg Thr Val Leu
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic peptide

<400> SEQUENCE: 33

Lys Pro Ala Phe Phe Ala Glu Lys Leu
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic peptide

<400> SEQUENCE: 34

Ser Pro Tyr Gln Asn Ile Lys Ile Leu
1               5

<210> SEQ ID NO 35
<211> LENGTH: 11
<212> TYPE: PRT
<213> ORGANISM: Artificial Sequence
<220> FEATURE:
<223> OTHER INFORMATION: synthetic peptide

<400> SEQUENCE: 35

Ala Ala Ser Lys Glu Arg Ser Gly Val Ser Leu
1               5                   10

<210> SEQ ID NO 36
<211> LENGTH: 11
<212> TYPE: PRT
<213> ORGANISM: Artificial Sequence
<220> FEATURE:
<223> OTHER INFORMATION: synthetic peptide

<400> SEQUENCE: 36

Ala Pro Phe Glu Pro Leu Ala Ser Gly Ile Leu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: synthetic peptide

<400> SEQUENCE: 37

Ala Pro Ser Gly Ser Leu Ala Val Pro Leu Ala Val Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic peptide

<400> SEQUENCE: 38

Gly Val Tyr Asp Gly Arg Glu His Thr Val
```

```
1               5                   10
```

<210> SEQ ID NO 39
<211> LENGTH: 9
<212> TYPE: PRT
<213> ORGANISM: Artificial Sequence
<220> FEATURE:
<223> OTHER INFORMATION: synthetic peptide

<400> SEQUENCE: 39

Gly Leu Tyr Asp Gly Met Glu His Leu
1               5

<210> SEQ ID NO 40
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 40
agattcccaa gcttatgtct cgctccgtgg                                      30

<210> SEQ ID NO 41
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 41
agctagtcta gattatcaca tgtctcgatc ccacttaac                            39

<210> SEQ ID NO 42
<211> LENGTH: 9
<212> TYPE: PRT
<213> ORGANISM: Artificial Sequence
<220> FEATURE:
<223> OTHER INFORMATION: synthetic peptide

<400> SEQUENCE: 42

Ile Met Asp Gln Val Pro Phe Ser Val
1               5

<210> SEQ ID NO 43
<211> LENGTH: 9
<212> TYPE: PRT
<213> ORGANISM: Artificial Sequence
<220> FEATURE:
<223> OTHER INFORMATION: synthetic peptide

<400> SEQUENCE: 43

Ala Leu Leu Cys Ala Pro Ser Leu Leu
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic peptide

<400> SEQUENCE: 44

Ala Leu Ala Pro Gly Leu Pro Thr Ala
1               5

```
<210> SEQ ID NO 45
<211> LENGTH: 7
<212> TYPE: PRT
<213> ORGANISM: Artificial Sequence
<220> FEATURE:
<223> OTHER INFORMATION: synthetic peptide

<400> SEQUENCE: 45

Lys Leu Leu Glu Pro Val Leu
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic peptide

<400> SEQUENCE: 46

Ser Leu Leu Pro Ala Ile Val Glu
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic peptide

<400> SEQUENCE: 47

Ser Val Leu Gly Ser Leu Ser Ser Val
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide

<400> SEQUENCE: 48

Leu Leu Gly Pro Pro Val Gly Val
1               5

<210> SEQ ID NO 49
<211> LENGTH: 9
<212> TYPE: PRT
<213> ORGANISM: Artificial Sequence
<220> FEATURE:
<223> OTHER INFORMATION: synthetic peptide

<400> SEQUENCE: 49

Pro Gly Pro Pro Pro Pro Pro Pro
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic peptide

<400> SEQUENCE: 50

Ser Met Ser Gly Pro Leu Ile Gly Val
1               5

<210> SEQ ID NO 51
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 51

Ser Met Ala Pro Gly Leu Thr Ser Val
1               5

<210> SEQ ID NO 52
<211> LENGTH: 9
<212> TYPE: PRT
<213> ORGANISM: Artificial Sequence
<220> FEATURE:
<223> OTHER INFORMATION: synthetic peptide

<400> SEQUENCE: 52

Leu Leu Ile Pro Gly Leu Ala Thr Ala
1               5

<210> SEQ ID NO 53
<211> LENGTH: 9
<212> TYPE: PRT
<213> ORGANISM: Artificial Sequence
<220> FEATURE:
<223> OTHER INFORMATION: synthetic peptide

<400> SEQUENCE: 53

Gly Leu Leu Gly Asn Val Ala Glu Val
1               5

<210> SEQ ID NO 54
<211> LENGTH: 8
<212> TYPE: PRT
<213> ORGANISM: Artificial Sequence
<220> FEATURE:
<223> OTHER INFORMATION: synthetic peptide

<400> SEQUENCE: 54

Ser Leu Ile Lys Leu Val Glu Ala
1               5

<210> SEQ ID NO 55
<211> LENGTH: 9
<212> TYPE: PRT
<213> ORGANISM: Artificial Sequence
<220> FEATURE:
<223> OTHER INFORMATION: synthetic peptide

<400> SEQUENCE: 55

Gly Leu Ala Glu Ser Val Ser Thr Leu
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic peptide

<400> SEQUENCE: 56

Ala Ile Ile Gly Gly Thr Phe Thr Val
1               5

<210> SEQ ID NO 57
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 57

Ile Ile Thr Gly Pro Ala Pro Val Leu
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic peptide

<400> SEQUENCE: 58

Ser Phe Asp Gly Trp Ala Thr Val
1               5

<210> SEQ ID NO 59
<211> LENGTH: 9
<212> TYPE: PRT
<213> ORGANISM: Artificial Sequence
<220> FEATURE:
<223> OTHER INFORMATION: synthetic peptide

<400> SEQUENCE: 59

Leu Pro Pro Asp Ala Leu Val Gly Leu
1               5

<210> SEQ ID NO 60
<211> LENGTH: 9
<212> TYPE: PRT
<213> ORGANISM: Artificial Sequence
<220> FEATURE:
<223> OTHER INFORMATION: synthetic peptide

<400> SEQUENCE: 60

Ile Leu Asp Ala Gly Gly His Asn Val
1               5

<210> SEQ ID NO 61
<211> LENGTH: 9
<212> TYPE: PRT
<213> ORGANISM: Artificial Sequence
<220> FEATURE:
<223> OTHER INFORMATION: synthetic peptide

<400> SEQUENCE: 61

Gly Leu Tyr Ser Gly Val Thr Thr Val
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic peptide

<400> SEQUENCE: 62

Phe Leu Tyr Pro Phe Pro Leu
1               5

<210> SEQ ID NO 63
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 63

Ala Leu Leu Pro Ser Ser Pro Thr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic peptide

<400> SEQUENCE: 64

Lys Leu Gly Ser Val Pro Val Thr Val
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic peptide

<400> SEQUENCE: 65

Ala Leu Phe Pro Gly Val Ala Leu Leu
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic peptide

<400> SEQUENCE: 66

Gly Leu Val Gly Ser Leu Gln Glu Val
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic peptide

<400> SEQUENCE: 67

Ala Pro Leu Ser Asp Thr Ala Gln Val
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic peptide

<400> SEQUENCE: 68

Ala Pro Leu Ser Asp Thr Ala Gln Val
1               5

<210> SEQ ID NO 69
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 69

Gly Leu Ala Thr Asp Val Gln Thr Val
1               5

<210> SEQ ID NO 70
<211> LENGTH: 9
<212> TYPE: PRT
<213> ORGANISM: Artificial Sequence
<220> FEATURE:
<223> OTHER INFORMATION: synthetic peptide

<400> SEQUENCE: 70

Ser Leu Phe Gly Gly Ser Val Lys Leu
1               5

<210> SEQ ID NO 71
<211> LENGTH: 9
<212> TYPE: PRT
<213> ORGANISM: Artificial Sequence
<220> FEATURE:
<223> OTHER INFORMATION: synthetic peptide

<400> SEQUENCE: 71

Lys Val Gly Pro Val Pro Val Leu Val
1               5

<210> SEQ ID NO 72
<211> LENGTH: 9
<212> TYPE: PRT
<213> ORGANISM: Artificial Sequence
<220> FEATURE:
<223> OTHER INFORMATION: synthetic peptide

<400> SEQUENCE: 72

Gly Leu Leu Pro Asp Val Pro Ser Leu
1               5

<210> SEQ ID NO 73
<211> LENGTH: 9
<212> TYPE: PRT
<213> ORGANISM: Artificial Sequence
<220> FEATURE:
<223> OTHER INFORMATION: synthetic peptide

<400> SEQUENCE: 73

Ala Leu Pro Pro Val Leu Thr Thr Val
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic peptide

<400> SEQUENCE: 74

Gly Val Leu Pro Asn Ile Gln Ala Val
1               5

<210> SEQ ID NO 75
<211> LENGTH: 9
<212> TYPE: PRT
<213> ORGANISM: Artificial Sequence
<220> FEATURE:
```

<223> OTHER INFORMATION: synthetic peptide

<400> SEQUENCE: 75

Ala Leu Thr Pro Val Val Val Thr Leu
1               5

<210> SEQ ID NO 76
<211> LENGTH: 9
<212> TYPE: PRT
<213> ORGANISM: Artificial Sequence
<220> FEATURE:
<223> OTHER INFORMATION: synthetic peptide

<400> SEQUENCE: 76

Ala Leu Asn Pro Ala Asp Ile Thr Val
1               5

<210> SEQ ID NO 77
<211> LENGTH: 9
<212> TYPE: PRT
<213> ORGANISM: Artificial Sequence
<220> FEATURE:
<223> OTHER INFORMATION: synthetic peptide

<400> SEQUENCE: 77

Asp Ala Glu Gly Leu Ala Leu Leu Leu
1               5

<210> SEQ ID NO 78
<211> LENGTH: 9
<212> TYPE: PRT
<213> ORGANISM: Artificial Sequence
<220> FEATURE:
<223> OTHER INFORMATION: synthetic peptide

<400> SEQUENCE: 78

Ser Leu Thr Gly His Ile Ser Thr Val
1               5

<210> SEQ ID NO 79
<211> LENGTH: 8
<212> TYPE: PRT
<213> ORGANISM: Artificial Sequence
<220> FEATURE:
<223> OTHER INFORMATION: synthetic peptide

<400> SEQUENCE: 79

Val His Val Leu Thr Phe Thr Val
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic peptide

<400> SEQUENCE: 80

Ile Leu Gly Leu Gly Tyr Pro Ser Leu
1               5

<210> SEQ ID NO 81
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 81

Ala Leu Leu Ala Gly Ser Glu Tyr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: synthetic peptide

<400> SEQUENCE: 82

Ser Leu Ala Glu Leu Val His Ala Val
1               5

<210> SEQ ID NO 83
<211> LENGTH: 8
<212> TYPE: PRT
<213> ORGANISM: Artificial Sequence
<220> FEATURE:
<223> OTHER INFORMATION: synthetic peptide

<400> SEQUENCE: 83

Met Gln Pro Ile Leu Leu Leu Leu
1               5

<210> SEQ ID NO 84
<211> LENGTH: 8
<212> TYPE: PRT
<213> ORGANISM: Artificial Sequence
<220> FEATURE:
<223> OTHER INFORMATION: synthetic peptide

<400> SEQUENCE: 84

Gly Leu Phe Ala Pro Gln Phe Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic peptide

<400> SEQUENCE: 85

Ala Leu Trp Gly Gln Gly Thr Leu Val
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic peptide

<400> SEQUENCE: 86

Asp Thr Glu Thr Ala Val Val Asn Val
1               5

<210> SEQ ID NO 87
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 87

Ala Leu Leu Pro Ile Phe Phe Gly Ala
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic peptide

<400> SEQUENCE: 88

Ala Met Val Ile Phe Lys Ser Gly Val
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic peptide

<400> SEQUENCE: 89

Ser Leu Leu Pro Ala Ile Val Glu Leu
1               5

<210> SEQ ID NO 90
<211> LENGTH: 9
<212> TYPE: PRT
<213> ORGANISM: Artificial Sequence
<220> FEATURE:
<223> OTHER INFORMATION: synthetic peptide

<400> SEQUENCE: 90

Ser Leu Phe Pro Gly Gln Val Val Ile
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic peptide

<400> SEQUENCE: 91

Ser Leu Leu Glu Lys Ser Leu Gly Leu
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic peptide

<400> SEQUENCE: 92

Ile Leu Thr Asp Ile Thr Lys Gly Val
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic peptide

<400> SEQUENCE: 93
```

```
Gly Leu Phe Gln Gly Lys Thr Pro Leu
1               5
```

<210> SEQ ID NO 94
<211> LENGTH: 8
<212> TYPE: PRT
<213> ORGANISM: Artificial Sequence
<220> FEATURE:
<223> OTHER INFORMATION: synthetic peptide

<400> SEQUENCE: 94

```
Glu Ser Gln Leu Lys Lys Met Val
1               5
```

<210> SEQ ID NO 95
<211> LENGTH: 8
<212> TYPE: PRT
<213> ORGANISM: Artificial Sequence
<220> FEATURE:
<223> OTHER INFORMATION: synthetic peptide

<400> SEQUENCE: 95

```
Phe Leu Tyr Pro Phe Pro Leu Ala
1               5
```

<210> SEQ ID NO 96
<211> LENGTH: 9
<212> TYPE: PRT
<213> ORGANISM: Artificial Sequence
<220> FEATURE:
<223> OTHER INFORMATION: synthetic peptide

<400> SEQUENCE: 96

```
Ala Leu Thr Gly His Leu Glu Glu Val
1               5
```

<210> SEQ ID NO 97
<211> LENGTH: 9
<212> TYPE: PRT
<213> ORGANISM: Artificial Sequence
<220> FEATURE:
<223> OTHER INFORMATION: synthetic peptide

<400> SEQUENCE: 97

```
Ser Leu Leu Asp Pro Val Pro Glu Val
1               5
```

<210> SEQ ID NO 98
<211> LENGTH: 9
<212> TYPE: PRT
<213> ORGANISM: Artificial Sequence
<220> FEATURE:
<223> OTHER INFORMATION: synthetic peptide

<400> SEQUENCE: 98

```
Met Ala Pro Gln Ala Leu Leu Leu Leu
1               5
```

<210> SEQ ID NO 99
<211> LENGTH: 9
<212> TYPE: PRT
<213> ORGANISM: Artificial Sequence
<220> FEATURE:
<223> OTHER INFORMATION: synthetic peptide

<400> SEQUENCE: 99

Phe Ser Asn Gly Tyr Leu Ala Ser Leu
1               5

<210> SEQ ID NO 100
<211> LENGTH: 9
<212> TYPE: PRT
<213> ORGANISM: Artificial Sequence
<220> FEATURE:
<223> OTHER INFORMATION: synthetic peptide

<400> SEQUENCE: 100

Thr Leu Ile Glu Asp Ile Leu Gly Val
1               5

<210> SEQ ID NO 101
<211> LENGTH: 9
<212> TYPE: PRT
<213> ORGANISM: Artificial Sequence
<220> FEATURE:
<223> OTHER INFORMATION: synthetic peptide

<400> SEQUENCE: 101

Ile Ala Glu Ala Val Arg Thr Thr Leu
1               5

<210> SEQ ID NO 102
<211> LENGTH: 9
<212> TYPE: PRT
<213> ORGANISM: Artificial Sequence
<220> FEATURE:
<223> OTHER INFORMATION: synthetic peptide

<400> SEQUENCE: 102

Lys Leu Ser Glu Leu Glu Ala Ala Leu
1               5

<210> SEQ ID NO 103
<211> LENGTH: 10
<212> TYPE: PRT
<213> ORGANISM: Artificial Sequence
<220> FEATURE:
<223> OTHER INFORMATION: synthetic peptide

<400> SEQUENCE: 103

Phe Leu Ser Glu His Pro Asn Val Thr Leu
1               5                   10

<210> SEQ ID NO 104
<211> LENGTH: 9
<212> TYPE: PRT
<213> ORGANISM: Artificial Sequence
<220> FEATURE:
<223> OTHER INFORMATION: synthetic peptide

<400> SEQUENCE: 104

Ser Leu Ser Val Lys Leu Glu Gln Ala
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic peptide

<400> SEQUENCE: 105

Met Leu Leu Ala Ala Leu Met Ile Val

```
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic peptide

<400> SEQUENCE: 106

Ala Ile Leu Pro Thr Ser Ile Phe Leu
1               5

<210> SEQ ID NO 107
<211> LENGTH: 9
<212> TYPE: PRT
<213> ORGANISM: Artificial Sequence
<220> FEATURE:
<223> OTHER INFORMATION: synthetic peptide

<400> SEQUENCE: 107

Ala Ala Leu Pro Asn Val Tyr Glu Val
1               5

<210> SEQ ID NO 108
<211> LENGTH: 9
<212> TYPE: PRT
<213> ORGANISM: Artificial Sequence
<220> FEATURE:
<223> OTHER INFORMATION: synthetic peptide

<400> SEQUENCE: 108

Arg Met Leu Pro His Ala Pro Gly Val
1               5

<210> SEQ ID NO 109
<211> LENGTH: 9
<212> TYPE: PRT
<213> ORGANISM: Artificial Sequence
<220> FEATURE:
<223> OTHER INFORMATION: synthetic peptide

<400> SEQUENCE: 109

Leu Met Val Leu Val Ala Leu Ile Leu
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic peptide

<400> SEQUENCE: 110

Lys Ile Leu Pro Thr Leu Glu Ala Val
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic peptide

<400> SEQUENCE: 111

Ala Leu Leu Asp Arg Ile Val Ser Val
1               5
```

```
<210> SEQ ID NO 112
<211> LENGTH: 9
<212> TYPE: PRT
<213> ORGANISM: Artificial Sequence
<220> FEATURE:
<223> OTHER INFORMATION: synthetic peptide

<400> SEQUENCE: 112

Thr Leu Val Tyr His Val Val Gly Val
1               5

<210> SEQ ID NO 113
<211> LENGTH: 9
<212> TYPE: PRT
<213> ORGANISM: Artificial Sequence
<220> FEATURE:
<223> OTHER INFORMATION: synthetic peptide

<400> SEQUENCE: 113

Tyr Leu Pro Pro Ala Thr Gln Val Val
1               5

<210> SEQ ID NO 114
<211> LENGTH: 9
<212> TYPE: PRT
<213> ORGANISM: Artificial Sequence
<220> FEATURE:
<223> OTHER INFORMATION: synthetic peptide

<400> SEQUENCE: 114

Pro Met Glu Ala Leu Ala Glu Gln Val
1               5

<210> SEQ ID NO 115
<211> LENGTH: 9
<212> TYPE: PRT
<213> ORGANISM: Artificial Sequence
<220> FEATURE:
<223> OTHER INFORMATION: synthetic peptide

<400> SEQUENCE: 115

Arg Leu Ser Glu Ala Ile Val Thr Val
1               5

<210> SEQ ID NO 116
<211> LENGTH: 9
<212> TYPE: PRT
<213> ORGANISM: Artificial Sequence
<220> FEATURE:
<223> OTHER INFORMATION: synthetic peptide

<400> SEQUENCE: 116

Ser Leu Asp Gln Pro Thr Gln Thr Val
1               5

<210> SEQ ID NO 117
<211> LENGTH: 9
<212> TYPE: PRT
<213> ORGANISM: Artificial Sequence
<220> FEATURE:
<223> OTHER INFORMATION: synthetic peptide

<400> SEQUENCE: 117

Lys Leu His Gly Val Asn Ile Asn Val
1               5
```

```
<210> SEQ ID NO 118
<211> LENGTH: 9
<212> TYPE: PRT
<213> ORGANISM: Artificial Sequence
<220> FEATURE:
<223> OTHER INFORMATION: synthetic peptide

<400> SEQUENCE: 118

Leu Val Met Ala Pro Arg Thr Val Leu
1               5

<210> SEQ ID NO 119
<211> LENGTH: 9
<212> TYPE: PRT
<213> ORGANISM: Artificial Sequence
<220> FEATURE:
<223> OTHER INFORMATION: synthetic peptide

<400> SEQUENCE: 119

Ser Ile Ile Gly Arg Leu Leu Glu Val
1               5

<210> SEQ ID NO 120
<211> LENGTH: 9
<212> TYPE: PRT
<213> ORGANISM: Artificial Sequence
<220> FEATURE:
<223> OTHER INFORMATION: synthetic peptide

<400> SEQUENCE: 120

Met Ala Val Ala Leu Gln Leu Arg Val
1               5

<210> SEQ ID NO 121
<211> LENGTH: 9
<212> TYPE: PRT
<213> ORGANISM: Artificial Sequence
<220> FEATURE:
<223> OTHER INFORMATION: synthetic peptide

<400> SEQUENCE: 121

Gly Leu Asn Glu Glu Ile Ala Arg Val
1               5

<210> SEQ ID NO 122
<211> LENGTH: 9
<212> TYPE: PRT
<213> ORGANISM: Artificial Sequence
<220> FEATURE:
<223> OTHER INFORMATION: synthetic peptide

<400> SEQUENCE: 122

Ile Met Lys Val Ala Gln Ala Lys Leu
1               5

<210> SEQ ID NO 123
<211> LENGTH: 9
<212> TYPE: PRT
<213> ORGANISM: Artificial Sequence
<220> FEATURE:
<223> OTHER INFORMATION: synthetic peptide

<400> SEQUENCE: 123

Thr Leu Ser Glu Val Thr Asn Gln Leu
1               5
```

```
<210> SEQ ID NO 124
<211> LENGTH: 9
<212> TYPE: PRT
<213> ORGANISM: Artificial Sequence
<220> FEATURE:
<223> OTHER INFORMATION: synthetic peptide

<400> SEQUENCE: 124

Ala Leu Phe Glu Gly Lys Val Gln Leu
1               5

<210> SEQ ID NO 125
<211> LENGTH: 9
<212> TYPE: PRT
<213> ORGANISM: Artificial Sequence
<220> FEATURE:
<223> OTHER INFORMATION: synthetic peptide

<400> SEQUENCE: 125

Gly Leu Lys Gly Arg Val Phe Glu Val
1               5

<210> SEQ ID NO 126
<211> LENGTH: 9
<212> TYPE: PRT
<213> ORGANISM: Artificial Sequence
<220> FEATURE:
<223> OTHER INFORMATION: synthetic peptide

<400> SEQUENCE: 126

Asn Ile Phe Pro Tyr Pro Val Gly Val
1               5

<210> SEQ ID NO 127
<211> LENGTH: 10
<212> TYPE: PRT
<213> ORGANISM: Artificial Sequence
<220> FEATURE:
<223> OTHER INFORMATION: synthetic peptide

<400> SEQUENCE: 127

Leu Val Ser Ile Val Val Ala Val Pro Leu
1               5                   10

<210> SEQ ID NO 128
<211> LENGTH: 9
<212> TYPE: PRT
<213> ORGANISM: Artificial Sequence
<220> FEATURE:
<223> OTHER INFORMATION: synthetic peptide

<400> SEQUENCE: 128

Asn Met Tyr Gly Lys Val Val Thr Val
1               5

<210> SEQ ID NO 129
<211> LENGTH: 10
<212> TYPE: PRT
<213> ORGANISM: Artificial Sequence
<220> FEATURE:
<223> OTHER INFORMATION: synthetic peptide

<400> SEQUENCE: 129

Ser Leu Ile Asn Val Gly Leu Ile Ser Val
1               5                   10

<210> SEQ ID NO 130
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 130

Ala Leu Leu Gly Thr Leu Trp Glu Ile
1               5

<210> SEQ ID NO 131
<211> LENGTH: 9
<212> TYPE: PRT
<213> ORGANISM: Artificial Sequence
<220> FEATURE:
<223> OTHER INFORMATION: synthetic peptide

<400> SEQUENCE: 131

Phe Gln Asp Pro Val Pro Leu Thr Val
1               5

<210> SEQ ID NO 132
<211> LENGTH: 9
<212> TYPE: PRT
<213> ORGANISM: Artificial Sequence
<220> FEATURE:
<223> OTHER INFORMATION: synthetic peptide

<400> SEQUENCE: 132

Gly Leu Tyr Pro Asn Leu Ile Gln Val
1               5

<210> SEQ ID NO 133
<211> LENGTH: 9
<212> TYPE: PRT
<213> ORGANISM: Artificial Sequence
<220> FEATURE:
<223> OTHER INFORMATION: synthetic peptide

<400> SEQUENCE: 133

Val Met Asp Ser Lys Ile Val Gln Val
1               5

<210> SEQ ID NO 134
<211> LENGTH: 9
<212> TYPE: PRT
<213> ORGANISM: Artificial Sequence
<220> FEATURE:
<223> OTHER INFORMATION: synthetic peptide

<400> SEQUENCE: 134

Ala Leu Leu Asp Lys Leu Tyr Ala Leu
1               5

<210> SEQ ID NO 135
<211> LENGTH: 9
<212> TYPE: PRT
<213> ORGANISM: Artificial Sequence
<220> FEATURE:
<223> OTHER INFORMATION: synthetic peptide

<400> SEQUENCE: 135

Asn Leu Ala Ser Phe Ile Glu Gln Val
1               5

<210> SEQ ID NO 136
<211> LENGTH: 8
```

```
<212> TYPE: PRT
<213> ORGANISM: Artificial Sequence
<220> FEATURE:
<223> OTHER INFORMATION: synthetic peptide

<400> SEQUENCE: 136

Thr Leu Trp Val Asp Pro Tyr Glu
1               5

<210> SEQ ID NO 137
<211> LENGTH: 9
<212> TYPE: PRT
<213> ORGANISM: Artificial Sequence
<220> FEATURE:
<223> OTHER INFORMATION: synthetic peptide

<400> SEQUENCE: 137

Lys Ile Ala Asp Phe Gly Trp Ser Val
1               5

<210> SEQ ID NO 138
<211> LENGTH: 9
<212> TYPE: PRT
<213> ORGANISM: Artificial Sequence
<220> FEATURE:
<223> OTHER INFORMATION: synthetic peptide

<400> SEQUENCE: 138

Ser Leu Leu Ser His Val Glu Gln Leu
1               5

<210> SEQ ID NO 139
<211> LENGTH: 9
<212> TYPE: PRT
<213> ORGANISM: Artificial Sequence
<220> FEATURE:
<223> OTHER INFORMATION: synthetic peptide

<400> SEQUENCE: 139

Gly Leu Ala Asp Lys Val Tyr Phe Leu
1               5

<210> SEQ ID NO 140
<211> LENGTH: 9
<212> TYPE: PRT
<213> ORGANISM: Artificial Sequence
<220> FEATURE:
<223> OTHER INFORMATION: synthetic peptide

<400> SEQUENCE: 140

Ser Leu Leu Asp Ile Ile Glu Lys Val
1               5

<210> SEQ ID NO 141
<211> LENGTH: 9
<212> TYPE: PRT
<213> ORGANISM: Artificial Sequence
<220> FEATURE:
<223> OTHER INFORMATION: synthetic peptide

<400> SEQUENCE: 141

Phe Val Phe Pro Gly Glu Leu Leu Leu
1               5

<210> SEQ ID NO 142
<211> LENGTH: 9
<212> TYPE: PRT
```

-continued

```
<213> ORGANISM: Artificial Sequence
<220> FEATURE:
<223> OTHER INFORMATION: synthetic peptide

<400> SEQUENCE: 142

Ala Leu Asn Glu Leu Leu Gln His Val
1               5

<210> SEQ ID NO 143
<211> LENGTH: 9
<212> TYPE: PRT
<213> ORGANISM: Artificial Sequence
<220> FEATURE:
<223> OTHER INFORMATION: synthetic peptide

<400> SEQUENCE: 143

Asn Leu Tyr Glu Gly Gln Ile Thr Val
1               5

<210> SEQ ID NO 144
<211> LENGTH: 9
<212> TYPE: PRT
<213> ORGANISM: Artificial Sequence
<220> FEATURE:
<223> OTHER INFORMATION: synthetic peptide

<400> SEQUENCE: 144

Phe Thr Lys Asp Phe Ala Pro Val Ile
1               5

<210> SEQ ID NO 145
<211> LENGTH: 9
<212> TYPE: PRT
<213> ORGANISM: Artificial Sequence
<220> FEATURE:
<223> OTHER INFORMATION: synthetic peptide

<400> SEQUENCE: 145

Lys Leu Leu Glu Pro Val Leu Leu Leu
1               5

<210> SEQ ID NO 146
<211> LENGTH: 9
<212> TYPE: PRT
<213> ORGANISM: Artificial Sequence
<220> FEATURE:
<223> OTHER INFORMATION: synthetic peptide

<400> SEQUENCE: 146

Gly Leu Phe Ala Pro Gln Phe Tyr Val
1               5

<210> SEQ ID NO 147
<211> LENGTH: 9
<212> TYPE: PRT
<213> ORGANISM: Artificial Sequence
<220> FEATURE:
<223> OTHER INFORMATION: synthetic peptide

<400> SEQUENCE: 147

Leu Met Val Asp His Val Thr Glu Val
1               5

<210> SEQ ID NO 148
<211> LENGTH: 9
<212> TYPE: PRT
<213> ORGANISM: Artificial Sequence
```

<220> FEATURE:
<223> OTHER INFORMATION: synthetic peptide

<400> SEQUENCE: 148

Phe Leu Leu Pro Ile Leu Ser Gln Ile
1               5

<210> SEQ ID NO 149
<211> LENGTH: 9
<212> TYPE: PRT
<213> ORGANISM: Artificial Sequence
<220> FEATURE:
<223> OTHER INFORMATION: synthetic peptide

<400> SEQUENCE: 149

Phe Leu Ile Pro Leu Asn Ile Thr Asn
1               5

<210> SEQ ID NO 150
<211> LENGTH: 9
<212> TYPE: PRT
<213> ORGANISM: Artificial Sequence
<220> FEATURE:
<223> OTHER INFORMATION: synthetic peptide

<400> SEQUENCE: 150

Asn Leu Leu Pro Lys Leu His Ile Val
1               5

<210> SEQ ID NO 151
<211> LENGTH: 9
<212> TYPE: PRT
<213> ORGANISM: Artificial Sequence
<220> FEATURE:
<223> OTHER INFORMATION: synthetic peptide

<400> SEQUENCE: 151

Leu Leu Asp Arg Phe Leu Ala Thr Val
1               5

<210> SEQ ID NO 152
<211> LENGTH: 10
<212> TYPE: PRT
<213> ORGANISM: Artificial Sequence
<220> FEATURE:
<223> OTHER INFORMATION: synthetic peptide

<400> SEQUENCE: 152

Tyr Leu Asp Pro Ser Val Leu Ser Gly Val
1               5                   10

<210> SEQ ID NO 153
<211> LENGTH: 9
<212> TYPE: PRT
<213> ORGANISM: Artificial Sequence
<220> FEATURE:
<223> OTHER INFORMATION: synthetic peptide

<400> SEQUENCE: 153

Leu Leu Tyr Pro Thr Glu Ile Thr Val
1               5

<210> SEQ ID NO 154
<211> LENGTH: 9
<212> TYPE: PRT
<213> ORGANISM: Artificial Sequence
<220> FEATURE:

<223> OTHER INFORMATION: synthetic peptide

<400> SEQUENCE: 154

Asn Leu Gly Asp Phe Leu Ile Phe Leu
1               5

<210> SEQ ID NO 155
<211> LENGTH: 9
<212> TYPE: PRT
<213> ORGANISM: Artificial Sequence
<220> FEATURE:
<223> OTHER INFORMATION: synthetic peptide

<400> SEQUENCE: 155

Gly Leu Tyr Glu Gly Leu Thr Trp Leu
1               5

<210> SEQ ID NO 156
<211> LENGTH: 9
<212> TYPE: PRT
<213> ORGANISM: Artificial Sequence
<220> FEATURE:
<223> OTHER INFORMATION: synthetic peptide

<400> SEQUENCE: 156

Ser Leu Phe Asp Leu Asn Phe Gln Ala
1               5

<210> SEQ ID NO 157
<211> LENGTH: 9
<212> TYPE: PRT
<213> ORGANISM: Artificial Sequence
<220> FEATURE:
<223> OTHER INFORMATION: synthetic peptide

<400> SEQUENCE: 157

Met Phe Ser Leu Glu Asp Ser Ile Ile
1               5

<210> SEQ ID NO 158
<211> LENGTH: 9
<212> TYPE: PRT
<213> ORGANISM: Artificial Sequence
<220> FEATURE:
<223> OTHER INFORMATION: synthetic peptide

<400> SEQUENCE: 158

Ala Met Trp Glu His Pro Ile Thr Ala
1               5

<210> SEQ ID NO 159
<211> LENGTH: 9
<212> TYPE: PRT
<213> ORGANISM: Artificial Sequence
<220> FEATURE:
<223> OTHER INFORMATION: synthetic peptide

<400> SEQUENCE: 159

Tyr Leu Gly Arg Leu Ala His Glu Val
1               5

<210> SEQ ID NO 160
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 160

Gly Leu Ile Asp His Gln Thr Tyr Leu
1               5

<210> SEQ ID NO 161
<211> LENGTH: 9
<212> TYPE: PRT
<213> ORGANISM: Artificial Sequence
<220> FEATURE:
<223> OTHER INFORMATION: synthetic peptide

<400> SEQUENCE: 161

Ala Ile Gln Asp Lys Leu Phe Gln Val
1               5

<210> SEQ ID NO 162
<211> LENGTH: 8
<212> TYPE: PRT
<213> ORGANISM: Artificial Sequence
<220> FEATURE:
<223> OTHER INFORMATION: synthetic peptide

<400> SEQUENCE: 162

Ile Val Lys Trp Asp Arg Asp Met
1               5

<210> SEQ ID NO 163
<211> LENGTH: 9
<212> TYPE: PRT
<213> ORGANISM: Artificial Sequence
<220> FEATURE:
<223> OTHER INFORMATION: synthetic peptide

<400> SEQUENCE: 163

Arg Ile Ile Asp Val Val Tyr Asn Ala
1               5

<210> SEQ ID NO 164
<211> LENGTH: 9
<212> TYPE: PRT
<213> ORGANISM: Artificial Sequence
<220> FEATURE:
<223> OTHER INFORMATION: synthetic peptide

<400> SEQUENCE: 164

Lys Ile Tyr Glu Gly Gln Val Glu Val
1               5

<210> SEQ ID NO 165
<211> LENGTH: 9
<212> TYPE: PRT
<213> ORGANISM: Artificial Sequence
<220> FEATURE:
<223> OTHER INFORMATION: synthetic peptide

<400> SEQUENCE: 165

Phe Leu Pro Ser Tyr Ile Ile Asp Val
1               5

<210> SEQ ID NO 166
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 166

Tyr Met Met Pro Val Asn Ser Glu Val
1               5

<210> SEQ ID NO 167
<211> LENGTH: 9
<212> TYPE: PRT
<213> ORGANISM: Artificial Sequence
<220> FEATURE:
<223> OTHER INFORMATION: synthetic peptide

<400> SEQUENCE: 167

Asn Lys Asp Leu Lys Met Pro Lys Val
1               5

<210> SEQ ID NO 168
<211> LENGTH: 9
<212> TYPE: PRT
<213> ORGANISM: Artificial Sequence
<220> FEATURE:
<223> OTHER INFORMATION: synthetic peptide

<400> SEQUENCE: 168

Asn Leu Ala Glu Asp Ile Met Arg Leu
1               5

<210> SEQ ID NO 169
<211> LENGTH: 9
<212> TYPE: PRT
<213> ORGANISM: Artificial Sequence
<220> FEATURE:
<223> OTHER INFORMATION: synthetic peptide

<400> SEQUENCE: 169

Tyr Leu Pro Glu Leu Leu Gln Thr Val
1               5

<210> SEQ ID NO 170
<211> LENGTH: 9
<212> TYPE: PRT
<213> ORGANISM: Artificial Sequence
<220> FEATURE:
<223> OTHER INFORMATION: synthetic peptide

<400> SEQUENCE: 170

Phe Leu Tyr Pro Phe Pro Leu Ala Leu
1               5

<210> SEQ ID NO 171
<211> LENGTH: 9
<212> TYPE: PRT
<213> ORGANISM: Artificial Sequence
<220> FEATURE:
<223> OTHER INFORMATION: synthetic peptide

<400> SEQUENCE: 171

Asn Leu Tyr Pro Phe Val Lys Thr Val
1               5

<210> SEQ ID NO 172
<211> LENGTH: 9
<212> TYPE: PRT
<213> ORGANISM: Artificial Sequence
<220> FEATURE:
<223> OTHER INFORMATION: synthetic peptide

<400> SEQUENCE: 172
```

```
Ser Val Ile Glu Gln Leu Phe Phe Val
1               5
```

<210> SEQ ID NO 173
<211> LENGTH: 9
<212> TYPE: PRT
<213> ORGANISM: Artificial Sequence
<220> FEATURE:
<223> OTHER INFORMATION: synthetic peptide

<400> SEQUENCE: 173

```
Ser Leu Leu Glu Pro Phe Val Tyr Leu
1               5
```

<210> SEQ ID NO 174
<211> LENGTH: 9
<212> TYPE: PRT
<213> ORGANISM: Artificial Sequence
<220> FEATURE:
<223> OTHER INFORMATION: synthetic peptide

<400> SEQUENCE: 174

```
Ile Leu Phe Gly His Glu Asn Arg Val
1               5
```

<210> SEQ ID NO 175
<211> LENGTH: 10
<212> TYPE: PRT
<213> ORGANISM: Artificial Sequence
<220> FEATURE:
<223> OTHER INFORMATION: synthetic peptide

<400> SEQUENCE: 175

```
Lys Leu Gln Glu Val Gly Gln Val Ser Val
1               5                   10
```

<210> SEQ ID NO 176
<211> LENGTH: 9
<212> TYPE: PRT
<213> ORGANISM: Artificial Sequence
<220> FEATURE:
<223> OTHER INFORMATION: synthetic peptide

<400> SEQUENCE: 176

```
Arg Leu Phe Asp Glu Pro Gln Leu Ala
1               5
```

<210> SEQ ID NO 177
<211> LENGTH: 10
<212> TYPE: PRT
<213> ORGANISM: Artificial Sequence
<220> FEATURE:
<223> OTHER INFORMATION: synthetic peptide

<400> SEQUENCE: 177

```
Ser Leu Phe Pro Gly Lys Leu Glu Val Val
1               5                   10
```

<210> SEQ ID NO 178
<211> LENGTH: 10
<212> TYPE: PRT
<213> ORGANISM: Artificial Sequence
<220> FEATURE:
<223> OTHER INFORMATION: synthetic peptide

<400> SEQUENCE: 178

-continued

Val Met Leu Gly Thr Pro Phe Leu Val Ile
1               5                   10

<210> SEQ ID NO 179
<211> LENGTH: 9
<212> TYPE: PRT
<213> ORGANISM: Artificial Sequence
<220> FEATURE:
<223> OTHER INFORMATION: synthetic peptide

<400> SEQUENCE: 179

Ser Leu Tyr Asp Tyr Asn Pro Asn Leu
1               5

<210> SEQ ID NO 180
<211> LENGTH: 10
<212> TYPE: PRT
<213> ORGANISM: Artificial Sequence
<220> FEATURE:
<223> OTHER INFORMATION: synthetic peptide

<400> SEQUENCE: 180

Phe Leu Leu Gly Pro Arg Leu Val Leu Ala
1               5                   10

<210> SEQ ID NO 181
<211> LENGTH: 10
<212> TYPE: PRT
<213> ORGANISM: Artificial Sequence
<220> FEATURE:
<223> OTHER INFORMATION: synthetic peptide

<400> SEQUENCE: 181

Phe Leu Tyr Thr Gly Glu Gly Asp Thr Val
1               5                   10

<210> SEQ ID NO 182
<211> LENGTH: 9
<212> TYPE: PRT
<213> ORGANISM: Artificial Sequence
<220> FEATURE:
<223> OTHER INFORMATION: synthetic peptide

<400> SEQUENCE: 182

Lys Leu Asn Pro Gln Gln Phe Glu Val
1               5

<210> SEQ ID NO 183
<211> LENGTH: 10
<212> TYPE: PRT
<213> ORGANISM: Artificial Sequence
<220> FEATURE:
<223> OTHER INFORMATION: synthetic peptide

<400> SEQUENCE: 183

Ser Leu Ala Asp Leu Gln Asn Asp Glu Val
1               5                   10

<210> SEQ ID NO 184
<211> LENGTH: 9
<212> TYPE: PRT
<213> ORGANISM: Artificial Sequence
<220> FEATURE:
<223> OTHER INFORMATION: synthetic peptide

<400> SEQUENCE: 184

Arg Leu Leu Asp Tyr Val Val Asn Ile

<210> SEQ ID NO 185
<211> LENGTH: 9
<212> TYPE: PRT
<213> ORGANISM: Artificial Sequence
<220> FEATURE:
<223> OTHER INFORMATION: synthetic peptide

<400> SEQUENCE: 185

Phe Val Asp Asp Tyr Thr Val Arg Val
1               5

<210> SEQ ID NO 186
<211> LENGTH: 9
<212> TYPE: PRT
<213> ORGANISM: Artificial Sequence
<220> FEATURE:
<223> OTHER INFORMATION: synthetic peptide

<400> SEQUENCE: 186

Ser Leu Phe Glu Gly Thr Trp Tyr Leu
1               5

<210> SEQ ID NO 187
<211> LENGTH: 9
<212> TYPE: PRT
<213> ORGANISM: Artificial Sequence
<220> FEATURE:
<223> OTHER INFORMATION: synthetic peptide

<400> SEQUENCE: 187

Ala Leu Tyr Asn Trp Leu Ile Gln Val
1               5

<210> SEQ ID NO 188
<211> LENGTH: 9
<212> TYPE: PRT
<213> ORGANISM: Artificial Sequence
<220> FEATURE:
<223> OTHER INFORMATION: synthetic peptide

<400> SEQUENCE: 188

Val Leu Ile Asp Tyr Gln Arg Asn Val
1               5

<210> SEQ ID NO 189
<211> LENGTH: 9
<212> TYPE: PRT
<213> ORGANISM: Artificial Sequence
<220> FEATURE:
<223> OTHER INFORMATION: synthetic peptide

<400> SEQUENCE: 189

Phe Thr Trp Glu Gly Leu Tyr Asn Val
1               5

<210> SEQ ID NO 190
<211> LENGTH: 9
<212> TYPE: PRT
<213> ORGANISM: Artificial Sequence
<220> FEATURE:
<223> OTHER INFORMATION: synthetic peptide

<400> SEQUENCE: 190

Ile Leu Met Glu His Ile His Lys Leu
1               5

```
<210> SEQ ID NO 191
<211> LENGTH: 10
<212> TYPE: PRT
<213> ORGANISM: Artificial Sequence
<220> FEATURE:
<223> OTHER INFORMATION: synthetic peptide

<400> SEQUENCE: 191

Arg Leu Asp Glu Leu Gly Gly Val Tyr Leu
1               5                   10

<210> SEQ ID NO 192
<211> LENGTH: 9
<212> TYPE: PRT
<213> ORGANISM: Artificial Sequence
<220> FEATURE:
<223> OTHER INFORMATION: synthetic peptide

<400> SEQUENCE: 192

Lys Leu Leu Ser Lys Phe Tyr Glu Leu
1               5

<210> SEQ ID NO 193
<211> LENGTH: 9
<212> TYPE: PRT
<213> ORGANISM: Artificial Sequence
<220> FEATURE:
<223> OTHER INFORMATION: synthetic peptide

<400> SEQUENCE: 193

Lys Val Leu Asp Phe Glu His Phe Leu
1               5

<210> SEQ ID NO 194
<211> LENGTH: 9
<212> TYPE: PRT
<213> ORGANISM: Artificial Sequence
<220> FEATURE:
<223> OTHER INFORMATION: synthetic peptide

<400> SEQUENCE: 194

Tyr Leu Pro Glu Asp Phe Ile Arg Val
1               5

<210> SEQ ID NO 195
<211> LENGTH: 8
<212> TYPE: PRT
<213> ORGANISM: Artificial Sequence
<220> FEATURE:
<223> OTHER INFORMATION: synthetic peptide

<400> SEQUENCE: 195

Ser Leu Lys Tyr Val Pro Leu Val
1               5

<210> SEQ ID NO 196
<211> LENGTH: 8
<212> TYPE: PRT
<213> ORGANISM: Artificial Sequence
<220> FEATURE:
<223> OTHER INFORMATION: synthetic peptide

<400> SEQUENCE: 196

Leu Pro Tyr Trp Gly Val Ala Leu
1               5
```

```
<210> SEQ ID NO 197
<211> LENGTH: 9
<212> TYPE: PRT
<213> ORGANISM: Artificial Sequence
<220> FEATURE:
<223> OTHER INFORMATION: synthetic peptide

<400> SEQUENCE: 197

Ser Ile Tyr Pro Ser Pro Thr Gly Val
1               5

<210> SEQ ID NO 198
<211> LENGTH: 9
<212> TYPE: PRT
<213> ORGANISM: Artificial Sequence
<220> FEATURE:
<223> OTHER INFORMATION: synthetic peptide

<400> SEQUENCE: 198

Ala Leu Ala Ser His Leu Ile Glu Ala
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic peptide

<400> SEQUENCE: 199

Lys Leu Gly Pro Ala Pro Lys Thr Leu
1               5

<210> SEQ ID NO 200
<211> LENGTH: 8
<212> TYPE: PRT
<213> ORGANISM: Artificial Sequence
<220> FEATURE:
<223> OTHER INFORMATION: synthetic peptide

<400> SEQUENCE: 200

Lys Leu Leu Glu Pro Val Leu Leu
1               5

<210> SEQ ID NO 201
<211> LENGTH: 9
<212> TYPE: PRT
<213> ORGANISM: Artificial Sequence
<220> FEATURE:
<223> OTHER INFORMATION: synthetic peptide

<400> SEQUENCE: 201

Ala Leu Ser Gly His Leu Glu Thr Val
1               5

<210> SEQ ID NO 202
<211> LENGTH: 9
<212> TYPE: PRT
<213> ORGANISM: Artificial Sequence
<220> FEATURE:
<223> OTHER INFORMATION: synthetic peptide

<400> SEQUENCE: 202

Ser Leu Leu Asp Lys Ile Ile Gly Ala
1               5
```

-continued

```
<210> SEQ ID NO 203
<211> LENGTH: 11
<212> TYPE: PRT
<213> ORGANISM: Artificial Sequence
<220> FEATURE:
<223> OTHER INFORMATION: synthetic peptide

<400> SEQUENCE: 203

Gly Leu Leu Gly Ala Gly Gly Thr Val Ser Val
1               5                   10

<210> SEQ ID NO 204
<211> LENGTH: 9
<212> TYPE: PRT
<213> ORGANISM: Artificial Sequence
<220> FEATURE:
<223> OTHER INFORMATION: synthetic peptide

<400> SEQUENCE: 204

Gly Leu Val Pro Phe Leu Val Ser Val
1               5
```